(12) United States Patent
Fuller et al.

(10) Patent No.: US 10,240,195 B2
(45) Date of Patent: Mar. 26, 2019

(54) CHEMICAL METHODS FOR PRODUCING TAGGED NUCLEOTIDES

(71) Applicants: Carl W. Fuller, Berkeley Heights, NJ (US); Shiv Kumar, Belle Mead, NJ (US); Jingyue Ju, Englewood Cliffs, NJ (US); Randall Davis, Pleasanton, CA (US); Roger Chen, Saratoga, CA (US)

(72) Inventors: Carl W. Fuller, Berkeley Heights, NJ (US); Shiv Kumar, Belle Mead, NJ (US); Jingyue Ju, Englewood Cliffs, NJ (US); Randall Davis, Pleasanton, CA (US); Roger Chen, Saratoga, CA (US)

(73) Assignees: THE TRUSTEES OF COLUMBIA UNIVERSITY IN THE CITY OF NEW YORK, New York, NY (US); GENIA TECHNOLOGIES, INC., Mountain View, CA (US)

( * ) Notice: Subject to any disclaimer, the term of this patent is extended or adjusted under 35 U.S.C. 154(b) by 715 days.

(21) Appl. No.: 14/666,124

(22) Filed: Mar. 23, 2015

(65) Prior Publication Data
US 2015/0368710 A1    Dec. 24, 2015

Related U.S. Application Data

(60) Provisional application No. 61/969,628, filed on Mar. 24, 2014.

(51) Int. Cl.
*C12Q 1/68*    (2018.01)
*C07H 19/10*    (2006.01)
(Continued)

(52) U.S. Cl.
CPC .......... *C12Q 1/6874* (2013.01); *C07H 17/02* (2013.01); *C07H 19/10* (2013.01); *C07H 19/20* (2013.01); *C12Q 1/6806* (2013.01)

(58) Field of Classification Search
None
See application file for complete search history.

(56) References Cited

U.S. PATENT DOCUMENTS 5,804,386 A    9/1998   Ju et al.
5,814,454 A    9/1998   Ju
(Continued)

FOREIGN PATENT DOCUMENTS

WO    WO2001/094609    12/2001
WO    WO 02/22883 A1    3/2002
(Continued)

OTHER PUBLICATIONS

Mar. 4, 2016 Office Action issued in connection with U.S. Appl. No. 14/516,785, Ju et al.
(Continued)

*Primary Examiner* — Kaijiang Zhang
(74) *Attorney, Agent, or Firm* — John P. White; Gary J. Gershik; Cooper & Dunham LLP

(57) ABSTRACT

This disclosure provides systems and methods for attaching nanopore-detectable tags to nucleotides. The disclosure also provides methods for sequencing nucleic acids using the disclosed tagged nucleotides.

20 Claims, 40 Drawing Sheets

Specification includes a Sequence Listing.

(51) Int. Cl.
*C07H 19/20* (2006.01)
*C12Q 1/6874* (2018.01)
*C07H 17/02* (2006.01)
*C12Q 1/6806* (2018.01)

(56) References Cited

U.S. PATENT DOCUMENTS

| | | |
|---|---|---|
| 5,876,936 A | 3/1999 | Ju |
| 5,952,180 A | 9/1999 | Ju et al. |
| 6,046,005 A | 4/2000 | Ju et al. |
| 6,627,748 B1 | 9/2003 | Ju et al. |
| 6,664,079 B2 | 12/2003 | Ju et al. |
| 7,074,597 B2 | 7/2006 | Ju |
| 7,345,159 B2 | 3/2008 | Ju et al. |
| 7,622,279 B2 | 11/2009 | Ju |
| 7,635,578 B2 | 12/2009 | Ju et al. |
| 7,713,698 B2 | 5/2010 | Ju et al. |
| 7,790,869 B2 | 9/2010 | Ju et al. |
| 7,883,869 B2 | 2/2011 | Ju et al. |
| 7,982,029 B2 | 7/2011 | Ju et al. |
| 8,088,575 B2 | 1/2012 | Ju et al. |
| 8,298,792 B2 | 10/2012 | Ju et al. |
| 8,541,849 B2 | 9/2013 | Chen et al. |
| 8,796,432 B2 | 8/2014 | Ju et al. |
| 8,889,348 B2 | 11/2014 | Ju |
| 9,115,163 B2 | 8/2015 | Ju et al. |
| 9,133,511 B2 | 9/2015 | Ju et al. |
| 9,169,510 B2 | 10/2015 | Ju et al. |
| 9,175,342 B2 | 11/2015 | Ju et al. |
| 9,255,292 B2 | 2/2016 | Ju et al. |
| 9,297,042 B2 | 3/2016 | Ju et al. |
| 9,890,426 B2 | 2/2018 | Ju et al. |
| 2003/0027140 A1 | 2/2003 | Ju et al. |
| 2006/0057565 A1 | 3/2006 | Ju et al. |
| 2006/0252038 A1 | 11/2006 | Ju et al. |
| 2009/0325154 A1 | 12/2009 | Ju |
| 2010/0129842 A1 | 5/2010 | Pappin et al. |
| 2011/0014611 A1 | 1/2011 | Ju et al. |
| 2011/0039259 A1 | 2/2011 | Ju et al. |
| 2011/0165652 A1* | 7/2011 | Hardin et al. .......... C07H 19/10 435/194 |
| 2011/0192723 A1 | 8/2011 | Chen et al. |
| 2011/0193249 A1 | 8/2011 | Chen et al. |
| 2011/0193570 A1 | 8/2011 | Chen et al. |
| 2011/0287414 A1 | 11/2011 | Chen et al. |
| 2012/0100633 A1 | 4/2012 | Manetto et al. |
| 2012/0142006 A1 | 6/2012 | Ju et al. |
| 2012/0156680 A1 | 6/2012 | Ju et al. |
| 2012/0160681 A1 | 6/2012 | Davis et al. |
| 2012/0160688 A1 | 6/2012 | Davis et al. |
| 2012/0187963 A1 | 7/2012 | Chen |
| 2012/0188092 A1 | 7/2012 | Chen |
| 2012/0196759 A1 | 8/2012 | Chen |
| 2013/0089884 A1 | 4/2013 | Agnew et al. |
| 2013/0244340 A1 | 9/2013 | Davis et al. |
| 2013/0264207 A1 | 10/2013 | Ju et al. |
| 2013/0280700 A1 | 10/2013 | Ju et al. |
| 2014/0034497 A1 | 2/2014 | Davis et al. |
| 2014/0093869 A1 | 4/2014 | Ju et al. |
| 2014/0206553 A1 | 7/2014 | Ju et al. |
| 2014/0315191 A1 | 10/2014 | Ju et al. |
| 2014/0377743 A1 | 12/2014 | Ju et al. |
| 2015/0037788 A1 | 2/2015 | Ju et al. |
| 2015/0080232 A1 | 3/2015 | Ju et al. |
| 2015/0111759 A1 | 4/2015 | Ju et al. |
| 2015/0119259 A1 | 4/2015 | Ju et al. |
| 2015/0197800 A1 | 7/2015 | Ju et al. |
| 2016/0024570 A1 | 1/2016 | Ju et al. |
| 2016/0024574 A1 | 1/2016 | Ju et al. |
| 2016/0041179 A1 | 2/2016 | Ju et al. |
| 2016/0090621 A1 | 3/2016 | Ju et al. |
| 2016/0208313 A1 | 7/2016 | Ju et al. |
| 2016/0264612 A1 | 9/2016 | Ju et al. |
| 2016/0265048 A1 | 9/2016 | Ju et al. |

FOREIGN PATENT DOCUMENTS

| | | | |
|---|---|---|---|
| WO | WO 02/29003 | 4/2002 | |
| WO | WO 02/79519 A1 | 10/2002 | |
| WO | WO 2004090154 A2 * | 10/2004 | ............ C07H 19/10 |
| WO | WO2009/054922 | 4/2009 | |
| WO | WO 2011/097028 A1 | 8/2011 | |
| WO | WO2012/083249 | 6/2012 | |
| WO | WO 2012/162429 | 11/2012 | |
| WO | WO2013/123450 | 8/2013 | |
| WO | WO 2013/154999 | 10/2013 | |
| WO | WO2013/188841 | 12/2013 | |
| WO | WO 2013/191793 | 12/2013 | |
| WO | WO 2014/144883 | 9/2014 | |
| WO | WO 2014/144898 | 9/2014 | |
| WO | WO2015/123430 | 8/2015 | |
| WO | WO2015/148402 | 10/2015 | |
| WO | WO2015/179284 | 11/2015 | |
| WO | WO2016/144973 | 9/2016 | |
| WO | WO2016/154215 | 9/2016 | |

OTHER PUBLICATIONS

Sep. 8, 2015 Response to Mar. 24, 2015 Office Action issued in connection with Chinese Patent Application No. 200780028545.1.
Nov. 13, 2015 Decision on Reexamination issued in connection with Chinese Patent Application No. 200780028545.1.
Feb. 3, 2016 Office Action issued in connection with Chinese Patent Application No. 200780028545.1.
Apr. 18, 2016 Response to Feb. 3, 2016 Office Action issued in connection with Chinese Patent Application No. 200780028545.1.
Jun. 29, 2016 Office Action issued in connection with Chinese Patent Application No. 200780028545.1.
Sep. 13, 2016 Amendment in Response to the Jun. 29, 2016 Office Action issued in connection with Chinese Patent Application No. 200780028545.1.
Notice on Grant of Patent Right for Invention dated Oct. 10, 2016 by the Chinese Patent Office in connection with Chinese Patent Application No. 200780028545.1, English translation.
Preliminary Amendment dated Feb. 17, 2015 in connection with U.S. Appl. No. 13/994,431.
Jul. 15, 2015 Communication pursuant to Article 94(3) EPC in connection with European Patent Application No. EP 11848220.7.
Jan. 15, 2016 Communication Pursuant to Article 94(3) EPC in connection with European Patent Application No. EP 11848220.7.
May 12, 2016 Amendment in Response to Communication Pursuant to Article 94(3) in connection with European Patent Application No. EP 11848220.7, Ju et al.
Aug. 5, 2016 Communication Under Rule 71(3) EPC issued by the European Patent Office in connection with European Patent Application No. EP11848220.7, Ju et al.
Jul. 13, 2015 Third Office Action in connection with Chinese Patent Application No. 201180063978.7 (with English translation of cover page only).
Sep. 28, 2015 Response to Jul. 13, 2015 Office Action issued in connection with Chinese Patent Application No. 201180063978.7.
Jan. 29, 2016 Office Action issued in connection with Chinese Patent Application No. 201180063978.7.
Mar. 31, 2016 Response to the Jan. 29, 2016 Office Action issued in connection with Chinese Patent Application No. 201180063978.7.
Jul. 29, 2016 Notice on Grant of Patent Right for Invention, issued in connection with Chinese Patent Application No. 201180063978.7 (English Translation).
Office Action dated Jul. 15, 2015 by the Chinese State Intellectual Property Office in connection with Chinese Patent Application No. 201380025837.5.
Response to the Jul. 15, 2015 Office Action, filed Jan. 29, 2016 in connection with Chinese Patent Application No. 201380025837.5.
May 4, 2016 Office Action issued by the Chinese State Intellectual Property Office in connection with Chinese Patent Application No. 201380025837.5.
Jul. 19, 2016 Amendment filed in Response to the May 4, 2016 Office Action issued by the State Intellectual Property Office of the

(56) References Cited

OTHER PUBLICATIONS

People's Republic of China in connection with Chinese Patent Application No. 201380025837.5.
Communication pursuant to Rule 164(1) EPC dated Dec. 7, 2015 by the EPO in connection with EP 13775787.8.
Extended European Search Report dated Mar. 11, 2016 by the EPO in connection with EP 13775787.8.
Oct. 10, 2016 Amendment in Response to the Extended European Search Report dated Mar. 11, 2016 by the EPO in connection with EP 13775787.8.
Mar. 16, 2016 Restriction Requirement issued in connection with U.S. Appl. No. 14/391,337.
Sep. 16, 2016 Response to the Mar. 16, 2016 Restriction Requirement issued in connection with U.S. Appl. No. 14/391,337.
International Search Report and Written Opinion of the International Searching Authority dated Sep. 24, 2013 in connection with PCT International Application No. PCT/US2013/035630.
Communication pursuant to Rule 164(1) EPC dated Dec. 2, 2015 by the EPO in connection with EP 13807639.3.
Extended European Search Report dated Mar. 11, 2016 by the EPO in connection with EP 13807639.3.
Oct. 10, 2016 Amendment in Response to the Extended European Search Report dated Mar. 31, 2016 by the EPO in connection with EP 13807639.3.
Voluntary Amendment filed Mar. 17, 2016 in connection with Chinese Patent Application No. CN 2014800159374.
Office Action dated Jul. 26, 2016 by the Chinese State Intellectual Property Office in connection with CN 201480015937.4.
Voluntary Amendment filed May 12, 2016 in connection with EP14764268.0, Ju et al.
Invitation Pursuant to Rule 62a(1) EPC, dated Oct. 7, 2016 in connection with EP14764268.0, Ju et al.
International Search Report and Written Opinion of the International Searching Authority dated Jun. 29, 2015 in connection with PCT International Application No. PCT/US2015/022063.
International Search Report and Written Opinion of the International Searching Authority dated Aug. 25, 2015 in connection with PCT International Application No. PCT/US2015/015647.
International Search Report dated May 20, 2016 in connection with WO2016/154215, The Trustees of Columbia University in the City of New York, Ju et al.
Written Opinion of the International Searching Authority dated May 20, 2016 in connection with WO2016/144973, The Trustees of Columbia University in the City of New York, Ju et al.
International Search Report dated Aug. 8, 2016 in connection with WO2016/154215, The Trustees of Columbia University in the City of New York, Ju et al.
Written Opinion of the International Searching Authority dated Aug. 8, 2016 in connection with WO2016/154215, The Trustees of Columbia University in the City of New York, Ju et al.
Aug. 4, 2015 Applicant Statement in connection with U.S. Appl. No. 14/666,124 regarding Amendments to p. 40 Regarding Tagged Nucleotides.
Restriction Requirement dated Feb. 9, 2017 in connection with U.S. Appl. No. 13/994,431, Ju et al.
Sep. 25, 2017 Non-Final Office Action issued in connection with U.S. Appl. No. 13/994,431, Ju et al.
Dec. 22, 2017 Amendment in Response dated Sep. 25, 2017 Non-Final Office Action issued in connection with U.S. Appl. No. 13/994,431, Ju et al.
Feb. 26, 2018 Non-Final Office Action issued in connection with U.S. Appl. No. 13/994,431, Ju et al.
Aug. 18, 2017 Amendment in Response to Communication Pursuant to Article 94(3) EPC, issued by the European Patent Office in connection with EP 13775787.8, Ju et al.
Apr. 13, 2018 Communication Pursuant to Article 94(3) EPC, issued by the European Patent Office in connection with EP 13775787.8, Ju et al.
Aug. 18, 2017 Amendment in Response to Communication Pursuant to Article 94(3), dated Feb. 9, 2017 by the European Patent Office in connection with EP 13807639.3, Ju et al.
Communication Pursuant to Article 94(3), dated Feb. 23, 2018 by the European Patent Office in connection with EP 13807639.3, Ju et al.
Jun. 5, 2018 Amendment in Response dated Dec. 6, 2017 Non-Final Office Action issued by the United States Patent and Trademark Office in connection with U.S. Appl. No. 14/391,320.
Nov. 9, 2017 Extended European Search Report issued by the European Patent Office in connection with EP 15768383.0, Fuller et al.
Jun. 7, 2018 Amendment in Response dated Nov. 9, 2017 Extended European Search Report issued by the European Patent Office in connection with EP 15768383.0, fuller et al.

* cited by examiner (dCp)$_m$-(PO$_4$)$_n$-dC (dGp)$_m$-(PO$_4$)$_n$-dG

Coumarin-PEG16-NH₂

Coumarin-PEG20-NH₂

Coumarin-PEG24-NH₂

Coumarin-PEG36-NH₂

(A)

β-D-nucleoside

α-D-nucleoside (B)

3', 5'-linked oligonucleotide

2', 5'-linked oligonucleotide (A)

(B)

CHEMICAL METHODS FOR PRODUCING TAGGED NUCLEOTIDES

This application claims benefit under 35 U.S.C. § 119(e) of U.S. Provisional Patent Application Ser. No. 61/969,628, filed Mar. 24, 2014, the contents of which are hereby incorporated herein by reference.

This application incorporates-by-reference nucleotide and/or amino acid sequences which are present in the file named "150805_0575_85625_SequenceListing_JAK.txt," which is 52 kilobytes in size, and which was created Aug. 5, 2015 in the IBM-PC machine format, having an operating system compatibility with MS-Windows, which is contained in the text file filed Aug. 5, 2015 as part of this application.

This invention was made with government support under grant HG007415 awarded by the National Institutes of Health. The Government has certain rights in this invention.

TECHNICAL FIELD

This application relates to tagged nucleotide compositions, methods of preparing and using the disclosed tagged nucleotide compositions for sequencing nucleic acids, and in particular, nanopore-based sequencing methods.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

Nucleic acid sequencing is the process for determining the nucleotide sequence of a nucleic acid. Such sequence information may be helpful in diagnosing and/or treating a subject. For example, the sequence of a nucleic acid of a subject may be used to identify, diagnose and potentially develop treatments for genetic diseases. As another example, research into pathogens may lead to treatment for contagious diseases. Since some diseases are characterized by as little as one nucleotide difference in a chain of millions of nucleotides, highly accurate sequencing is essential.

There are methods available that may be used to sequence a nucleic acid. Such methods, however, are expensive and may not provide sequence information within a time period and at an accuracy that may be necessary to diagnose and/or treat a subject.

In some instances, methods of nucleic acid sequencing that pass a single stranded nucleic acid molecule through a nanopore have insufficient sensitivity. Nucleotide bases (e.g., adenine (A), cytosine (C), guanine (G), thymine (T) and/or uracil (U)) may not provide a sufficiently distinct signal from each other. In particular, the purines (i.e., A and G) are of a similar size, shape and charge to each other and provide an insufficiently distinct signal in some instances. Also, the pyrimidines (i.e., C, T and U) are of a similar size, shape and charge to each other and provide an insufficiently distinct signal in some instances.

Kumar et al. (2012) describes using a nanopore to distinguish four different length PEG-coumarin tags attached via a terminal 5'-phosphoramidate to a dG nucleotide, and separately demonstrates efficient and accurate incorporation of these four PEG-coumarin tagged dG nucleotides by DNA polymerase. See also, U.S. Patent Application Publication Nos. US 2013/0244340 A1 and US 2013/0264207 A1.

Recognized herein is the need for improved compositions and methods for nucleotide identification and nucleic acid sequencing.

SUMMARY

Provided herein are nucleotides with attached tags and methods for attaching tags to nucleotides. The tags can be attached by chemical reactions, such as "click chemistry".

In an aspect, the present disclosure provides a tagged nucleotide, comprising: (a) a poly-phosphate moiety having a terminal phosphate; and (b) a tag covalently coupled to the terminal phosphate of the nucleotide by a triazole, a 1,2-diazine, a disulfide, a secondary amine, a hydrazone, a thio-acetamide, or a maleimide-thioadduct.

In some embodiments of the tagged nucleotide, the tag is covalently coupled to the terminal phosphate by a triazole. In some embodiments, the triazole has the structure:

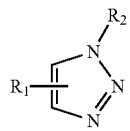

wherein $R_1$ comprises a tag, and $R_2$ comprises a nucleotide; or wherein $R_1$ comprises a nucleotide, and $R_2$ comprises a tag. In some embodiments, the triazole has the structure:

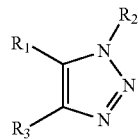

wherein $R_1$ and $R_3$ combine to form a cyclic moiety; and wherein $R_1$ and $R_3$ combined comprise a tag, and $R_2$ comprises a nucleotide; or wherein $R_1$ and $R_3$ combined comprise a nucleotide, and $R_2$ comprises a tag. In some embodiments, the triazole is formed by a reaction between an azide and an alkyne.

In some embodiments of the tagged nucleotide, the tag is covalently coupled to the terminal phosphate by a 1,2-diazine. In some embodiments, the 1,2-diazine comprises a dihydropyridazine moiety. In some embodiments, the 1,2-diazine or dihydropyridazine moiety is formed by reaction between a tetrazine and a trans-cyclooctene.

In some embodiments of the tagged nucleotide, the poly-phosphate moiety is at the 5'-position of the nucleotide. In some embodiments, the poly-phosphate moiety comprises at least 3 phosphates, at least 4 phosphates, at least 5 phosphates, at least 6 phosphates, or at least 7 phosphates. In some embodiments, the poly-phosphate moiety comprises from 4 to 6 phosphates. In some embodiments, the poly-phosphate moiety comprises 6 phosphates.

In some embodiments, the covalent coupling between the tag and the terminal phosphate can comprise a linker or a spacer moiety. In some embodiments, the linker or spacer moiety comprises an alkyl group of at least 2 carbons to about 12 carbons.

In some embodiments of the tagged nucleotide, the tag comprises nucleotides, oligonucleotides, peptides, polyethylene glycol (PEG), oligo-saccharides, carbohydrates, peptide nucleic acids (PNA), vinyl polymers, other water-soluble polymers, or any combination thereof.

In some embodiments of the tagged nucleotide, the tag comprises an oligonucleotide. In some embodiments, the oligonucleotide tag comprises at least 7 monomer units, at least 10 monomer units, at least 15 monomer units, at least 20 monomer units, at least 25 monomer units, at least 30 monomer units, at least 35 monomer units, at least 40 monomer units, or at least 50 or more monomer units.

In some embodiments of the tagged nucleotide, the tag comprises an oligonucleotide wherein the oligonucleotide comprises an unnatural nucleotide. In some embodiments, the unnatural nucleotide comprises a group selected from the group consisting of an L-nucleotide, a 2', 5'-linkage, an α-D-nucleotide, a non-naturally occurring internucleotide linkage, a non-naturally-occurring base, a non-naturally occurring sugar moiety, and any combination thereof. In some embodiments, the unnatural nucleotide comprises a non-naturally occurring base is selected from the group consisting of nitropyrrole, nitroindole, nebularine, zebularine, benzene, and benzene derivatives. In some embodiments, the unnatural nucleotide comprises a non-naturally occurring internucleotide linkage selected from the group consisting of a phosphotriester, phosphorothioate, methylphosphonate, boronophosphate, phosphoramidate and a morpholino moiety.

In some embodiments of the tagged nucleotide, the tag comprises an oligonucleotide wherein the 5'-end of the oligonucleotide is covalently coupled to the terminal phosphate of a poly-phosphate moiety. In some embodiments, the oligonucleotide with the 5'-end covalently coupled to the terminal phosphate further comprises a chemical modification of its 3' terminus that protects it from exonuclease degradation. In some embodiments, the chemical modification of its 3' terminus is selected from phosphorylation, and covalent coupling with a $C_3$-alkyl to $C_{12}$-alkyl spacers. In other embodiments of the tagged nucleotide, the tag comprises an oligonucleotide wherein the 3'-end of the oligonucleotide is covalently coupled to the terminal phosphate of a poly-phosphate moiety. In some embodiments, the oligonucleotide with the 3'-end covalently coupled to the terminal phosphate further comprises a chemical modification of its 5' terminus that protects it from exonuclease degradation. In some embodiments, the chemical modification of its 5' terminus is selected from phosphorylation, and covalent coupling with a $C_3$-alkyl to $C_{12}$-alkyl spacers.

In some embodiments of the tagged nucleotide, the tag comprises an oligonucleotide wherein the oligonucleotide comprises a linker comprising a cyanine dye moiety. In some embodiments, the cyanine dye moiety is a Cy3 moiety.

In another aspect, the disclosure provides a process for making a tagged nucleotide, comprising: (a) providing a nucleotide comprising a poly-phosphate moiety that comprises a terminal phosphate, wherein the terminal phosphate is coupled to a linker that comprises a first reactive functional group; (b) providing a tag comprising a second reactive functional group; and (c) reacting the first reactive functional group with the second reactive functional group to link the nucleotide to the tag, wherein the first reactive functional group is selected from (i) the group consisting of a thiol, an imidazole, an amine, an alkyne and a diene, and the second reactive functional group is selected from (ii) the group consisting of a maleimide, a haloacetamide, an aldehyde, an isothiocyanate, an isocyanate, a vinyl sulphone, an azide and a tetrazine, or vice versa (i.e. the first reactive functional group is selected from (ii), and the second reactive functional group is selected from (i)).

In some embodiments, the first reactive functional group is different than the second reactive functional group.

In some embodiments, the first reactive functional group is selected from the group consisting of a thiol, an imidazole, an amine, an alkyne and a diene.

In some embodiments, the second reactive functional group is selected from the group consisting of a maleimide, a haloacetamide, an aldehyde, an isothiocyanate, an isocyanate, a vinyl sulphone, an azide and a tetrazine.

In some embodiments, the first reactive functional group is an alkyne and the second reactive functional group is an azide.

In some embodiments, the alkyne is a cyclooctyne.

In some embodiments, the first reactive functional group is selected from the group consisting of a maleimide, a haloacetamide, an aldehyde, an isothiocyanate, an isocyanate, a vinyl sulphone, an azide and a tetrazine.

In some embodiments, the second reactive functional group is selected from the group consisting of a thiol, an imidazole, an amine, an alkyne and a diene.

In some embodiments, the first reactive functional group is an azide and the second reactive functional group is an alkyne.

In some embodiments, the alkyne is a cyclooctyne.

In some embodiments, the reaction is facilitated by a heterogeneous catalyst comprising copper, ruthenium, silver, or any combination thereof.

In some embodiments, the reaction is not facilitated by a heterogeneous catalyst.

In another aspect, the disclosure provides a kit for sequencing nucleic acid comprising at least one tagged nucleotide.

In some embodiments of the invention, the tag is selected from the group consisting of the tags listed in Table 4.

In some embodiments of the invention, the tagged nucleotide is selected from the group consisting of the tagged nucleotides listed in Table 4.

In some embodiments of the invention, the tag is selected from the group consisting of the tags listed in Table 5.

In some embodiments of the invention, the tag comprises a chemical modification selected from the group consisting of the chemical modifications listed in Table 6.

In some embodiments of the invention, the tagged nucleotide comprises a cyanine dye moiety in a linker connecting the tag to the nucleotide, and the tagged nucleotide has an improved rate of capture by a polymerase compared to a tagged nucleotide without a cyanine dye moiety.

The disclosure provides methods for determining the nucleotide sequence of a single-stranded nucleic acid (DNA or RNA) that use the tagged nucleotides disclosed herein. Thus, in another aspect, the disclosure provides a method for determining the nucleotide sequence of a single-stranded nucleic acid (DNA or RNA) comprising:

(a) contacting the single-stranded nucleic acid, wherein the single-stranded nucleic acid is in an electrolyte solution in contact with a nanopore in a membrane and wherein the single-stranded nucleic acid has a primer hybridized to a portion thereof, with a nucleic acid polymerase and at least four tagged nucleotides under conditions permitting the nucleic acid polymerase to catalyze incorporation of one of the tagged nucleotides into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a nucleic acid extension product,
wherein each of the at least four tagged nucleotides comprises a poly-phosphate moiety having a terminal phosphate, a base which is adenine, guanine, cytosine, thymine, or uracil, or a derivative of each thereof, and a tag covalently coupled to the terminal phosphate of the nucleotide by a triazole, a 1,2-diazine, a disulfide, a hydrazone, a secondary amine, a thio-acetamide, or a maleimide-thioadduct,
wherein (i) the type of base in each tagged nucleotide is different from the type of base in each of the other three tagged nucleotides, and (ii) either the number of phosphates in the poly-phosphate moiety of each tagged nucleotide is different from the number of phosphates in the poly-phosphate moiety of the other three tagged nucleotides, or the number of phosphates in the poly-phosphate moiety of each tagged nucleotide is the same and the type of tag on each tagged nucleotide is different from the type of tag on each of the other three tagged nucleotides,
wherein incorporation of the tagged nucleotide results in release of a polyphosphate having the tag attached thereto;
(b) determining which tagged nucleotide has been incorporated into the primer to form a nucleic acid extension product in step (a) by applying a voltage across the membrane and measuring an electronic change across the nanopore resulting from the polyphosphate having the tag attached thereto generated in step (a) entering into, becoming positioned in, and/or translocating through the nanopore, wherein the electronic change is different for each different number of phosphates in the poly-phosphate moiety, or for each different type of tag, as appropriate, thereby identifying the nucleotide residue in the single-stranded nucleic acid complementary to the incorporated tagged nucleotide; and
(c) iteratively performing steps (a) and (b) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product,
thereby determining the nucleotide sequence of the single-stranded nucleic acid.

In another aspect of the methods, the disclosure provides a method for determining the nucleotide sequence of a single-stranded nucleic acid (DNA or RNA) comprising:
(a) contacting the single-stranded nucleic acid, wherein the single-stranded nucleic acid is in an electrolyte solution in contact with a nanopore in a membrane and wherein the single-stranded nucleic acid has a primer hybridized to a portion thereof, a nucleic acid polymerase and a tagged nucleotide under conditions permitting the nucleic acid polymerase to catalyze incorporation of the tagged nucleotide into the primer if it is complementary to the nucleotide residue of the single-stranded nucleic acid which is immediately 5' to a nucleotide residue of the single-stranded nucleic acid hybridized to the 3' terminal nucleotide residue of the primer, so as to form a nucleic acid extension product, wherein the tagged nucleotide comprises a poly-phosphate moiety having a terminal phosphate, a base which is adenine, guanine, cytosine, thymine, or uracil, or a derivative of each thereof, and a tag covalently coupled to the terminal phosphate of the nucleotide by a triazole, a 1,2-diazine, a disulfide, a hydrazone, a thio-acetamide, or a maleimide-thioadduct,
wherein incorporation of a tagged nucleotide results in release of a polyphosphate having the tag attached thereto and wherein if the tagged nucleotide is not incorporated, iteratively repeating the contacting with a different tagged nucleotide until a tagged nucleotide is incorporated, with the proviso that (1) the type of base in each tagged nucleotide is different from the type of base in each of the other three tagged nucleotides, and (2) either the number of phosphates in the poly-phosphate moiety of each tagged nucleotide is different from the number of phosphates in the poly-phosphate moiety of the other three tagged nucleotides, or the number of phosphates in the poly-phosphate moiety of each tagged nucleotide is the same and the type of tag on each tagged nucleotide is different from the type of tag on each of the other three tagged nucleotides;
(b) determining which tagged nucleotide has been incorporated into the primer to form a nucleic acid extension product in step (a) by applying a voltage across the membrane and measuring an electronic change across the nanopore resulting from the polyphosphate having the tag attached thereto generated in step (a) entering into, becoming positioned in, and/or translocating through the nanopore, wherein the electronic change is different for each value of n, or for each different type of tag, as appropriate, thereby identifying the nucleotide residue in the single-stranded nucleic acid complementary to the incorporated tagged nucleotide; and
(c) iteratively performing steps (a) and (b) for each nucleotide residue of the single-stranded nucleic acid being sequenced, wherein in each iteration of step (a) the tagged nucleotide is incorporated into the nucleic acid extension product resulting from the previous iteration of step (a) if it is complementary to the nucleotide residue of the single-stranded nucleic acid which is immediately 5' to a nucleotide residue of the single-stranded nucleic acid hybridized to the 3' terminal nucleotide residue of the nucleic acid extension product,
thereby determining the nucleotide sequence of the single-stranded nucleic acid.

In some embodiments of the methods, each poly-phosphate moiety comprises at least 3 phosphates, at least 4 phosphates, at least 5 phosphates, at least 6 phosphates, at least 7 phosphates, or in some embodiments at least 8 phosphates. In some embodiments, the poly-phosphate moiety comprises from 4 to 6 phosphates. In some embodiments, the poly-phosphate moiety comprises 6 phosphates.

In some embodiments of the methods, each tag is covalently coupled to the terminal phosphate by a triazole. In some embodiments, each triazole has the structure:

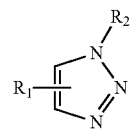

wherein $R_1$ comprises the tag, and $R_2$ comprises the nucleotide; or
wherein $R_1$ comprises the nucleotide, and $R_2$ comprises the tag.

In some embodiments of the methods, each triazole has the structure:

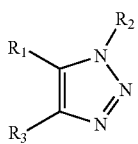

wherein $R_1$ and $R_3$ combine to form a cyclic moiety; and wherein $R_1$ and $R_3$ combined comprise a tag, and $R_2$ comprises a nucleotide; or wherein $R_1$ and $R_3$ combined comprise a nucleotide, and $R_2$ comprises a tag.

In some embodiments of the methods, each triazole is formed by a reaction between an azide and an alkyne.

In some embodiments of the methods, each tag is covalently coupled to the terminal phosphate by a 1,2-diazine.

In some embodiments, each tag comprises nucleotides, oligonucleotides, peptides, polyethylene glycol (PEG), oligo-saccharides, carbohydrates, peptide nucleic acids (PNA), vinyl polymers, other water-soluble polymers, or any combination thereof.

In some embodiments, each tag comprises a chemical modification selected from the group consisting of the chemical modifications listed in Table 6.

In some embodiments, each tagged nucleotide is selected from the group consisting of the tagged nucleotides listed in Table 4.

In some embodiments, each tagged nucleotide comprises a cyanine dye moiety in a linker connecting the tag to the nucleotide, and the tagged nucleotide has an improved rate of capture by a polymerase compared to a tagged nucleotide without a cyanine dye moiety.

In some embodiments, the four tagged nucleotides are dA6P-Cy3-T$_4$-FldT-T-FldT-T$_{23}$-C3, dT6P-Cy3-T$_2$-dSp8-T$_{20}$-C3, dG6P-Cy3-T$_{30}$-C6, and dC6P-Cy3-T$_4$-dSp3-T$_{23}$-C3.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also referred to as "Figures" or "FIGS.") of which:

DETAILED DESCRIPTION

Figure 1:
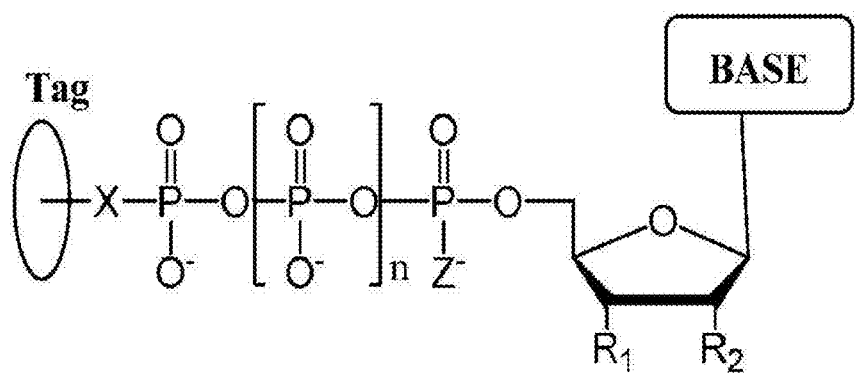
FIG. 1 shows a tag attached to the terminal phosphate of a nucleotide.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nanopore," as used herein, generally refers to a pore, channel or passage formed or otherwise provided in a membrane. A membrane may be an organic membrane, such as a lipid bilayer, or a synthetic membrane, such as a membrane formed of a polymeric material. The nanopore may be disposed adjacent or in proximity to a sensing circuit, such as, for example, a complementary metal-oxide semiconductor (CMOS) or field effect transistor (1-ET) circuit. A nanopore may have a characteristic width or diameter on the order of 0.1 nanometers (nm) to about 1000 nm. Some nanopores are proteins. α-hemolysin is an example of a protein nanopore.

The term "nucleic acid," as used herein, generally refers to a molecule comprising one or more nucleotide subunits. A nucleotide may include one or more subunits selected from adenine (A), cytosine (C), guanine (G), thymine (T) and uracil (U). In some examples, a nucleic acid is deoxyribonucleic acid (DNA) or ribonucleic acid (RNA), or derivatives thereof. A nucleic acid may be single-stranded or double stranded.

The term "tag," as used herein, generally refers to an atom or molecule that enables the detection or identification of a molecular complex that is coupled to the tag. A tag can provide a detectable signature, such as an electrostatic, electrochemical and/or optical signature (light).

The term "nucleotide," as used herein refers to a nucleoside-5'-polyphosphate compound, or structural analog of a nucleoside-5'-polyphosphate, which is capable of acting as a substrate or inhibitor of a nucleic acid polymerase to extend a growing nucleic acid chain. Exemplary nucleotides include, but are not limited to, nucleoside-5'-triphosphates (e.g., dATP, dCTP, dGTP, dTTP, and dUTP); nucleosides (e.g., dA, dC, dG, dT, and dU) with 5'-polyphosphate chains of 4 or more phosphates in length (e.g., 5'-tetraphosphate, 5'-pentaphosphate, 5'-hexaphosphate, 5'-heptaphosphate, 5'-octaphosphate); and structural analogs of nucleoside-5'-triphosphates that can have a modified base moiety (e.g., a substituted purine or pyrimidine base), a modified sugar (e.g., an O-alkylated sugar), and/or a modified polyphosphate moiety (e.g., a polyphosphate comprising a thio-phosphate, a methylene, and/or other bridges between phosphates).

The term "tagged nucleotide," as used herein refers to any nucleoside-5'-polyphosphate with a nanopore-detectable tag attached to the polyphosphate moiety, base moiety, or sugar moiety. A nanopore-detectable tag includes any molecular group or moiety (e.g., a linker, oligomer, polymer) that can enter into, become positioned in, be captured by, translocate through, and/or traverse a nanopore and thereby result in a detectable change in current through the pore. Exemplary nanopore-detectable tags include, but are not limited to, natural or synthetic polymers, such as polyethylene glycol, oligonucleotides, polypeptides, carbohydrates, peptide nucleic acid polymers, locked nucleic acid polymers, any of which may be optionally modified with or linked to chemical groups, such as dye moieties, or fluorophores, that can result in detectable pore current changes.

The term "oligonucleotide," as used herein, refers to an oligomer of nucleotide monomer units wherein the oligomer optionally includes non-nucleotide monomer units, and/or other chemical groups attached at internal and/or external positions of the oligomer. The oligomer can be natural or synthetic and can include naturally-occurring oligonucleotides, or oligomers that include nucleosides with non-naturally-occurring (or modified) bases, sugar moieties, phosphodiester-analog linkages, and/or alternative monomer unit chiralities and isomeric structures (e.g., 5'-to-2' linkage, L-nucleosides, α-anomer nucleosides). Exemplary oligonucleotides useful as nanopore-detectable tags in the composition and methods of the present disclosure include the oligonucleotide tag structures shown in Table 4.

The term "nucleotide analog," as used herein, refers to a chemical compound that is structurally similar to a nucleoside-5'-triphosphate and capable of serving as a substrate or inhibitor of a nucleic acid polymerase to extend a growing nucleic acid chain. A nucleotide analog may have a modified base moiety, for example a substituted purine or pyrimidine base, a modified sugar such as an O-alkylated sugar, and/or a modified polyphosphate moiety, for example, a polyphosphate comprising a thiophosphate, a methylene, and/or other bridges between phosphates. It can have more than three phosphates in the polyphosphate chain, and it can be detectably tagged on any of the base, sugar or polyphosphate moieties.

Described herein are methods, devices and systems useful for sequencing nucleic acids using a nanopore. The methods may accurately detect individual nucleotide incorporation events, such as upon the incorporation of a nucleotide by a nucleic acid polymerase into a growing strand that is complementary to a template nucleic acid strand. An enzyme (e.g., DNA polymerase) may incorporate nucleotides to a growing polynucleotide chain, wherein the added nucleotide is complimentary to the corresponding template nucleic acid strand which is hybridized to the growing strand. These nucleotide incorporation events include capturing the nucleotide, reading the associated tag in the pore, and releasing the tag from the nucleotide and the released tag then passes through a nanopore. In this way, the incorporated base may be identified (i.e., A, C, G, T or U) because a unique tag is first read and then released from each type of nucleotide (i.e., A, C, G, T or U).

Nucleotide incorporation events may be detected with the aid of a nanopore in real-time (i.e., as they occur) or following a sequencing reaction by analyzing the nanopore data. In some instances, an enzyme (e.g., DNA polymerase) attached to or in proximity to the nanopore may facilitate the flow of a nucleic acid molecule through or adjacent to the nanopore, and position the tag of a complimentary nucleotide in the nanopore for detection. Thus, a complimentary tagged nucleotide binding to an enzyme (prior to release of the tag) can result in the positioning of the tag in the pore of the nanopore, which can then be detected by a change in the current level through the nanopore. Or one or more tag molecules (also "tags" herein) may be detected subsequent to release as the tag flows through or adjacent to the nanopore. In some cases, an enzyme attached to or in proximity to the nanopore may aid in detecting tags or other by-products released upon the incorporation of one or more nucleotides. See, for example, U.S. Pat. No. 8,889,348; U.S. Patent Application Publication No. US 2013/0264207 A1; and PCT International Application Publication Ser. Nos. PCT/US13/35630 and. PCT/US13/35635, each of which is hereby incorporated herein by reference in its entirety.

Methods described herein may be single-molecule methods. That is, the signal that is detected is generated by a single molecule (i.e., single nucleotide incorporation) and is not generated from a plurality of clonal molecules. The method may not require DNA amplification.

Nucleotide incorporation events may occur from a mixture comprising a plurality of nucleotides (e.g., deoxyribonucleotide triphosphate (dNTP where N is adenosine (A), cytidine (C), thymidine (T), guanosine (G), or uridine (U) and derivatives thereof). Nucleotide incorporation events do not necessarily occur from a solution comprising a single type of nucleotide (e.g., dATP). Nucleotide incorporation events do not necessarily occur from alternating solutions of a plurality of nucleotides (e.g., dATP, followed by dCTP, followed by dGTP, followed by dTTP, followed by dATP). Additionally, as described throughout the present disclosure, the nucleotide incorporation events also can occur from a mixture of tagged nucleotides, wherein the tagged nucleotide can comprise 5'-polyphosphate chains of 4 or more phosphates in length (e.g., 5'-tetraphosphate, 5'-pentaphosphate, 5'-hexaphosphate, 5'-heptaphosphate, 5'-octaphosphate), and comprise further chemical moieties in the tag.

Chemical Conjugation Methods Such as "Click Chemistry"

Figure 21:
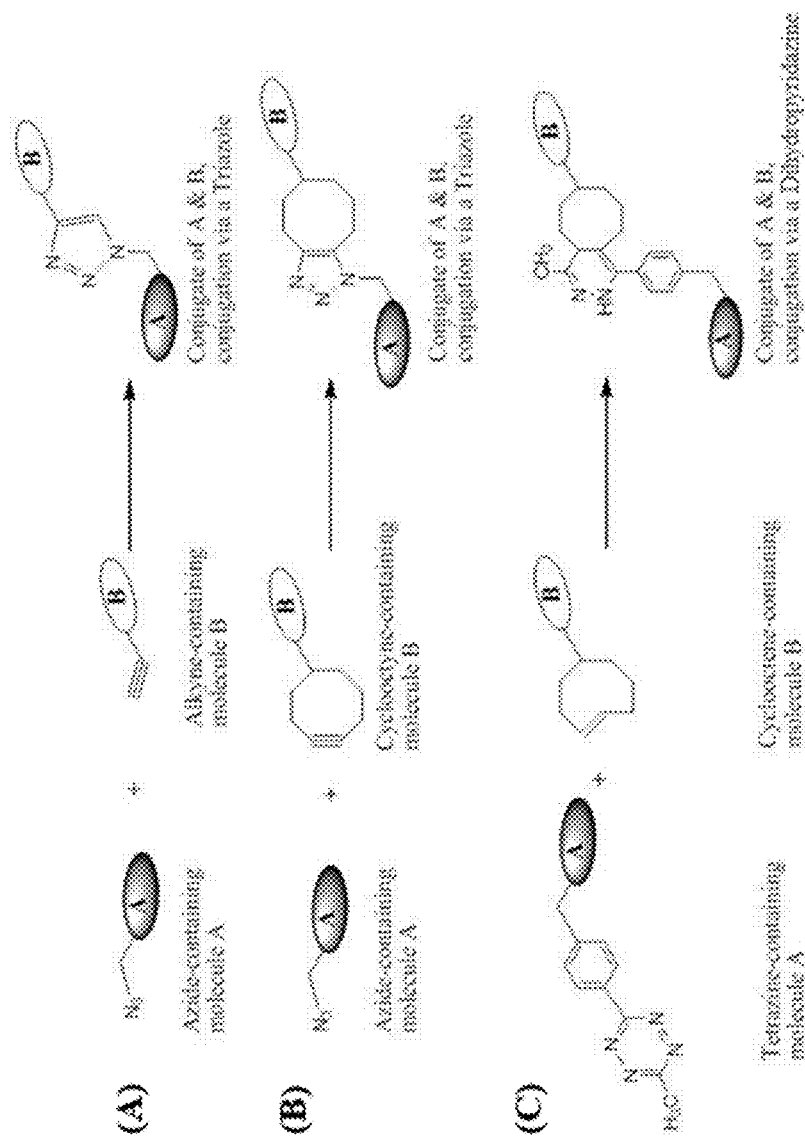
FIG. 21 shows exemplary click chemistry reactions useful for making the tagged nucleotides of the present disclosure, where (A) shows a click reaction between an azide-modified A compound and an alkyne-modified B compound to produce an A-B conjugate with a triazole covalent coupling, where (B) shows a click reaction between an azide-modified A compound and an cyclooctyne-modified B compound (e.g., as in a Cu-free click reaction) to produce an A-B conjugate with a triazole covalent coupling, and where (C) shows a click reaction (e.g., an IEDDA click reaction) between an tetrazine-modified A compound and a trans-cyclooctene-modified B compound to produce an A-B conjugate with a 1,2-diazine covalent coupling in the dihydropyridazine tautomeric form.

Described herein are methods for attaching tags to nucleotides using chemical conjugation. In some embodiments, the tag is attached to the nucleotide using a "click chemistry" reaction or "click reaction." Click reactions are fast, irreversible reactions between pairs of specific chemical groups, such as azides and alkynes (or cyclooctynes), or tetrazines and trans-cyclooctenes. The specific pairs of chemical groups used in click reactions provide covalent linkages that comprise specific chemical groups, such as triazole, or 1,2-diazine (or its tautomer, dihydropyridazine) as part of the covalent linkage. FIG. 21 depicts general reaction schemes illustrating three exemplary click reactions useful in preparing the tagged nucleotide conjugates of the present disclosure. These three exemplary reactions are described further below.

An exemplary click reaction between azide and alkyne is the azide-alkyne Huisgen cycloaddition. The azide-alkyne Huisgen cycloaddition is a 1,3-dipolar cycloaddition between a compound with an azide group and a compound with a terminal or internal alkyne group to yield a product compound with a 1,2,3-triazole covalent linkage. The exemplary azide-alkyne Huisgen click reaction follows the general scheme of FIG. 21, scheme (A), and is further detailed in the scheme below.

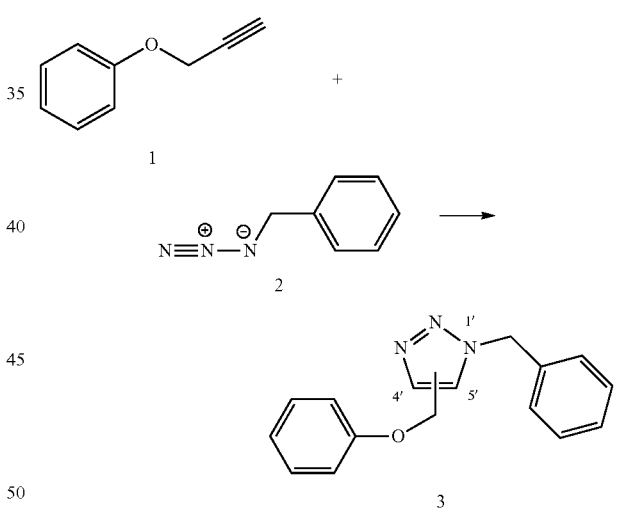

In the exemplary azide-alkyne cycloaddition reaction scheme above (e.g., carried out at 98° C. in 18 hours), the azide group of compound 2 reacts with alkyne group of compound 1 to afford a product composition 3 which is a mixture of 1,4-triazole and 1, 5-triazole adducts.

Copper-catalyzed azide-alkyne cycloaddition reaction also provides click reaction products coupled a covalent triazole linkage but can proceed with an enormous rate acceleration of between about $10^7$-fold and $10^8$-fold compared to un-catalyzed 1,3-dipolar cycloaddition. Further, this Cu-catalyzed click reaction can take place over a broad temperature range, can be insensitive to aqueous conditions and a pH range from about 4 to about 12, can tolerate a broad range of functional groups, and can yield single isomers under appropriate conditions. See e.g., Himo et al. (2005), which is hereby incorporated herein by reference in its entirety. The Cu-catalyzed chemical reaction follows the general scheme for conjugating two compounds (A and B) shown in FIG. 21, scheme (A), and is further detailed in the scheme below.

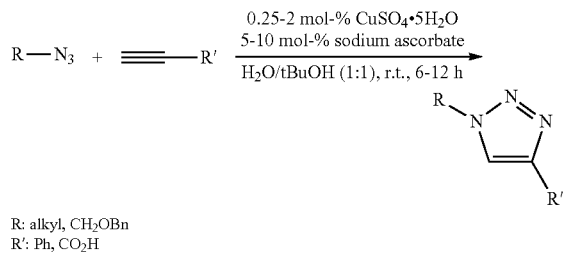

R: alkyl, CH$_2$OBn
R': Ph, CO$_2$H

Because of its tolerance for aqueous conditions the Cu-catalyzed azide-alkyne click reaction has been used for covalent conjugation of biological molecules. See e.g., Wang et al. (2003) and Presolski et al. (2011). This Cu-catalyzed azide-alkyne click-reaction also can be used to attach tags to nucleotides in accordance with the methods of the present disclosure and provide tagged nucleotides comprising a triazole in the covalent linkage between the tag and the nucleotide.

Copper-free click-reactions also have been developed that utilize cycloaddition reaction between an azide-modified compound and a cyclooctyne-modified compound (e.g., modified with dibenzyl-cyclooctyne "DBCO") to yield a product conjugate of the two compounds comprising a covalent triazole linkage. See e.g., Jewett and Bertozzi (2010). A general scheme for the use of the Cu-free azide-cyclooctyne click reaction to conjugate two compounds A and B with a triazole is depicted in FIG. 21, scheme (B). In some embodiments, this Cu-free click-reaction can be used to attach tags to nucleotides in accordance with the methods of the present disclosure and provide tagged nucleotides comprising a triazole in the covalent linkage between the tag and the nucleotide.

Another click chemistry reaction useful for providing the tagged nucleotides of the present disclosure is the inverse-electron demand Diels-Alder (IEDDA) reaction. See e.g., Reiner et al. (2014) and U.S. Patent Application Publication Nos. 2013/0266512 A1 and 2013/0085271 A1. The IEDDA click-reaction uses the fast, irreversible reaction between a tetrazine-modified compound and trans-cyclooctene modified compound to provide a conjugate product that comprises a covalent 1,2-diazine linkage, or more specifically, the tautomeric equivalent of a 1,2-diazine, a dihydropyridazine. A general scheme for the use of the IEDDA click reaction between tetrazine and trans-cyclooctene for conjugating two compounds A and B with a 1,2-diazine (dihydropyridazine tautomer) group is depicted in FIG. 21, scheme (C). Accordingly, in some embodiments, this IEDDA click-reaction also can be used to attach tags to nucleotides in accordance with the methods of the present disclosure and provide tagged nucleotides comprising a 1,2-diazine (dihydropyridazine tautomer) in the covalent linkage between the tag and the nucleotide.

Connection of the nucleotide polyphosphate to the tag can also be achieved by the formation of a disulfide (forming a readily cleavable connection), formation of an amide, formation of an ester, by alkylation (e.g., using a substituted iodoacetamide reagent) or forming adducts using aldehydes and amines or hydrazines. Numerous conjugation chemistries can be found in Hermanson (May 2, 2008), which is incorporated herein by reference in its entirety.

Tagged Nucleotides

In some cases, a tagged nucleotide comprises a tag (or label) that is separated from the nucleoside during a polymerase-catalyzed nucleotide incorporation event. The tag may be attached to the 5'-phosphate or 5'-polyphosphate chain of the nucleotide. In some instances, the tag does not comprise a fluorophore. The tag can be detectable by a nanopore and identified (e.g., distinguished from other tags) by its charge, shape, size, or any combination thereof. Examples of tags include various polymers. Each type of nucleotide (i.e., A, C, G, T, U) generally comprises a uniquely recognizable tag.

Tags of the present disclosure may be molecules that may be detectable using electrostatic, electrochemical, and/or optical approaches. In some examples, a tag may provide an electronic signature that is unique to a given nucleic acid molecule (e.g., A, C, G, T, U).

Tags may be located on any suitable position on the nucleotide. FIG. 1 shows a potential tagged nucleotide, where R$_1$ can be OH and R$_2$ can be H (i.e., for deoxyribonucleotides) or OH (i.e., for ribonucleotides), although other choices for R$_1$ and R$_2$ are acceptable. In FIG. 1, X is any suitable linker. In some cases, the linker is cleavable. Examples of linkers include without limitation, O, NH, S or CH$_2$. The linker may also contain, for example, O, N, S, or P atoms. The linker can also be a detectable moiety, directly or indirectly, such as amino acids, peptides, proteins, carbohydrates, PEGs of different length and molecular weights, organic or inorganic dyes, fluorescent and fluorogenic dyes, drugs, oligonucleotides, mass tags, chemiluminiscent tags and may contain positive or negative charges, as discussed in U.S. patent application Ser. No. 13/994,431, which has hereinabove been incorporated herein by reference in its entirety.

In some embodiments, the suitable linker comprises a fluorescent cyanine dye (or "CyDye"), such as Cy3 and Cy3.5. In such embodiments, the CyDye moiety in the linker may be used to provide an additional moiety which can be used to detect the tagged nucleotide, or the CyDye moiety may not be detected and simply provide further structure that enhances the ability to detect the tag moiety attached to the linker. Indeed, the presence of a CyDye moiety in the linker portion of an oligonucleotide tag can enhance the capture and detection of the tagged nucleotide by a nanopore. Example 15 demonstrates how an oligonucleotide tag with a Cy3 moiety in the linker portion enhances the nanopore capture and detection of the tagged nucleotide when bound to a DNA polymerase linked to a nanopore. Accordingly, in some embodiments, the disclosure provides a tagged nucleotide wherein the tag comprises a CyDye moiety, and in some embodiments the CyDye moiety is Cy3. In some embodiments of the tagged nucleotide, the tag comprises an oligonucleotide and a linker, and the linker further comprises a CyDye moiety.

Examples of suitable chemical groups for the position Z include O, S, or BH$_3$. The base can be any base suitable for incorporation into a nucleic acid including adenine, guanine, cytosine, thymine, uracil, or a derivative thereof. Universal bases (i.e., bases that are capable of pairing with more than one of A, C, T, G, and U) are also acceptable in some cases (e.g., 2'deoxyinosine derivatives, nitroindole derivatives).

The number of phosphates (n) is any suitable integer value (e.g., 1, 2, 3, 4, 5, 6, 7, 8, 9, 10, or more) (e.g., a number of phosphates such that the nucleotide may be incorporated into a nucleic acid molecule by a polymerase).

In some instances, all types of tagged nucleotides have the same number of phosphates, but this is not required. In some applications, there is a different tag for each type of nucleotide and the number of phosphates is not necessarily used to distinguish the various tags. However, in some cases more than one type of nucleotide (e.g., A, C, T, G or U) may have the same tag and the ability to distinguish one nucleotide from another is determined at least in part by the number of phosphates (with various types of nucleotides having a different value for n). In some embodiments, the value for n is 1, 2, 3, 4, 5, 6, 7, 8, 9, 10, or greater.

Suitable tags are described below. In some instances, the tag has a charge which is opposite in sign relative to the charge on the rest of the nucleotide. When the tag is attached, the charge on the overall compound may be neutral. Release of the tag may result in two molecules, a charged tag and a charged nucleotide. The charged tag enters a nanopore and is thereby detected in some cases.

Figure 2:
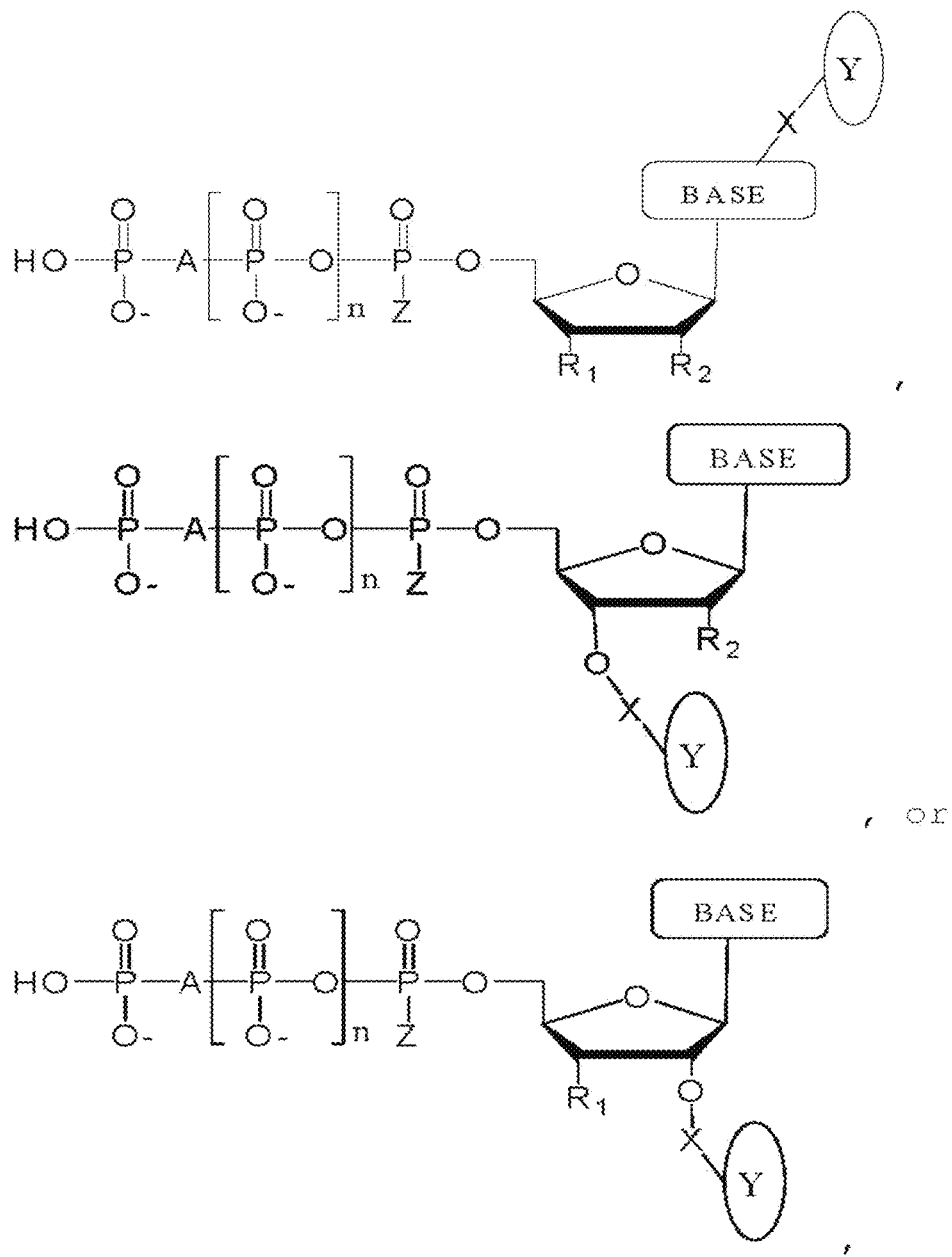
FIG. 2 shows alternate tag locations.

More examples of suitable tagged nucleotides are shown in FIG. 2. The tag may be attached to the sugar moiety, the base moiety, the polyphosphate moiety or any combination thereof. With reference to FIG. 2, Y is a tag and X is a linker (in some cases cleavable). Furthermore, $R_1$, if present, is generally —OH, —OCH$_2$N$_3$ or —O-2-nitrobenzyl, and $R_2$, if present, is generally —H or —OH. Also, Z is generally O, S or BH$_3$, and n is any integer including 1, 2, 3, 4, 5, 6, or 7. In some cases, the A is O, S, CH$_2$, CHF, CFF, or NH.

With continued reference to FIG. 2, a set of 4 distinct tagged nucleotides can be used wherein each type of base on the tagged nucleotide is generally different from the type of base on each of the other three tagged nucleotides, and the type of tag on each tagged nucleotide is generally different from the type of tag on each of the other three tagged nucleotide. Suitable bases include, but are not limited to adenine, guanine, cytosine, uracil or thymine, or a derivative of each thereof. In some cases, the base is one of 7-deazaguanine, 7-deazaadenine or 5-methylcytosine, or non-naturally occurring bases such as nitropyrrole, nitroindole, nebularine, zebularine, benzene, or derivatives thereof (see e.g., FIG. 29).

In cases where $R_1$ is —O—CH$_2$N$_3$, the nucleotide can be used in methods that further comprise treating the incorporated tagged nucleotide so as to remove the —CH$_2$N$_3$ and result in an OH group attached to the 3' position thereby permitting incorporation of a further tagged nucleotide.

In cases where $R_1$ is —O-2-nitrobenzyl, the tagged nucleotide can be used in methods that further comprise treating the incorporated tagged nucleotide so as to remove the 2-nitrobenzyl and result in an OH group attached to the 3' position thereby permitting incorporation of a further tagged nucleotide.

A tag may be any chemical group that is capable of being detected in or with the aid of a nanopore. In some cases, a tag comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an oligonucleotide (of greater length than 6-mer), a polynucleotide an aliphatic acid, an aromatic acid, an alcohol, a thiol group, a cyano group, a nitro group, an alkyl group, an alkenyl group, an alkynyl group, an azido group, or a combination thereof.

It is also contemplated that the tag further comprises appropriate number of lysines or arginines to balance the number of phosphates in the compound.

In some cases, the tag is a polymer. Polyethylene glycol (PEG) is an example of a polymer and has the structure as follows:

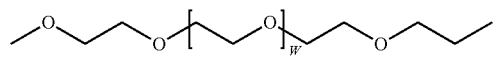

Any number of ethylene glycol units (W) may be used. In some instances, W is an integer between 0 and 100. In some cases, the number of ethylene glycol units is different for each type of nucleotide. In an embodiment, the four types of nucleotides comprise tags having 16, 20, 24 or 36 ethylene glycol units. In some cases, the tag further comprises an additional identifiable moiety, such as a coumarin based dye. In some cases, the polymer is charged. In some instances, the polymer is not charged and the tag is detected in a high concentration of salt (e.g., 3-4 M). In some cases, the polymer is an oligonucleotide comprising ribonucleotides and/or deoxyribonucleotides. In addition, the polymer can be a polypeptide comprising amino-acid subunits.

In some cases, a tag comprises multiple PEG chains. In an example, a tag has the structure as follows:

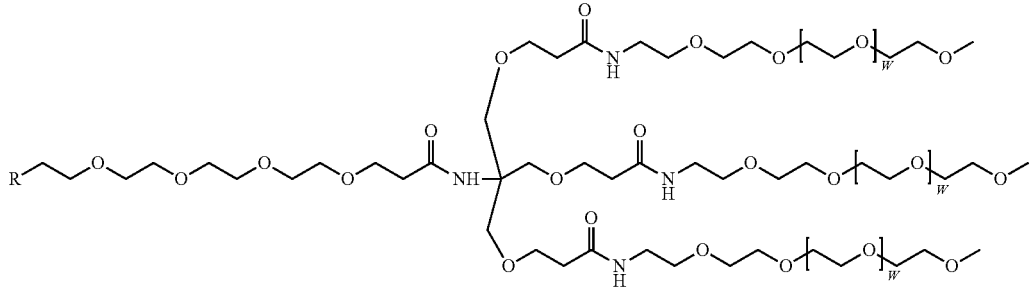

wherein R is NH$_2$, OH, COOH, CHO, SH, or N$_3$, and W is an integer from 0 to 100. See, for example, U.S. patent application Ser. No. 13/994,431, which has hereinabove been incorporated herein by reference in its entirety.

Figure 29:
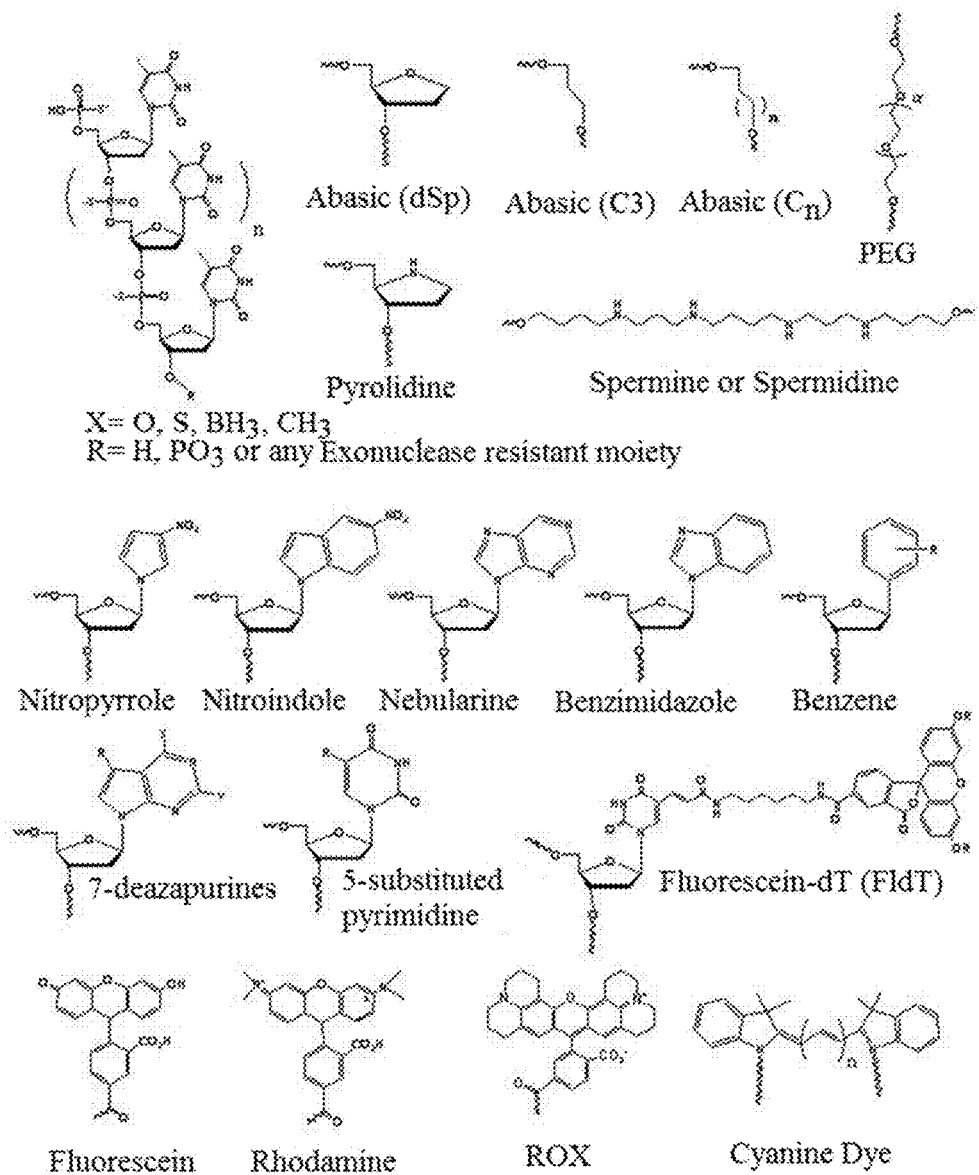
FIG. 29 shows examples of monomers that can be incorporated into oligonucleotides using amidite chemistry.

As noted above, in some embodiments the tag of the tagged nucleotide can itself comprise an oligonucleotide. In some embodiments, the oligonucleotide tag can comprise naturally occurring bases (e.g., A, C, G, T), non-naturally-occurring (or modified) nucleoside bases, or mixtures thereof. Some exemplary non-naturally-occurring (or modified) bases are illustrated in FIG. 29 and include, but are not limited to nitropyrrole, nitroindole, nebularine, zebularine, and benzene, and derivatives thereof. In some embodiments, the oligonucleotide tag can comprise a naturally-occurring phosphodiester inter-nucleotide linkage, or can have non-naturally occurring internucleotide linkages such as phosphotriester, phosphorothioate, methylphosphonate or boronophosphate. In some instances, the inter-nucleotide linkage is a morpholino moiety.

As described further below, oligonucleotide tags can be detected by a nanopore due to their presence in the pore causing a detectable electric current change in the sensor associated with the nanopore. It is not necessary, however, for the oligonucleotide to hybridize. Indeed, hybridization of the oligonucleotide tag to the template sequence could create problems in providing the appropriate current blockade signal necessary for nanopore sequencing. Accordingly, in some embodiments, the oligonucleotide tags can comprise nucleotides with one or more unnatural bases (e.g., such as noted above) or an unnatural sugar moiety (described further below). Such non-naturally occurring bases and sugar moieties do not form hydrogen bonds with natural nucleotides and thus, do not hybridize to the nucleic acid template being sequences.

Figure 32:
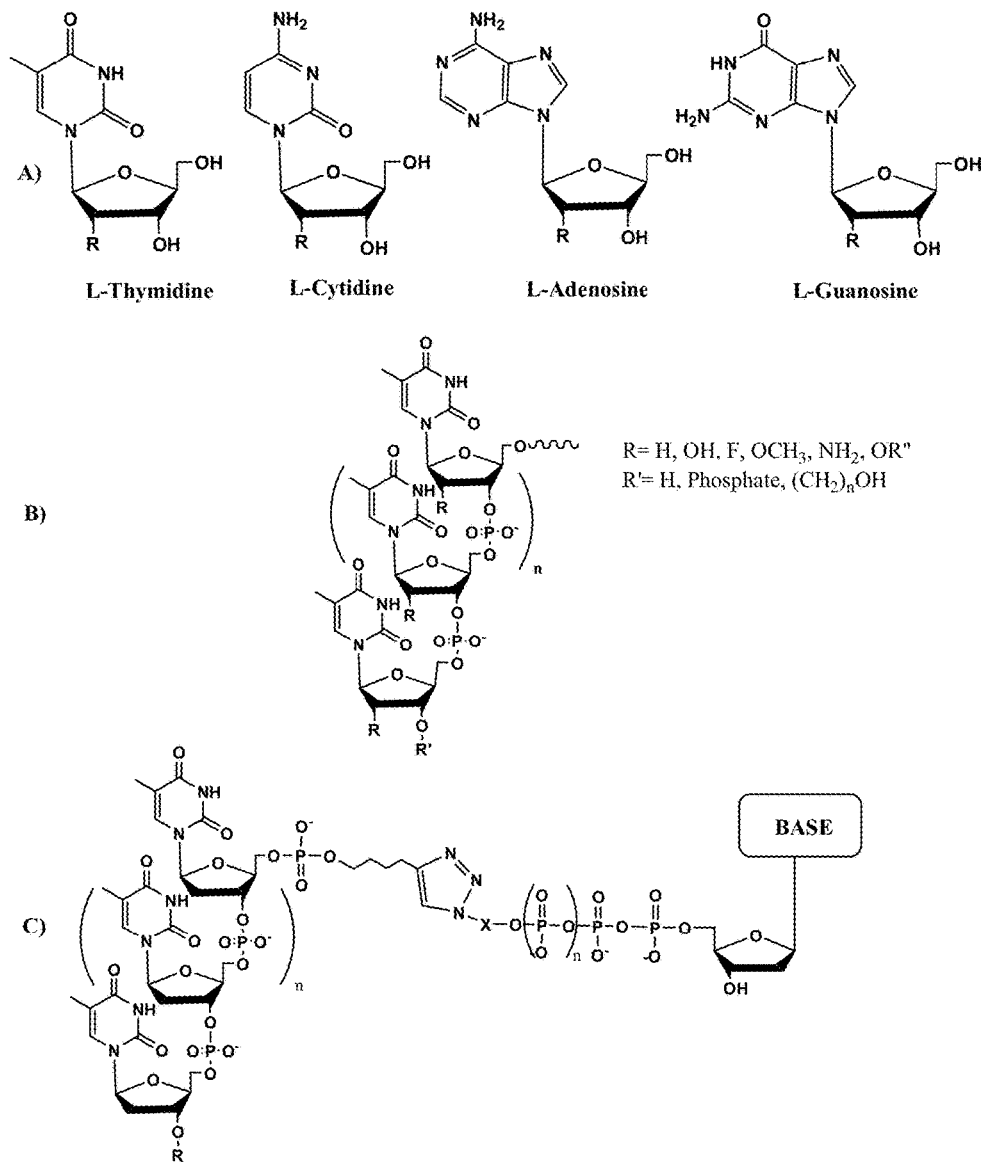
FIG. 32 depicts exemplary L-nucleotides that can be used in the oligonucleotide tags of the present disclosure.

Additionally, in some embodiments the oligonucleotide tag can comprise an L-nucleotide (rather than a D-nucleotide). Exemplary L-nucleosides that can be used in the oligonucleotide tags of the present disclosure are shown in FIG. 32A. L-nucleic acids do not, in general, recognize single-stranded, natural DNA and RNA (see e.g., Asseline et al. (1991) and Garbesi et al. (1993)). It is contemplated that oligonucleotide tags can comprise all L-nucleotides or mixtures of L- and D-nucleotides in ratios such that they do not hybridize with the nucleic acid template being sequenced. Accordingly, the present disclosure provides a tagged nucleotide comprising: (a) a nucleotide polyphosphate moiety having a terminal phosphate; and (b) an oligonucleotide tag comprising an L-nucleotide covalently coupled, directly or with a further linker moiety, to the terminal phosphate through a triazole, a 1,2-diazine, a disulfide, a amide, a hydrazone, a thio-acetamide, or a maleimide-thio adduct.

Figure 33:
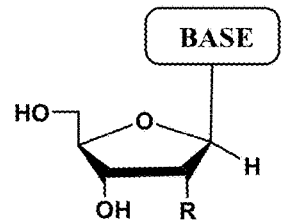
FIG. 33 depicts exemplary α-D-nucleosides, β-D-nucleosides and 2',5-linked nucleotides that can be used in the oligonucleotide tags of the present disclosure.
Figure 33:
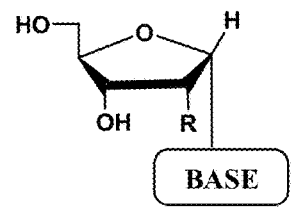
Figure 33:
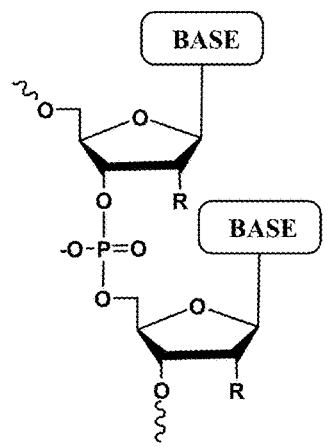
Figure 33:
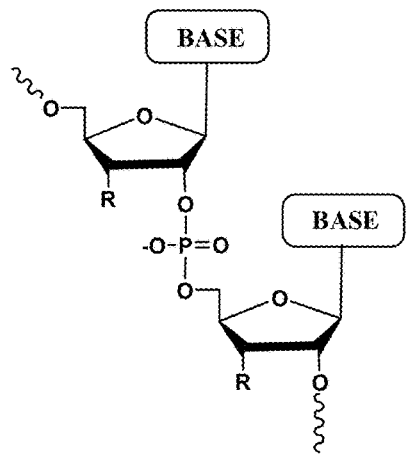

Naturally occurring nucleosides have a β-D configuration with respect to the 1'-position of ribose and the nucleic acid base. In another embodiment, the oligonucleotide tag can comprise an α-D-nucleoside (FIG. 33A). The oligonucleotide-tag may comprise all or a mixture of α-D-nucleotides and β-D-nucleotides in a ratio such that they do not hybridize with the nucleic acid template being sequenced (FIG. 33B). Accordingly, the present disclosure provides a tagged nucleotide, comprising: (a) a nucleotide polyphosphate moiety having a terminal phosphate; and (b) an oligonucleotide tag comprising an α-D-nucleotide covalently coupled, directly or with a further linker moiety, to the terminal phosphate of the nucleotide through a triazole, a 1,2-diazine, a disulfide, an amide, a hydrazone, a thio-acetamide, or a maleimide-thio adduct.

In an another embodiment, the present disclosure provides an oligonucleotide tag comprising an unnatural synthetic nucleoside as described by Kim et al. (2005), Sefah et al. (2014) and Romesberg et al. (*J. Am. Chem. Soc.* 2014 and *Nucleic Acids Research* 2014). The unnatural synthetic nucleosides described in these publications do not form H-bonds with the naturally occurring nucleosides (adenine, guanine, cytosine, thymine, uracil, deazapurines or derivatives thereof) and thus, do not hybridize with natural nucleic acid templates. An oligonucleotide tag comprising such unnatural synthetic nucleosides may be a deoxyribonucleotide or a ribonucleotide and may comprise all unnatural nucleosides or a mixture with some naturally occurring nucleosides.

In another aspect, the present disclosure provides a tagged nucleotide wherein the tag comprises an oligonucleotide with at least one 2',5'-linkage (rather than the naturally occurring 3',5'-linkage) between a pair of nucleotides in the tag. FIG. 33B shows a comparative illustration of 2',5'-linked and a 3',5'-linked oligonucleotide. Such 2',5'-linked oligonucleotides bind selectively to complementary RNA but not to DNA templates (Bhan et al. (1997)). Thus, an oligonucleotide tag comprising of 2',5'-linked oligonucleotide would not bind to the nucleic acid template being sequenced. It is contemplated that an oligonucleotide tag can comprise only 2',5'-linked nucleotides or can comprise a mixture of 2',5'-linked and 3',5'-linked nucleotides. Accordingly, the present disclosure provides an oligonucleotide tag comprising: (a) a nucleotide polyphosphate moiety having a terminal phosphate; and (b) a tag comprising a chain of 1-100 2',5'-linked nucleotide units that is covalently coupled, directly or with a further linker moiety, to the terminal phosphate of the nucleotide by a triazole, a 1,2-diazine, a amide, a hydrazone, a thio-acetamide, or a maleimide-thioadduct.

Figure 34:
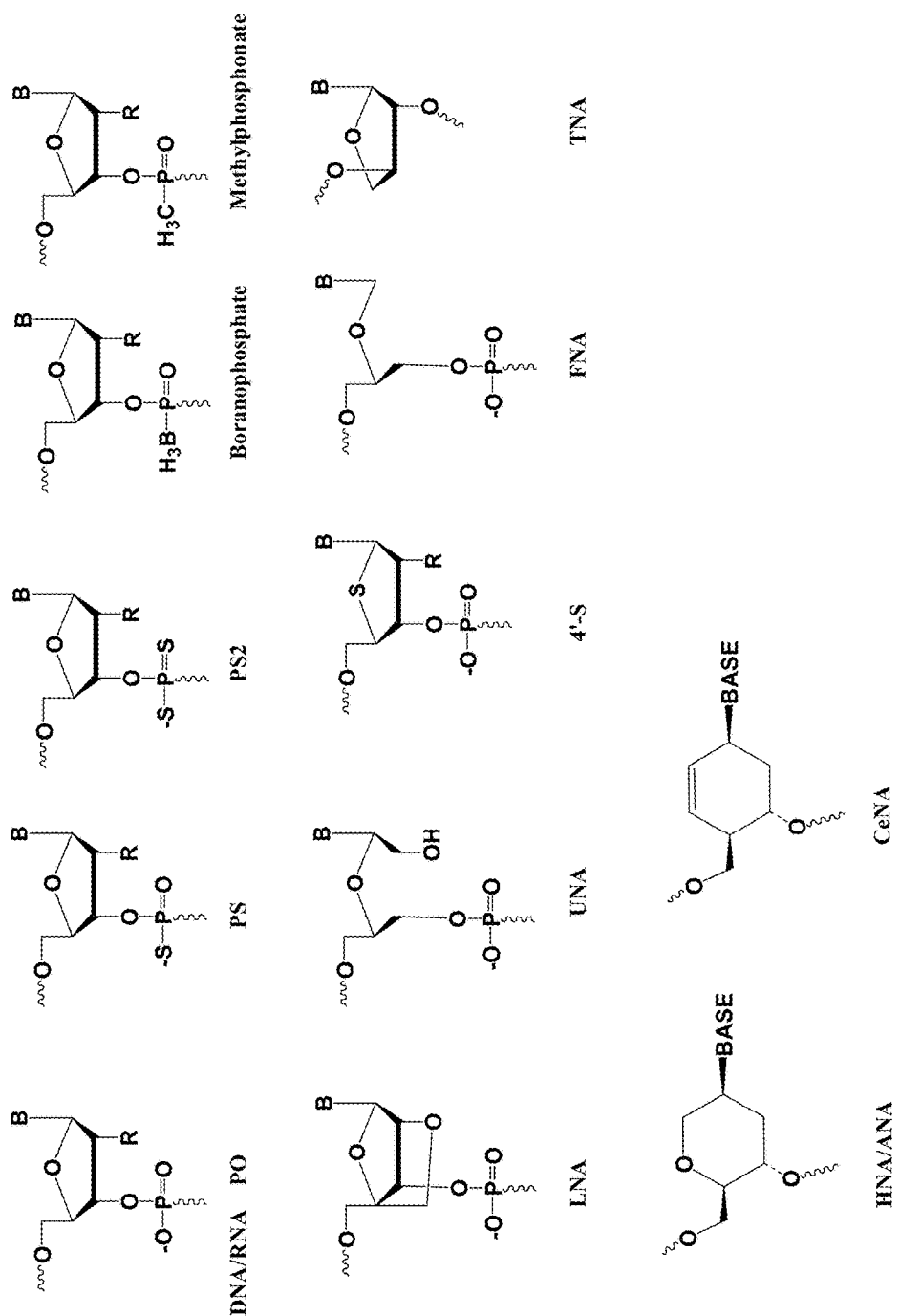
FIG. 34 depicts exemplary unnatural internucleotide linkages and non-natural sugars that can be used in the oligonucleotide tags of the present disclosure.

In another aspect, the present disclosure provides a tagged nucleotide wherein the tag comprises an oligonucleotide with at least one modified sugar and/or phosphate moiety. Exemplary modified sugar and/or phosphate moieties that can be used in the oligonucleotide tags of the present disclosure are depicted in FIG. 34. It is contemplated that an oligonucleotide tag can comprise only modified sugar and/or phosphate moieties or can comprise a mixture of modified sugar and/or phosphate moieties and naturally occurring (e.g., ribose) nucleotides in the oligonucleotide tag. Accordingly, the present disclosure provides an oligonucleotide tag comprising: (a) a nucleotide polyphosphate moiety having a terminal phosphate; and (b) a tag comprising a chain of 1-100 nucleoside units comprising a modified sugar and/or phosphate moiety that is covalently coupled, directly or with a further linker moiety, to the terminal phosphate of the nucleotide by a triazole, a 1,2-diazine, a disulfide, an amide, a hydrazone, a thio-acetamide, or a maleimide-thioadduct.

In the tagged nucleotide embodiments provided by the present disclosure it is contemplated that a natural or synthetic oligonucleotide tag can be covalently coupled through either its 5' or 3' end, directly or through a linker moiety, to a terminal phosphate of the nucleotide. In some embodiments, the oligonucleotide tag is covalently coupled through its 5' end, directly or through a linker moiety, to a terminal phosphate of the nucleotide. In such embodiments, it is contemplated that the 3'-hydroxyl at the other end of the oligonucleotide tag is modified so as to protect the oligonucleotide from potential exonuclease degradation. In some embodiments, the 3'-hydroxyl terminus of the oligonucleotide tag is protected from exonuclease activity by chemical modification. Exemplary chemical modifications of the 3'-hydroxyl terminus can include phosphorylation, or covalent coupling with $C_3$-alkyl to $C_{12}$-alkyl spacers having terminal hydroxyl groups.

Figure 3:
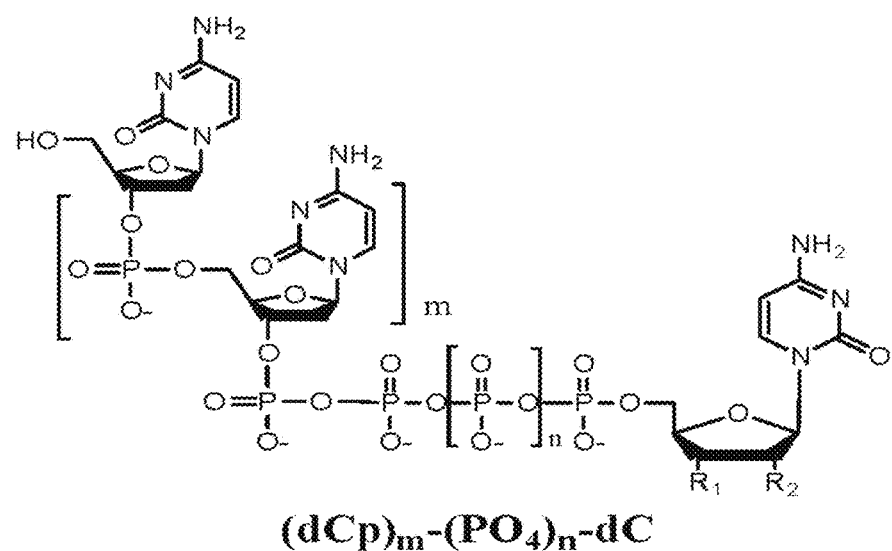
FIG. 3 shows an example of tagged nucleotides.
Figure 3:
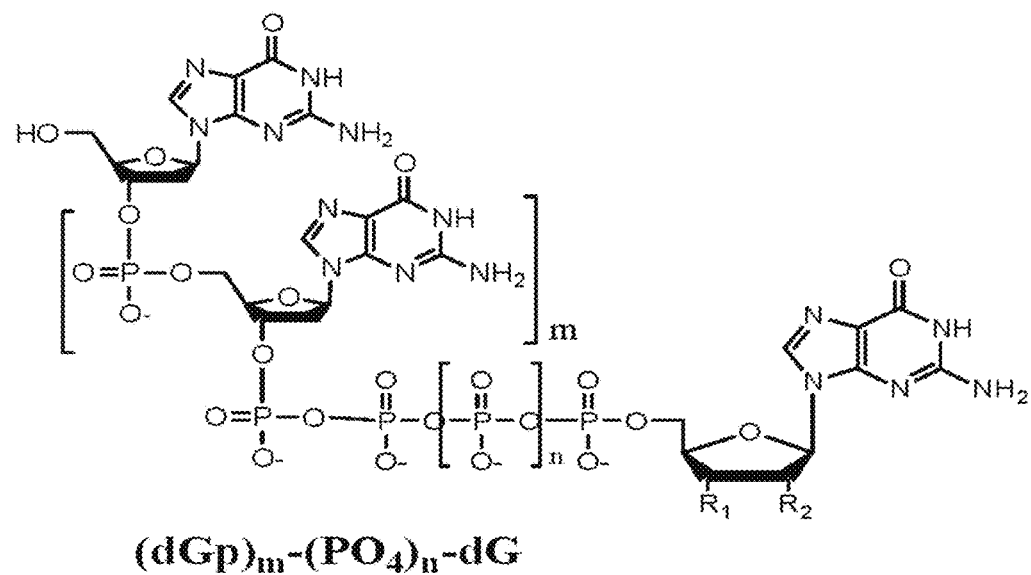
Figure 4:
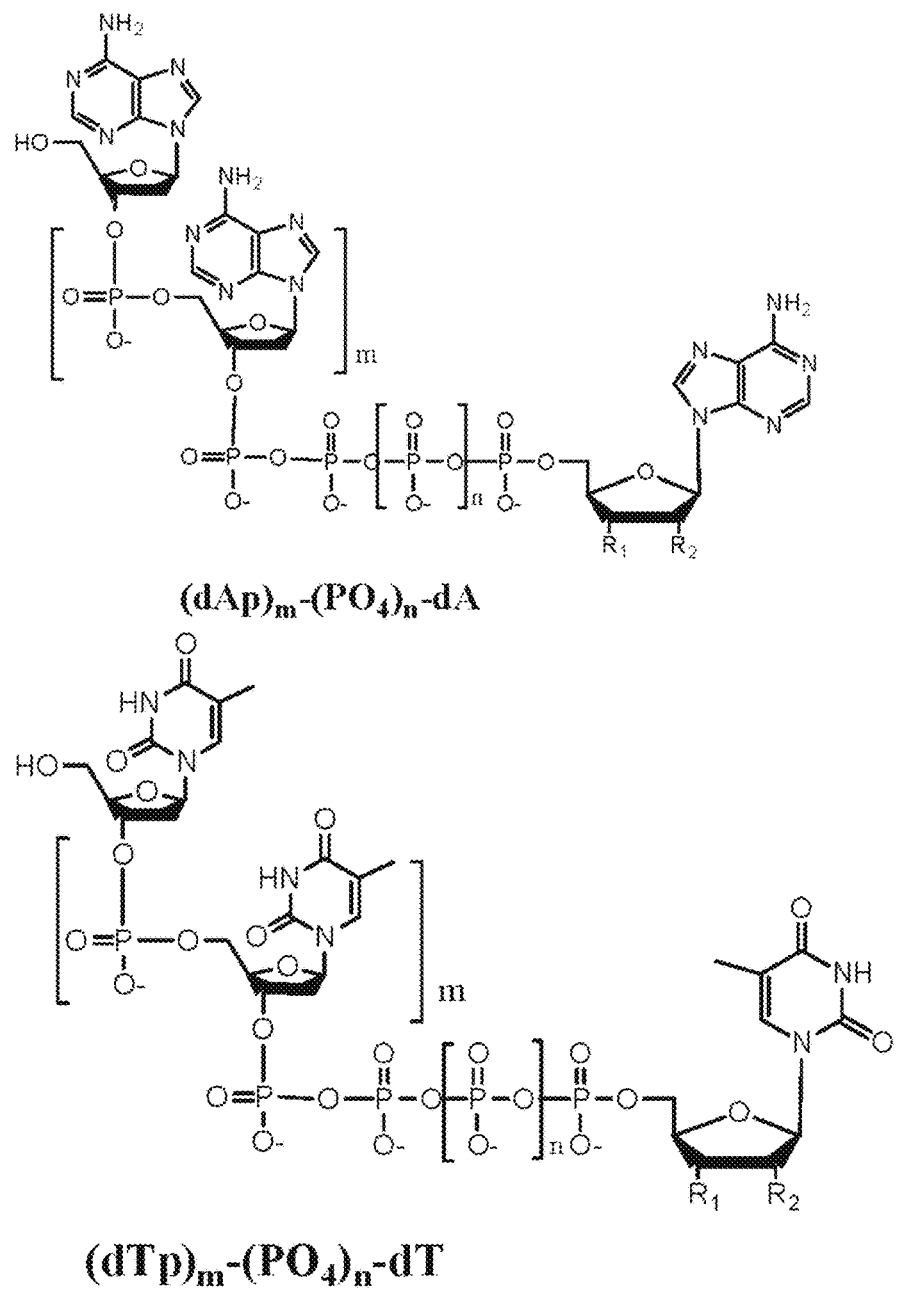
FIG. 4 shows an example of tagged nucleotides.

In some examples, a tag is chosen from the molecules (dCp)m, (dGp)m, (dAp)m, and (dTp)m or a combination of one or more units of (dCp), dGp), (dAp) and (dTp). FIG. 3 and FIG. 4 show these molecules attached to a nucleotide. Here, 'm' is, independently, an integer from 0 to 100, and wherein when m is 0 the terminal phosphate of the dNPP is bonded directly to the 3' O atom of the nucleoside shown on the left hand side of the structure. In some cases, the value of n is different for each type of base.

In some instances, a tag is a hydrocarbyl, substituted or unsubstituted, such as an alkyl, alkenyl, alkynyl, and having a mass of 3000 Daltons or less.

As used herein, the term "alkyl" includes both branched and straight-chain saturated aliphatic hydrocarbon groups having the specified number of carbon atoms and may be unsubstituted or substituted. As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom.

Figure 5:
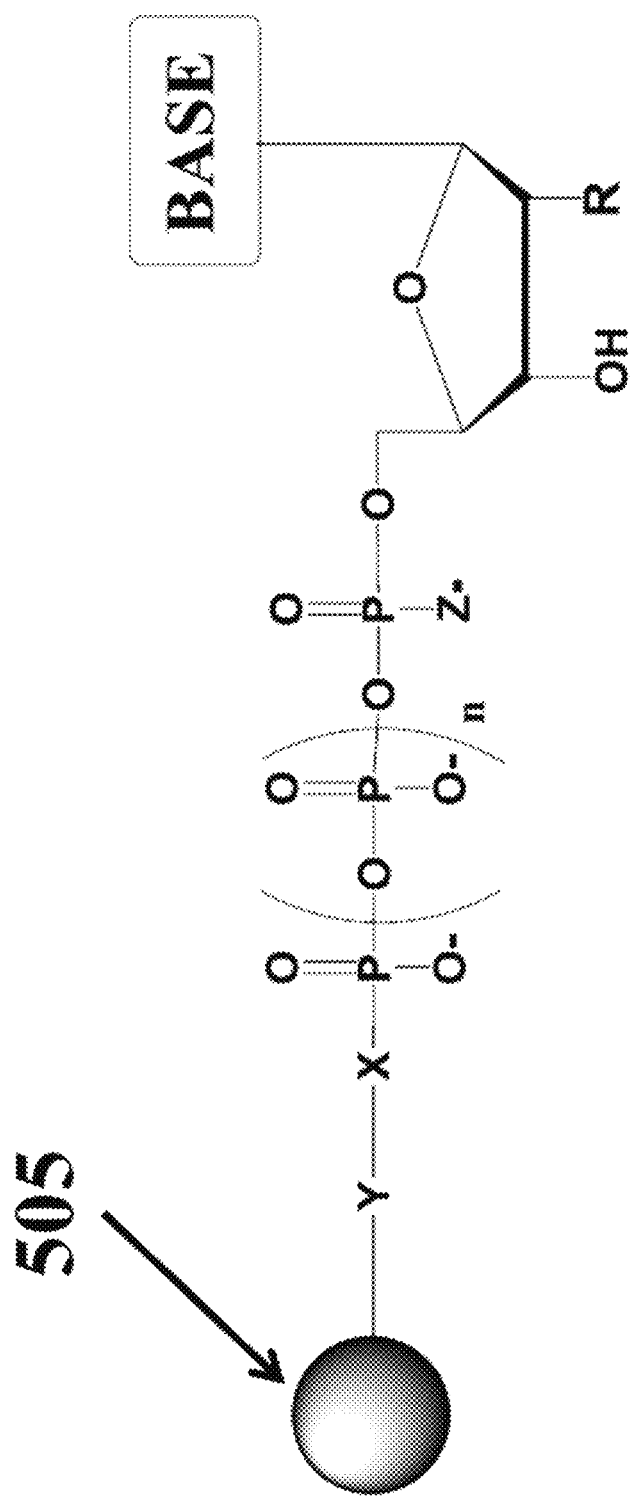
FIG. 5 shows a structure of a tagged nucleotide. Tag 505 is attached to the terminal phosphate.

FIG. 5 shows a nucleoside with a tag 505 attached to the terminal phosphate. As shown here, the base can be any base (e.g., A, T, G, C, U, or derivatives thereof), R can be any chemical group (e.g., H, OH), n can be any integer (e.g., 1, 2, 3, 4, 5, 6, 7, 8, 9, 10, or more), X can be any chemical group (e.g., O, NH, S) and Y can be any functional group which makes a covalent bond with X and is attached to the tag. Examples of tags include, but are not limited to oligonucleotides of any size (e.g., with 2-100 bases, 5-50 bases, or 2-40 bases). In some cases, the oligonucleotide tag has nitropyrrole, nitroindole, nebularine, zebularine, benzene, or derivatives thereof as a homopolymer or heteropolymer. In some cases, the tag has a phospotriester, phosphodiester, phosphoramidate, phosphorothioate, methylphosphonate or boronophosphate internucleotide linkages. In some instances, the internucleotide linkage is a morpholino moiety.

Figure 6:
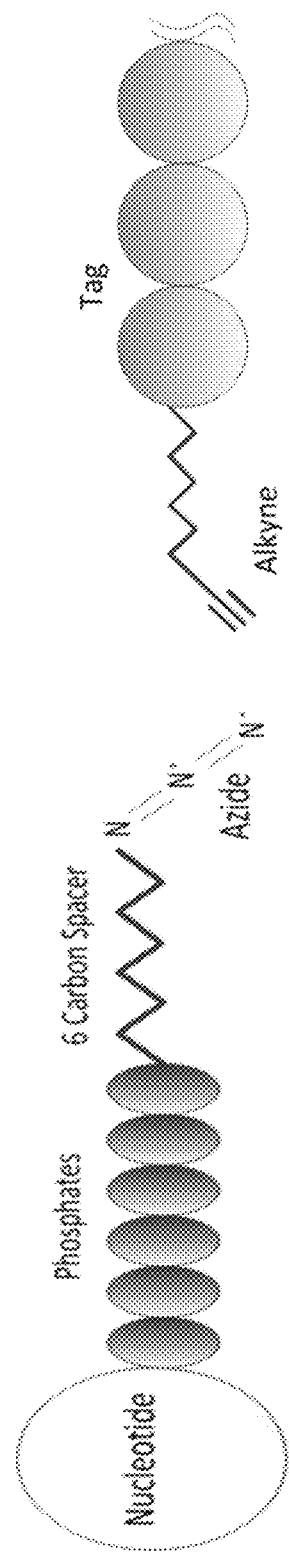
FIG. 6 shows a nucleotide (left) and a tag (right) capable of being joined by click chemistry.

In some embodiments, the tag is attached to the nucleotide using azide-alkyne Huisgen cycloaddition, also known as "click chemistry". For example, FIG. 6 shows a nucleotide having 6 phosphates with a 6 carbon spacer and a reactive azide group attached to the terminal phosphate (left) being reacted with a tag having a 6 carbon spacer and a reactive alkyne group (right) using click chemistry. As described elsewhere herein, FIG. 21, schemes (A), (B), and (C) illustrates three exemplary click chemistry reactions for conjugating two compounds (A and B). Any one of these three exemplary click reactions can be adapted for use in conjugating a tag to a nucleotide and thereby make the tagged nucleotides of the present disclosure. Specific illustrations of the use of such click reactions are provided in the Examples.

In an aspect, a tagged nucleotide is formed by providing a nucleotide comprising a poly-phosphate tail comprising a terminal phosphate. The terminal phosphate of the nucleotide can be covalently connected to an alkane or similar linker to an azide. The tag can be covalently bound to the nucleotide terminal phosphate-azide using the "click" reaction to form a triazole. The triazole can be formed by a reaction between an azide and an alkyne. In some embodiments, the poly-phosphate tail comprises at least 3 phosphates, at least 4 phosphates, at least 5 phosphates, at least 6 phosphates, or at least 7 phosphates. In some embodiments, the poly-phosphate moiety comprises from 4 to 6 phosphates. In some embodiments, the poly-phosphate moiety comprises at least 6 phosphates. The tag can comprise nucleotides, oligonucleotides, polyethylene glycol (PEG), oligo-saccharides, carbohydrates, peptide nucleic acids (PNA), vinyl polymers, other water-soluble polymers, peptides, or any combination thereof.

In some cases, the triazole has the structure:

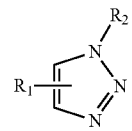

wherein $R_1$ comprises the tag, and $R_2$ comprises the nucleotide; or wherein $R_1$ comprises the nucleotide, and $R_2$ comprises the tag.

In some cases, the triazole has the structure:

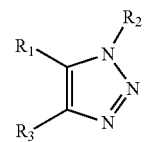

wherein $R_1$ and $R_3$ combine to form a cyclic moiety; and wherein $R_1$ and $R_3$ combined comprise the tag, and $R_2$ comprises the nucleotide; or wherein $R_1$ and $R_3$ combined comprise the nucleotide, and $R_2$ comprises the tag.

Also provided herein is a method for making a tagged nucleotide, comprising providing a nucleotide comprising a poly-phosphate tail, where the poly-phosphate tail comprises a terminal phosphate. The terminal phosphate can comprise either an azide group or an alkyne group. The method includes providing a tag molecule comprising either an azide group or an alkyne group, where the nucleotide and the tag molecule do not each comprise an azide group, and where the nucleotide and the tag molecule do not each comprise an alkyne group. The method can also include reacting the azide group with the alkyne group to link the nucleotide to the tag molecule. In some cases, the reaction is facilitated by a catalyst comprising salts of copper, ruthenium, silver, or any combination thereof.

In some cases, the reaction does not require a catalyst. A catalyst may not be needed when the alkyne is a cyclooctyne, (e.g., a dibenzylcyclooctyne).

In some cases, tags can be attached to the terminal phosphate by (a) contacting a nucleoside triphosphate with dicyclohexylcarbodiimide/dimethylformamide under conditions permitting production of a cyclic trimetaphosphate; (b) contacting the product resulting from operation (a) with a nucleophile so as to form an —OH or —NR, functionalized compound; and (c) reacting the product of operation (b) with a tag having a —COR group attached thereto under conditions permitting the tag to bond indirectly to a terminal phosphate thereby forming the tagged nucleotide.

In some cases, the nucleophile is $H_2N—R—OH$, $H_2N—R—NH_2$, $R'S—R—OH$, $R'S—R—NH_2$, or

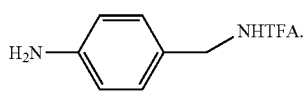

In some instances, the method comprises, in operation b), contacting the product resulting from operation a) with a compound having the structure:

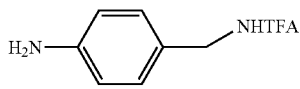

and subsequently or concurrently contacting the product with NH$_4$OH so as to form a compound having the structure:

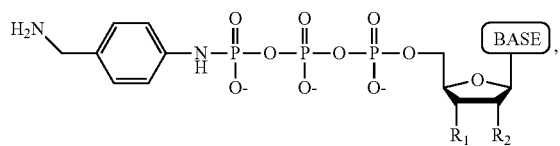

The product of operation b) may then be reacted with a tag having a —COR group attached thereto under conditions permitting the tag to bond indirectly to a terminal phosphate thereby forming the tagged nucleotide having the structure:

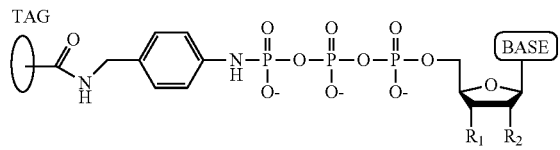

wherein $R_1$ is OH, wherein $R_2$ is H or OH, wherein the base is adenine, guanine, cytosine, thymine, uracil, a 7-deazapurine or a 5-methylpyrimidine.

Connection of the nucleotide polyphosphate to the tag can also be achieved by the formation of a disulfide (forming a readily cleavable connection), formation of an amide, formation of an ester, by alkylation (e.g., using a substituted iodoacetamide reagent) or forming adducts using aldehydes and amines or hydrazines. Numerous conjugation chemistries can be found in Hermanson (2008), which is incorporated herein by reference in its entirety.

Specific examples of reactive groups on the terminal phosphates or the Oligonucleotide Tags and groups with which groups can react are provided in Table 1. These reactive groups with which they can react can be present either on the linker or on the tag.

TABLE 1

Possible Reactive Substituents and Functional Groups Reactive Therewith

| Reactive Groups | Functional Groups |
| --- | --- |
| Succinimidyl esters | Primary amino, secondary amino |
| Anhydrides, acid halides | Amino and Hydroxyl groups |
| Carboxyl | Amino, Hydroxy, Thiols |
| Aldehyde, Isothiocyanate & Isocyanates | Amino groups |
| Vinyl sulphone & Dichlorotriazine | Amino groups |

TABLE 1-continued

Possible Reactive Substituents and Functional Groups Reactive Therewith

| Reactive Groups | Functional Groups |
| --- | --- |
| Haloacetamides | Thiols, Imidazoles |
| Maleimides | Thiols, Hydroxy, Amino |
| Thiols | Thiols, Maleimide, Haloacetamide |
| Phosphoramidites, Activated Phosphates | Hydroxy, Amino, Thiol groups |
| Azide | Alkyne |
| Tetrazine | Dienes |

Figure 7:
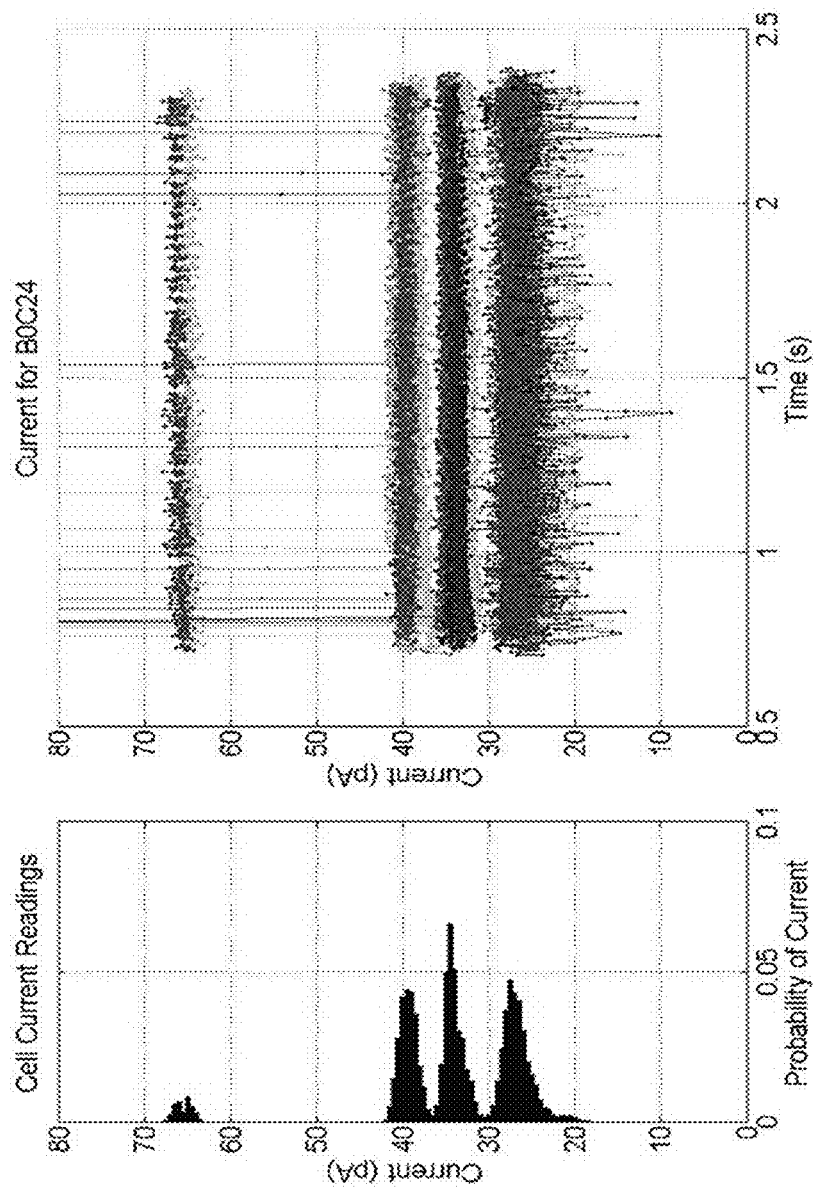
FIG. 7 shows an example of the cell current readings for four cleaved tags.

Another aspect of the present disclosure provides a method for sequencing a nucleic acid sample with the aid of a nanopore in a membrane adjacent to a sensing electrode. The method comprises providing tagged nucleotides having a tag linked to a terminal phosphate by a triazole into a reaction chamber comprising the nanopore, where an individual tagged nucleotide of the tagged nucleotides contains a tag coupled to a nucleotide that is detectable with the aid of the nanopore. A polymerization reaction is carried out with the aid of a polymerase, thereby incorporating an individual tagged nucleotide of the tagged nucleotides into a growing strand complementary to a single stranded nucleic acid molecule from the nucleic acid sample. Using the nanopore, a tag associated with the individual tagged nucleotide is detected upon forming a ternary complex at the polymerase active which allows the tag to enter and become positioned in the adjacent pore, and/or subsequent to the polymerase incorporating the individual tagged nucleotide into the growing strand, whereby the tag is detected with the aid of the nanopore when the tag has been cleaved from the nucleotide. FIG. 7 shows cell current readings for four different tags that are attached using click chemistry. The four different tags are individually resolvable and can correspond to A residues, T residues, G residues and C residues.

Methods for Molecular Sensing and/or Identification

The present disclosure provides methods for molecular sensing and/or identification. Such methods may be used to detect various types of biological species, such as nucleic acids, proteins and antibodies. In some embodiments, methods for molecular identification are used to sequence nucleic acid molecules.

In an example, a method for sequencing nucleic acids includes retrieving a biological sample having the nucleic acid to be sequenced, extracting or otherwise isolating the nucleic acid sample from the biological sample, and in some cases preparing the nucleic acid sample for sequencing.

Figure 8:
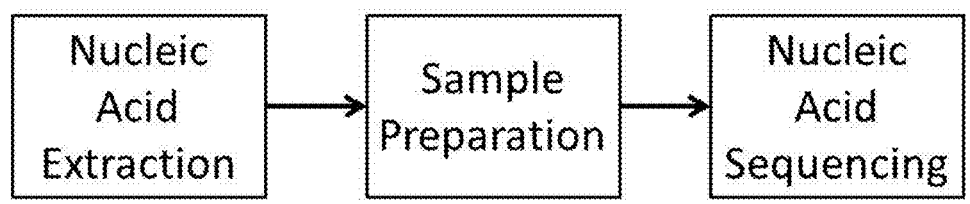
FIG. 8 schematically shows the operations of the sequencing method described herein.

FIG. 8 schematically illustrates a method for sequencing a nucleic acid sample. The method comprises isolating the nucleic acid molecule from a biological sample (e.g., tissue sample, fluid sample), and preparing the nucleic acid sample for sequencing. In some instances, the nucleic acid sample is extracted from a cell. Some exemplary techniques for extracting nucleic acids are using lysozyme, sonication, extraction, high pressures or any combination thereof. The nucleic acid is cell-free nucleic acid in some cases and does not require extraction from a cell.

In some cases, a nucleic acid sample may be prepared for sequencing by a process that involves removing proteins, cell wall debris and other components from the nucleic acid sample. There are many commercial products available for accomplishing this, such as, for example, spin columns. Ethanol precipitation and centrifugation may also be used.

The nucleic acid sample may be partitioned (or fractured) into a plurality of fragments, which may facilitate nucleic acid sequencing, such as with the aid of a device that includes a plurality of nanopores in an array. However, fracturing the nucleic acid molecule(s) to be sequenced may not be necessary.

In some instances, long sequences are determined (i.e., "shotgun sequencing" methods may not be required). Any suitable length of nucleic acid sequence may be determined. For instance, at least about 400, about 500, about 600, about 700, about 800, about 800, about 1000, about 1500, about 2000, about 2500, about 3000, about 3500, about 4000, about 4500, about 5000, about 6000, about 7000, about 8000, about 9000, about 10000, about 20000, about 40000, about 60000, about 80000, or about 100000, and the like bases may be sequenced. In some instances, at least 400, at least 500, at least 600, at least 700, at least 800, at least 800, at least 1000, at least 1500, at least 2000, at least 2500, at least 3000, at least 3500, at least 4000, at least 4500, at least 5000, at least 6000, at least 7000, at least 8000, at least 9000, at least 10000, at least 20000, at least 40000, at least 60000, at least 80000, at least 100000, and the like bases are sequenced. In some instances the sequenced bases are contiguous. In some cases, the nucleic acid sample may be partitioned prior to sequencing.

A tag may be released in any manner. A tag can be released during or subsequent to the incorporation of a nucleotide into a polynucleotide chain. In some cases, the tag is attached to the polyphosphate moiety of a nucleotide (e.g., FIG. 15) and incorporation of the nucleotide into a nucleic acid molecule results in release of a polyphosphate having the tag attached thereto (e.g., separating it from the rest of the nucleotide and growing nucleic acid strand). The incorporation may be catalyzed by at least one polymerase, which can be attached to the nanopore. In some instances, at least one phosphatase enzyme is also attached to the pore. The phosphatase enzyme may cleave the phosphates from the released polyphosphate tag. In some cases, the phosphatase enzymes are positioned such that polyphosphate product of the polymerase interacts with the phosphatase enzymes prior to the tag entering the pore.

In some cases, the tag is not attached to polyphosphate (see, e.g., FIG. 2). In these cases, the tag is attached by a linker (X), which can be cleavable. Methods for production of cleavably capped and/or cleavably linked nucleotides are disclosed in U.S. Pat. No. 6,664,079, which is entirely incorporated herein by reference. The linker need not be cleavable.

The linker may be any suitable linker and can be cleaved in any suitable manner. The linkers may be photocleavable. In an embodiment UV light is used to photochemically cleave the photochemically cleavable linkers and moieties. In an embodiment, the photocleavable linker is a 2-nitrobenzyl moiety.

The —$CH_2N_3$ group may be treated with TCEP (tris(2-carboxyethyl)phosphine) so as to remove it from the 3'-O atom of a nucleotide, thereby creating a 3' OH group.

In some instances, a polymerase draws from a pool of tagged nucleotides comprising a plurality of different bases (e.g., A, C, G, T, and/or U). It is also possible to contact the polymerase with the various types of tagged nucleotides comprising different bases individually and serially. In this case, it may not be necessary that each type of nucleotide have a unique tag since only one nucleotide is present during any given reaction.

Figure 15:
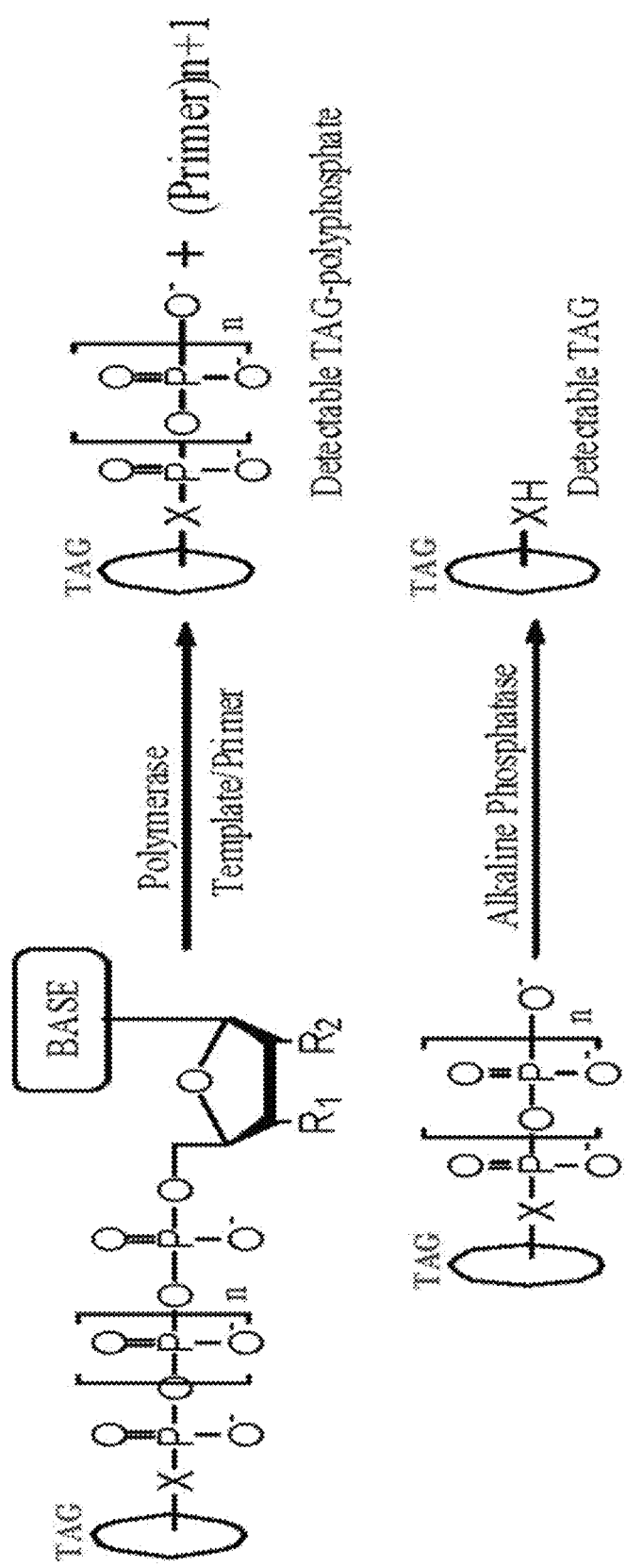
FIG. 15 shows detectable TAG-polyphosphate and detectable TAG.

FIG. 15 shows that incorporation of the tagged nucleotide into a nucleic acid molecule (e.g., using a polymerase to extend a primer base paired to a template) can release a detectable TAG-polyphosphate in some embodiments. In some cases, the TAG-polyphosphate is detected as it passes through the nanopore.

In some cases, the method distinguishes the nucleotide based on the number of phosphates comprising the polyphosphate (e.g., even when the TAGs are identical). Nevertheless, each type of nucleotide can have a unique tag.

With reference to FIG. 15, the TAG-polyphosphate compound may be treated with phosphatase (e.g., alkaline phosphatase) before passing the tag into and/or through a nanopore and measuring the ionic current.

Tags may flow through a nanopore after they are released from the nucleotide. In some instances, a voltage is applied to position the tags in and pull the tags through the nanopore. At least about 85%, at least 90%, at least 95%, at least 99%, at least 99.9 or at least 99.99% of the released tags may enter into, become positioned in, and/or translocate through the nanopore.

In some instances, the tags reside in the nanopore for a period of time where they are detected. In some instances, a voltage is applied to pull the tags into the nanopore, detect the tags, or any combination thereof. The tags can be released upon nucleotide incorporation events.

In some embodiments, the nanopore current change event is monitored and detected while the tag is still attached to the tagged nucleotide rather than when the tag subsequently is released from the nucleotide and passes through the nanopore channel. In such embodiments, the tag is detected while the tagged nucleotide is in a ternary complex at the polymerase active site with its complementary template nucleotide, i.e., prior to nucleotide incorporation and phosphoryl transfer. In such embodiments, the long "tail" of the tag becomes positioned in (or "captured by") the pore of the adjacent nanopore during formation of the ternary complex and results in a change in the current level through the nanopore (i.e., a current blockade event). Detection of the tag while attached in the ternary complex can be facilitated by the use of polymerases and reaction conditions (e.g., pH, metal salts, etc.) that slow the rate of nucleotide incorporation such that it is slower than the rate of tag capture and current blockade measurement at the nanopore. Additionally, appropriate covalent tethering of the polymerase to the nanopore can result in rapid tag capture on the order of microseconds.

The tag may be detected in the nanopore (at least in part) because of its charge. In some instances, the tag compound is an alternatively charged compound which has a first net charge and, after a chemical, physical or biological reaction, a different Second net charge. In some instance, the magnitude of the charge on the tag is the same as the magnitude of the charge on the rest of the compound. In an embodiment, the tag has a positive charge and removal of the tag changes the charge of the compound.

In some cases, as the tag enters, becomes positioned in, passes into and/or through the nanopore, it may generate an electronic change. In some cases the electronic change is a change in current amplitude, a change in conductance of the nanopore, or any combination thereof.

The nanopore may be biological or synthetic or a hybrid nanopore. It is also contemplated that the pore is proteinaceous, for example wherein the pore is an α-hemolysin protein. An example of a synthetic nanopore is a solid-state pore or graphene.

In some cases, polymerase enzymes and/or phosphatase enzymes are attached to the nanopore. A variety of techniques for preparing fusion proteins or protein conjugates may be employed. Fusion proteins or disulfide crosslinks are examples of methods for attaching to a proteinaceous nanopore. In the case of a solid state nanopore, the attachment to the surface near the nanopore may be via biotin-streptavidin linkages. In an example the DNA polymerase is attached to a solid surface via gold surface modified with an alkanethiol self-assembled monolayer functionalized with amino groups, wherein the amino groups are modified to NHS esters for attachment to amino groups on the DNA polymerase. The method may be performed at any suitable temperature. In some embodiments, the temperature is between 4° C. and 10° C. In some embodiments, the temperature is ambient temperature. The method may be performed in any suitable solution and/or buffer. In some instances, the buffer is 300 mM KCl buffered to pH 7.0 to 8.0 with 20 mM HEPES. In some embodiments, the buffer does not comprise divalent cations. In some cases, the method is unaffected by the presence of divalent cations.

In another embodiment, a "SpyCatcher" approach may be used to attach a polymerase to a nanopore protein. In such an approach, two fragments of the collagen adhesion domain (CnaB2) of the *Streptococcus pyogenes* fibronectin-binding protein FbaB recognize each other and subsequently generate a peptide bond between the ε-amino group of a lysine in one fragment (i.e., the "SpyCatcher") and the carboxyl side group of an aspartic acid in the other fragment (i.e., the "SpyTag"). See e.g., Zakeri and Howarth (2010). JACS 132:4526-7. Accordingly, in some embodiments, a DNA polymerase can be attached to a nanopore by attaching a SpyTag to an aspartic acid residue of a pore protein monomer (e.g., α-hemolysin), attaching a SpyCatcher on the N-terminus of a DNA polymerase (e.g., Phi29 or Bst2.0 DNA polymerase), and allowing the covalent peptide linkage to form via the SpyTag and the SpyCatcher.

In another embodiment, a covalent conjugate of a polymerase and a nanopore protein can be prepared using an inverse electron demand Diels-Alder (IEDDA) reaction as described in U.S. Provisional Application No. 62/130,326, which is hereby incorporated by reference. In such an embodiment, the conjugate is prepared by attaching a linker comprising trans-cyclooctene (TCO) group to a monomer of nanopore forming protein (e.g., α-hemolysin) and attaching a linker comprising a 6-methyl-tetrazine (6-Me-TZ) group to a polymerase (e.g., Bst2.0 DNA polymerase). Upon mixing under mild aqueous conditions, the 6-Me-TZ modified polymerase and the TCO-modified nanopore rapidly (1 h) and nearly quantitatively form a covalent linkage that provides a conjugate of a polymerase and nanopore protein that can be used in nanopore sensing applications.

In some cases, current may be measured at different applied voltages. In order to accomplish this, a desired potential may be applied to the electrode, and the applied potential may be subsequently maintained throughout the measurement. In an implementation, an op-amp integrator topology may be used for this purpose as described herein. The integrator maintains the voltage potential at the electrode by means of capacitive feedback.

A voltage potential "$V_{luquid}$" may be applied to the chamber which provides a common electrical potential (e.g., 350 mV) for all of the cells on the chip. The integrator circuit may initialize the electrode (which is electrically the top plate of the integrating capacitor) to a potential greater than the common liquid potential. For example, biasing at 450 mV may give a positive 100 mV potential between electrode and liquid. This positive voltage potential may cause a current to flow from the electrode to the liquid chamber contact. In this instance, the carriers are: (a) $K^+$ ions which flow through the pore from the electrode (trans) side of the bilayer to the liquid reservoir (cis) side of the bilayer and (b) chlorine (Cl–) ions on the trans side which reacts with the silver electrode according to the following electro-chemical reaction: $Ag+Cl^- \rightarrow AgCl+e^-$.

In some cases, $K^+$ flows out of the enclosed cell (from trans to cis side of bilayer) while $Cl^-$ is converted to silver chloride. The electrode side of the bilayer may become desalinated as a result of the current flow. In some cases, a silver/silver-chloride liquid spongy material or matrix may serve as a reservoir to supply $Cl^-$ ions in the reverse reaction which occur at the electrical chamber contact to complete the circuit.

In some cases, electrons ultimately flow onto the top side of the integrating capacitor which creates the electrical current that is measured. The electrochemical reaction converts silver to silver chloride and current will continue to flow only as long as there is available silver to be converted. The limited supply of silver leads to a current dependent electrode life in some cases. In some embodiments, electrode materials that are not depleted (e.g., platinum) are used.

Devices and Systems for Molecular Sensing and/or Identification

The present disclosure provides systems for molecular sensing and/or identification. Such systems may be used to detect various types of biological species, such as nucleic acids, proteins and antibodies. In some embodiments, systems for molecular sensing and/or identification are used to sequence nucleic acid molecules.

A system for nucleic acid sequencing can include a nanopore formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide).

In some cases, as a nucleic acid or tag flows through or adjacent to the nanopore, the sensing circuit detects an electrical signal associated with the nucleic acid or tag. The nucleic acid may be a subunit of a larger strand. The tag may be a byproduct of a nucleotide incorporation event or other interaction between a tagged nucleotide and the nanopore or a species adjacent to the nanopore, such as an enzyme that may hold a tagged nucleotide such that the tag enters or becomes positioned in the pore, and then cleave the tag from the nucleotide upon incorporation of the nucleotide into the nucleic acid extension product. A detected signal may be collected and stored in a memory location, and later used to construct a sequence of the nucleic acid. The collected signal may be processed to account for any abnormalities in the detected signal, such as errors.

Figure 9A:
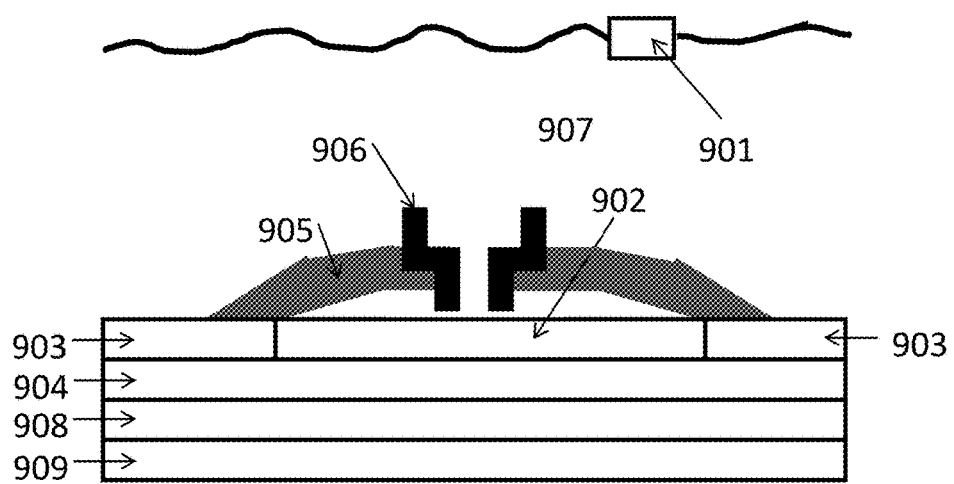
FIG. 9A, FIG. 9B and FIG. 9C show examples of nanopore detectors, where FIG. 9A has the nanopore disposed upon the electrode, FIG. 9B has the nanopore inserted in a membrane over a well and FIG. 9C has the nanopore over a protruding electrode.

FIG. 9 shows an examples of a nanopore detector (or sensor) having temperature control, as may be prepared according to methods described in U.S. Patent Application Publication Nos. 2011/0193570 A1, 2013/0244340 A1, and US 2013/0264207 A1, each of which is incorporated by reference herein in its entirety. With reference to FIG. 9A, the nanopore detector comprises a top electrode 901 in contact with a conductive solution (e.g., salt solution) 907. A bottom conductive electrode 902 is near, adjacent, or in proximity to a nanopore 906, which is inserted in a membrane 905. In some instances, the bottom conductive electrode 902 is embedded in a semiconductor 903 in which is embedded electrical circuitry in a semiconductor substrate 904. A surface of the semiconductor 903 may be treated to be hydrophobic. A sample being detected goes through the pore in the nanopore 906. The semiconductor chip sensor is placed in package 908 and this, in turn, is in the vicinity of a temperature control element 909. The temperature control element 909 may be a thermoelectric heating and/or cooling device (e.g., Peltier device). Multiple nanopore detectors may form a nanopore array.

Figure 9B:
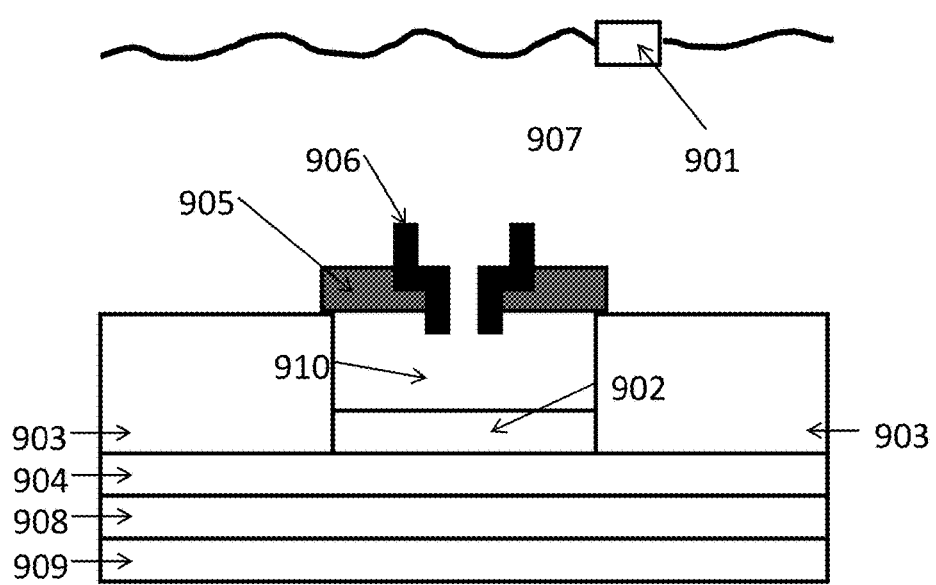
Figure 9C:
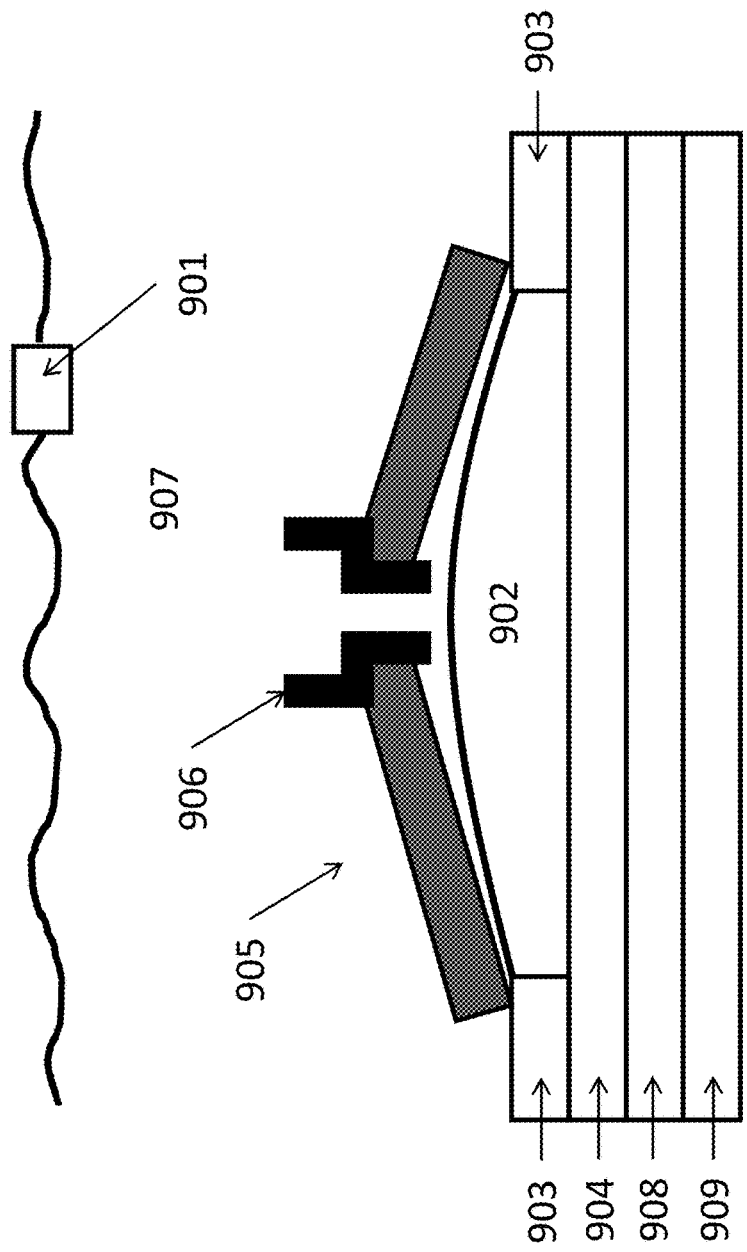

With reference to FIG. 9B, where like numerals represent like elements, the membrane 905 can be disposed over a well 910, where the sensor 902 forms part of the surface of the well. FIG. 9C shows an example in which the electrode 902 protrudes from the treated semiconductor surface 903.

In some examples, the membrane 905 forms on the bottom conductive electrode 902 and not on the semiconductor 903. The membrane 905 in such a case may form coupling interactions with the bottom conductive electrode 902. In some cases, however, the membrane 905 forms on the bottom conductive electrode 902 and the semiconductor 903. As an alternative, the membrane 905 can form on the semiconductor 903 and not on the bottom conductive electrode 902, but may extend over the bottom conductive electrode 902.

Nanopores may be used to sequence nucleic acid molecules indirectly, in some cases with electrical detection. Indirect sequencing may be any method where an incorporated nucleotide in a growing strand does not pass through the nanopore. The nucleic acid molecule may pass within any suitable distance from and/or proximity to the nanopore, in some cases within a distance such that tags released from nucleotide incorporation events are detected in the nanopore.

Byproducts of nucleotide incorporation events may be detected by the nanopore. "Nucleotide incorporation events" are the incorporation of a nucleotide into a growing polynucleotide chain. A byproduct may be correlated with the incorporation of a given type nucleotide. The nucleotide incorporation events are generally catalyzed by an enzyme, such as DNA polymerase, and use base pair interactions with a template molecule to choose amongst the available nucleotides for incorporation at each location.

A nucleic acid sample may be sequenced using tagged nucleotides. In some examples, a method for sequencing a nucleic acid molecule comprises (a) incorporating (e.g., polymerizing) tagged nucleotides, wherein a tag associated with an individual nucleotide is released upon incorporation, and (b) detecting the tag during the incorporation process, either while it attached and bound in the nucleotide-enzyme complex or upon its release, with the aid of a nanopore. In some instances, the method further comprises directing the tag attached to or released from an individual nucleotide through the nanopore. The released or attached tag may be directed by any suitable technique, in some cases with the aid of an enzyme (or molecular motor) and/or a voltage difference across the pore. Alternatively, the released or attached tag may be directed through the nanopore without the use of an enzyme. For example, the tag may be directed by a voltage difference across the nanopore as described herein.

In some cases, the byproduct passes through the nanopore and/or generates a signal detectable in the nanopore. Released tags are an example of byproducts. In some cases, the byproducts are protons (i.e., a pH change). In other cases, the byproducts are phosphates (e.g., phosphates released during nucleotide incorporation events). For example, each of the different types of nucleotides may comprise a different number of phosphates, and detection of the released phosphates allows one to determine the identity of the incorporated nucleotide.

Figure 10:
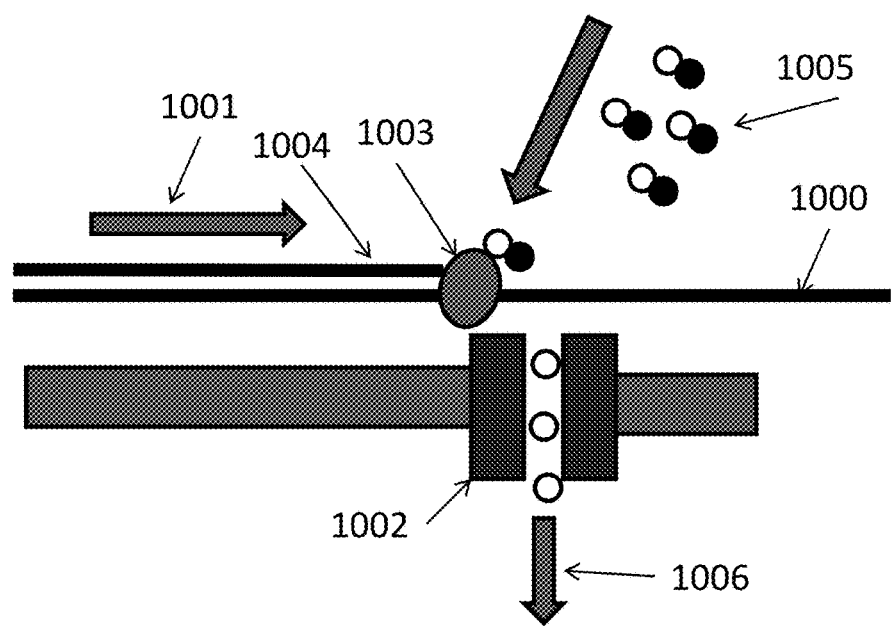
FIG. 10 illustrates a method for nucleic acid sequencing.

An example of the method is depicted in FIG. 10. Here, the nucleic acid strand 1000 passes across or in proximity to (but not through as indicated by the arrow at 1001) the nanopore 1002. An enzyme 1003 (e.g., DNA polymerase) extends a growing nucleic acid strand 1004 by incorporating one nucleotide at a time using a first nucleic acid molecule as a template 1000 (i.e., the enzyme catalyzes nucleotide incorporation events).

The enzyme 1003 may be attached to the nanopore 1002. Suitable methods for attaching the enzyme to the nanopore include cross-linking such as the formation of intra-molecular disulfide bonds, or via another covalent conjugation reaction, such as an inverse electron demand Diels-Alder (IEDDA) reaction as described in U.S. Provisional Application No. 62/130,326, which is hereby incorporated by reference. The nanopore and the enzyme may also be a fusion protein that is encoded by a single polypeptide chain. Methods for producing fusion proteins are known in the art and include fusing the coding sequence for the enzyme in frame and adjacent to the coding sequence for the nanopore (without a stop codon in between) and expressing this fusion sequence from a single promoter. In some cases, phosphatase enzymes are also attached to the nanopore.

Generally, the polymerase used in the methods of the present disclosure can include any naturally-occurring or non-naturally occurring (e.g., engineered) enzyme that has 5'→3' DNA polymerase activity and strong strand displacement activity but lacks 5'→3' exonuclease activity. In some cases, the DNA polymerase is 9° N polymerase or a variant thereof, E. coli DNA polymerase I, Bacteriophage T4 DNA polymerase, Sequenase, Taq DNA polymerase, DNA polymerase from *Bacillus stearothermophilus*, Bst 2.0 DNA polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, or Vent$_R$ DNA polymerase.

Figure 38:
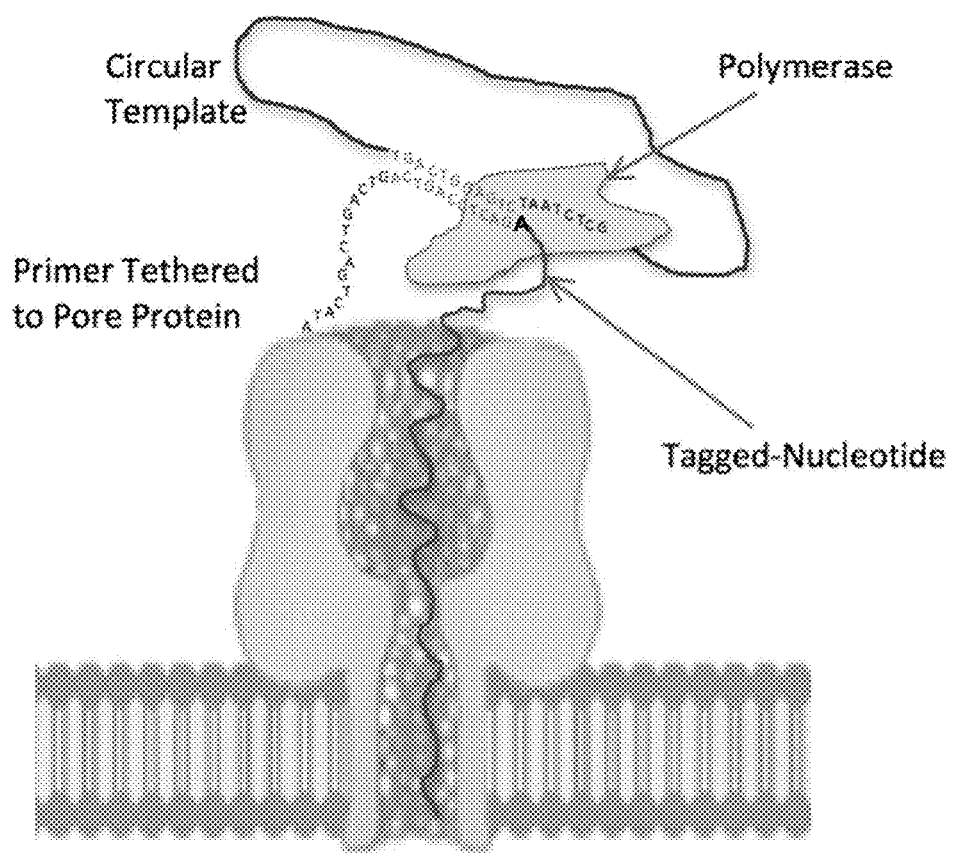
FIG. 38 depicts attachment of primer (SEQ ID NO: 121) to the nanopore and adding template (SEQ ID NO: 122), tagged nucleotides, and DNA polymerase for DNA sequencing. As illustrated in the figure, the tagged "A" nucleotide binds to the polymerase active site with its tag positioned to enter the nanopore for detection by current blockade.

Generally, the polymerase requires the presence of a primer strand that hydridizes to the template DNA strand that is extended by the enzyme and thereby sequenced. Accordingly, in another possible configuration of the nanopore device of the present disclosure, the primer strand is attached to the pore protein, the template DNA strand is hybridized to this attached primer strand, and the polymerase binds to the template primer hybrid and thereby is non-covalently bound to the nanopore device. Such an embodiment is depicted in FIG. 38. The tag attached to the complementary tagged nucleotide is attracted to the lumen of the nanopore by the electrostatic field gradient, ensuring that it can be detected and identified by monitoring current in the pore.

A nucleic acid sample may be sequenced using tagged nucleotides. In some examples, a method for sequencing a nucleic acid molecule comprises (a) polymerizing tagged nucleotides, wherein a tag associated with an individual nucleotide is released upon polymerization, and (b) detecting the released tag with the aid of a nanopore.

In some instances, the method further comprises directing the tag released from an individual nucleotide through the nanopore. The released tag may be directed by any suitable technique, in some cases with the aid of an enzyme (or molecular motor). Alternative, the released tag may be directed through the nanopore without the use of an enzyme. For example, the tag may be directed by a voltage difference across the nanopore as described herein.

With continued reference to FIG. 10, the enzyme draws from a pool of nucleotides (filled circles at indication 1005) attached to tags (open circles at indication 1005). Each type of nucleotide is attached to a different tag so that when the tags are released and pass through the nanopore 1006, they may be differentiated from each other based on the signal that is generated in the nanopore.

Figure 11:
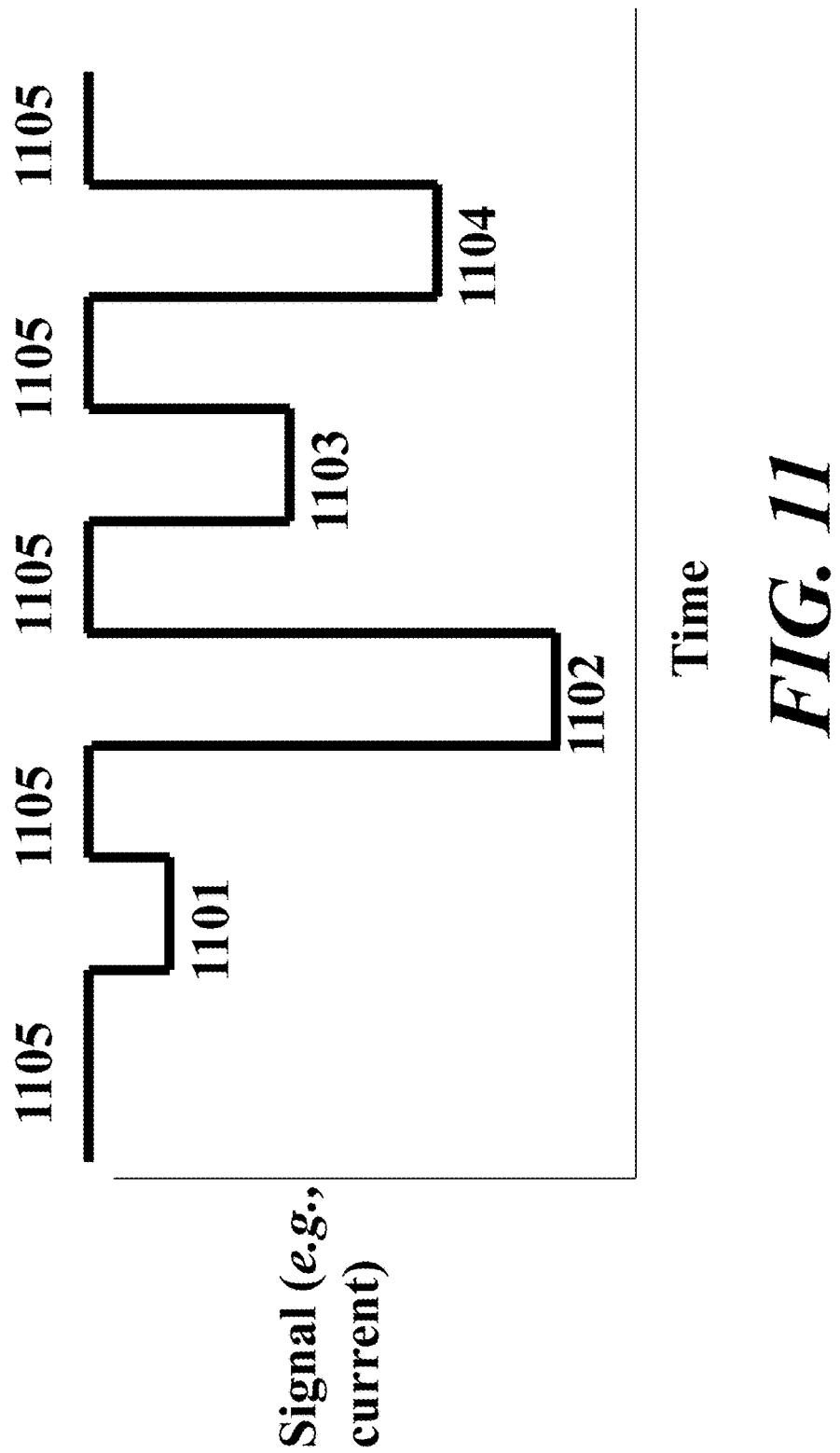
FIG. 11 shows an example of a signal generated by the passage of tags through a nanopore.

FIG. 11 shows an example of different signals being generated by different tags as they pass through the nanopore. Four different signal intensities (1101, 1102, 1103 and 1104) are detected. These correspond to four different tags. For example, the tag released by incorporation of adenosine (A) may generate a signal with an amplitude 1101. A tag released by incorporation of cytosine (C) may generate a signal with a higher amplitude 1103. A tag released by incorporation of guanine (G) may generate a signal with a yet higher amplitude 1104. And a tag released by incorporation of thymine (T) may generate a signal with a yet higher amplitude 1102. The lack of signal during periods when there is no tag passing through the nanopore are indicated by 1105.

The rate of nucleotide incorporation events is generally slower than (or equal to) the rate at which tags molecules released during the nucleotide incorporation events pass through and/or are detected by the nanopore. Generally, the rate of nucleotide incorporation events is not greater than the rate at which tags molecules released during the nucleotide incorporation events pass through and/or are detected by the nanopore (i.e., otherwise the nucleotide incorporation events are not detected accurately and/or in the correct sequence).

Figure 12:
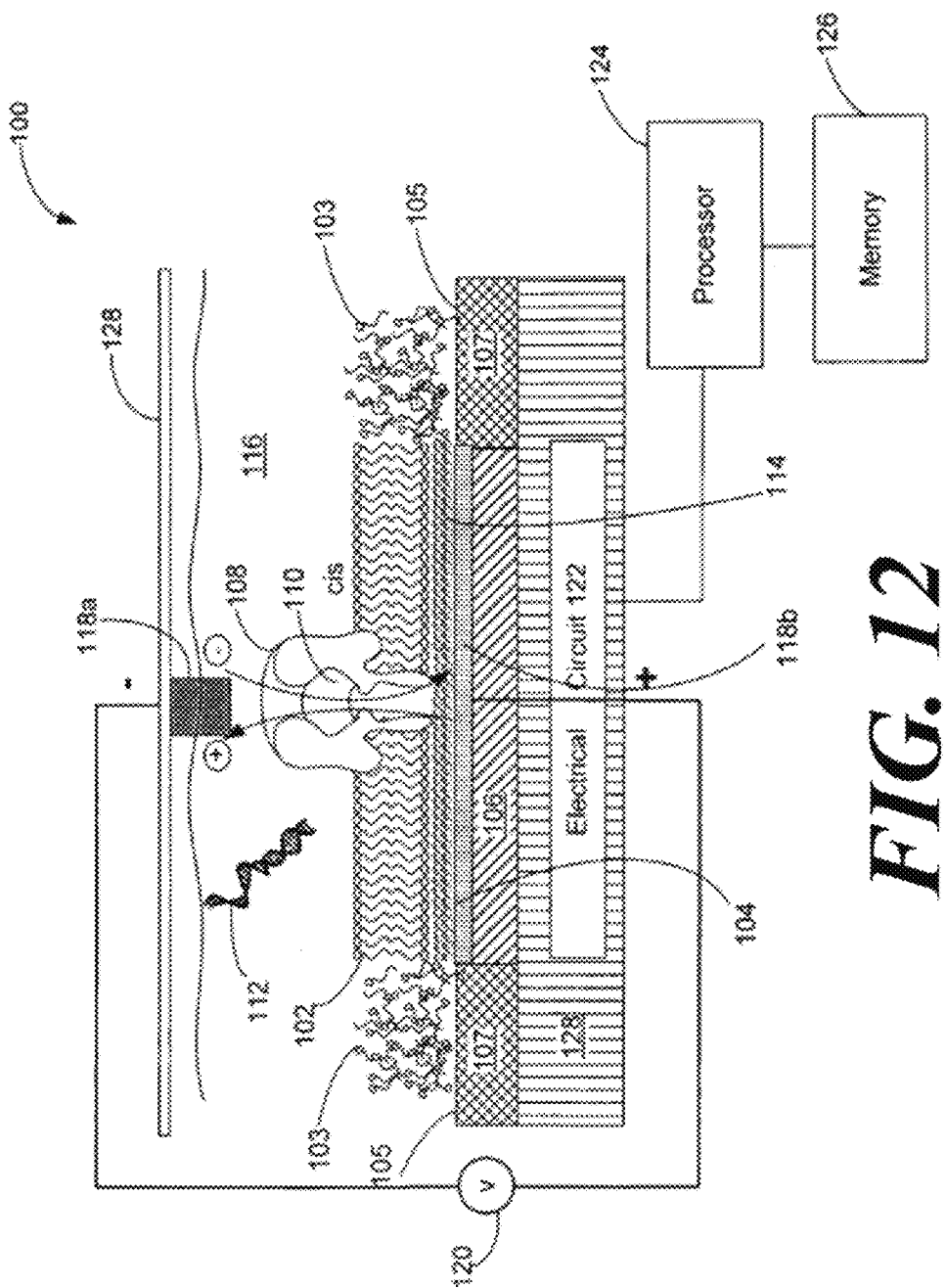
FIG. 12 shows an exemplary chip set-up comprising a nanopore.

The present disclosure provides various devices for molecular identification and/or sensing. FIG. 12 is a schematic diagram of a nanopore device 100 (or sensor) that may be used to sequence a nucleic acid and/or detect a tag as described herein. The nanopore containing lipid bilayer may be characterized by a resistance and capacitance. The nanopore device 100 includes a lipid bilayer 102 formed on a lipid bilayer compatible surface 104 of a conductive solid substrate 106, where the lipid bilayer compatible surface 104 may be isolated by lipid bilayer incompatible surfaces 105 and the conductive solid substrate 106 may be electrically isolated by insulating materials 107, and where the lipid bilayer 102 may be surrounded by amorphous lipid 103 formed on the lipid bilayer incompatible surface 105. The lipid bilayer 102 may be embedded with a single nanopore structure 108 having a nanopore 110 large enough for passing of the tags being characterized and/or small ions (e.g., $Na^+$, $K^+$, $Ca^{2+}$, $Cl^-$) between the two sides of the lipid bilayer 102. A layer of water molecules 114 may be adsorbed on the lipid bilayer compatible surface 104 and sandwiched between the lipid bilayer 102 and the lipid bilayer compatible surface 104. The aqueous film 114 adsorbed on the hydrophilic lipid bilayer compatible surface 104 may promote the ordering of lipid molecules and facilitate the formation of lipid bilayer on the lipid bilayer compatible surface 104. A sample chamber 116 containing a solution of the nucleic acid molecule 112 and tagged nucleotides may be provided over the lipid bilayer 102. The solution may be an aqueous solution containing electrolytes and buffered to an optimum ion concentration and maintained at an optimum pH to keep the nanopore 110 open. The device includes a pair of electrodes 118 (including a negative node 118a and a positive node 118b) coupled to a variable voltage source 120 for providing electrical stimulus (e.g., voltage bias) across the lipid bilayer and for sensing electrical characteristics of the lipid bilayer (e.g., resistance, capacitance, and ionic current flow).

The surface of the positive electrode 118b is or forms a part of the lipid bilayer compatible surface 104. The conductive solid substrate 106 may be coupled to or forms a part of one of the electrodes 118. The device 100 may also include an electrical circuit 122 for controlling electrical stimulation and for processing the signal detected. In some embodiments, the variable voltage source 120 is included as a part of the electrical circuit 122. The electrical circuitry 122 may include amplifier, integrator, noise filter, feedback control logic, and/or various other components. The electrical circuitry 122 may be integrated electrical circuitry integrated within a silicon substrate 128 and may be further coupled to a computer processor 124 coupled to a memory 126.

The lipid bilayer compatible surface 104 may be formed from various materials that are suitable for ion transduction and gas formation to facilitate lipid bilayer formation. In some embodiments, conductive or semi-conductive hydrophilic materials may be used because they may allow better detection of a change in the lipid bilayer electrical characteristics. Example materials include Ag—AgCl, Au, Pt, or doped silicon or other semiconductor materials. In some cases, the electrode is not a sacrificial electrode.

The lipid bilayer incompatible surface 105 may be formed from various materials that are not suitable for lipid bilayer formation and they are typically hydrophobic. In some embodiments, non-conductive hydrophobic materials are preferred, since it electrically insulates the lipid bilayer regions in addition to separate the lipid bilayer regions from each other. Example lipid bilayer incompatible materials include for example silicon nitride (e.g., $Si_3N_4$) and Teflon.

In an example, the nanopore device 100 can be an alpha heolysin (αHL) nanopore device having a single alpha hemolysin (αHL) protein 108 embedded in a diphytanoyl-phosphatidylcholine (DPhPC) lipid bilayer 102 formed over a lipid bilayer compatible Pt surface 104 coated on an aluminum material 106. The lipid bilayer compatible Pt surface 104 is isolated by lipid bilayer incompatible silicon nitride surfaces 105, and the aluminum material 106 is electrically insulated by silicon nitride materials 107. The aluminum 106 is coupled to electrical circuitry 122 that is integrated in a silicon substrate 128. A silver-silver chloride electrode placed on-chip or extending down from a cover plate 128 contacts an aqueous solution containing nucleic acid molecules.

The αHL nanopore is an assembly of seven individual peptides. The entrance or vestibule of the αHL nanopore is approximately 26 Angstroms in diameter, which is wide enough to accommodate a portion of a dsDNA molecule. From the vestibule, the αHL nanopore first widens and then narrows to a barrel having a diameter of approximately 15 Angstroms, which is wide enough to allow a single ssDNA molecule (or the released tags) to pass through but not wide enough to allow a dsDNA molecule to pass through.

In addition to DPhPC, the lipid bilayer of the nanopore device may be assembled from various other suitable amphiphilic materials, selected based on various considerations, such as the type of nanopore used, the type of molecule being characterized, and various physical, chemical and/or electrical characteristics of the lipid bilayer formed, such as stability and permeability, resistance, and capacitance of the lipid bilayer formed. Example amphiphilic materials include various phospholipids such as palmitoyl-oleoyl-phosphatidyl-choline (POPC) and dioleoyl-phosphatidyl-methylester (DOPME), diphytanoylphosphatidylcholine (DPhPC) dipalmitoylphosphatidylcholine (DPPC), phosphatidylcholine, phosphatidylethanolamine, phosphatidylserine, phosphatidic acid, phosphatidylinositol, phosphatidylglycerol, and sphingomyelin.

In addition to the αHL nanopore shown above, the nanopore may be of various other types of nanopores. Examples include γ-hemolysin, leukocidin, melittin, and various other naturally occurring, modified natural, and synthetic nanopores. A suitable nanopore may be selected based on various characteristics of the analyte molecule such as the size of the analyte molecule in relation to the pore size of the nanopore. For example, the αHL nanopore that has a restrictive pore size of approximately 15 Angstroms.

Figure 13:
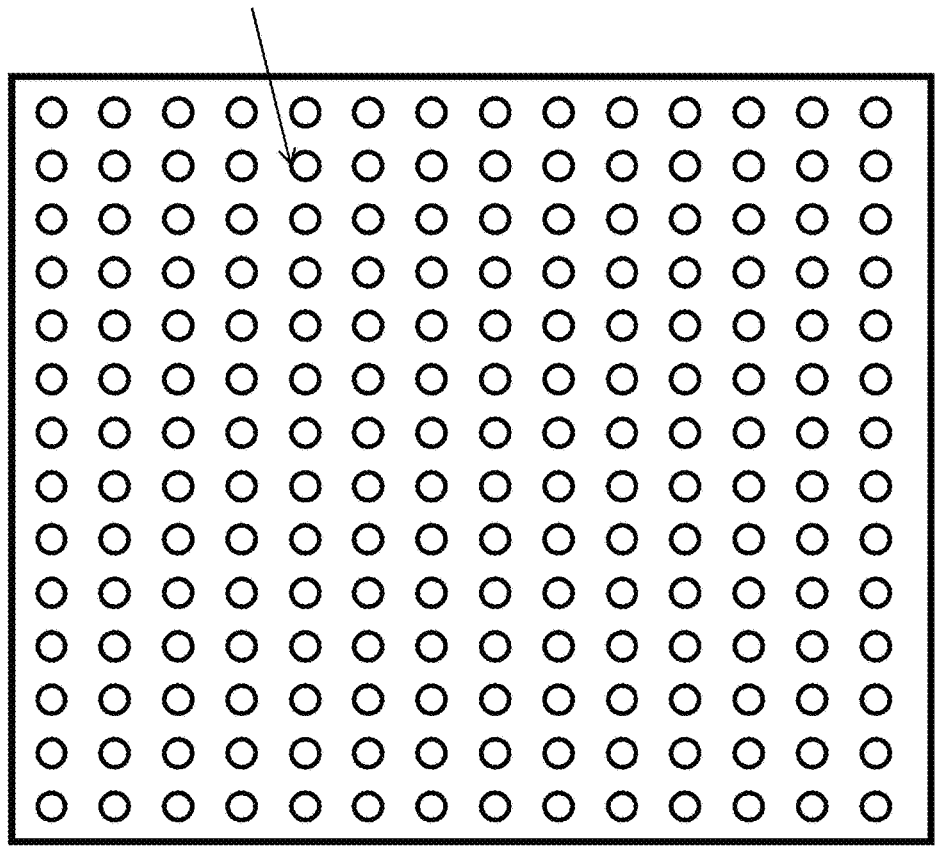
FIG. 13 shows an array of nanopore detectors.

FIG. 13 shows that a plurality of nucleic acid molecules may be sequenced on an array of nanopore detectors. Here, each nanopore location (e.g., 1301) comprises a nanopore, in some cases attached to a polymerase enzyme and/or phosphatase enzymes. There is also generally a sensor at each array location as described elsewhere herein.

In some examples, an array of nanopores attached to a nucleic acid polymerase is provided, and tagged nucleotides are polymerized with the polymerase. During polymerization, a tag is released and detected by the nanopore. The array of nanopores may have any suitable number of nanopores. In some instances, the array comprises about 200, about 400, about 600, about 800, about 1000, about 1500, about 2000, about 3000, about 4000, about 5000, about 10000, about 15000, about 20000, about 40000, about 60000, about 80000, about 100000, about 200000, about 400000, about 600000, about 800000, about 1000000, and the like nanopores. In some instances, the array comprises at least 200, at least 400, at least 600, at least 800, at least 1000, at least 1500, at least 2000, at least 3000, at least 4000, at least 5000, at least 10000, at least 15000, at least 20000, at least 40000, at least 60000, at least 80000, at least 100000, at least 200000, at least 400000, at least 600000, at least 800000, at least 1000000, and the like nanopores.

In some cases, a single tag is released upon incorporation of a single nucleotide and detected by a nanopore. In other cases, a plurality of tags is released upon incorporation of a plurality of nucleotides. A nanopore sensor adjacent to a nanopore may detect an individual released tag, or a plurality of released tag. One or more signals associated with plurality of released tags may be detected and processed to yield an averaged signal.

Tags may be detected by the sensor as a function of time. Tags detected with time may be used to determine the nucleic acid sequence of the nucleic acid sample, such as with the aid of a computer system (see, e.g., FIG. 14) that is programmed to record sensor data and generate sequence information from the data.

A nanopore based sequencing chip may incorporate a large number of autonomously operating or individually addressable cells configured as an array. For example an array of one million cells can be constructed of 1000 rows of cells by 1000 columns of cells. This array enables the parallel sequencing of nucleic acid molecules by measuring the conductance difference when tags released upon nucleotide incorporation events pass through the nanopore for example. Moreover this circuitry implementation allows the conductance characteristics of the pore-molecular complex to be determined which may be extremely valuable in distinguishing specific tags.

The integrated nanopore/bilayer electronic cell structures may apply appropriate voltages in order to perform current measurements. For example, it may be necessary to both (a) control electrode voltage potential and (b) monitor electrode current simultaneously in order to perform correctly.

Moreover it may be necessary to control cells independently from one another. The independent control of a cell may be required in order to manage a large number of cells that may be in different physical states. Precise control of the piecewise linear voltage waveform stimulus applied to the electrode may be used to transition between the physical states of the cell.

In order to reduce the circuit size and complexity it may be sufficient to provide logic to apply two separate voltages. This allows two independent grouping of cells and corresponding state transition stimulus to be applied. The state transitions are stochastic in nature with a relatively low probability of occurrence. Thus it may be highly useful to be able to assert the appropriate control voltage and subsequently perform a measurement to determine if the desired state transition has occurred. For example the appropriate voltage may be applied to a cell and then the current measured to determine whether a pore has formed. The cells are divided into two groups: (a) those which have had a pore form and no longer need to have the voltage applied. These cells may have a 0V bias applied in order to effect the null operation (NOP)—that is stay in the same state and (b) those which do not have a pore formed. These cells will again have the pore formation electric voltage applied.

A substantial simplification and circuit size reduction may be achieved by constraining the allowable applied voltages to two and iteratively transitioning cells in batches between the physical states.

For example, a reduction by at least a factor of 1.1, 2, 3, 4, 5, 6, 7, 8, 9, 10, 20, 30, 40, 50, or 100 may be achieved by constraining the allowable applied voltages.

Computer Control Systems

Figure 14:
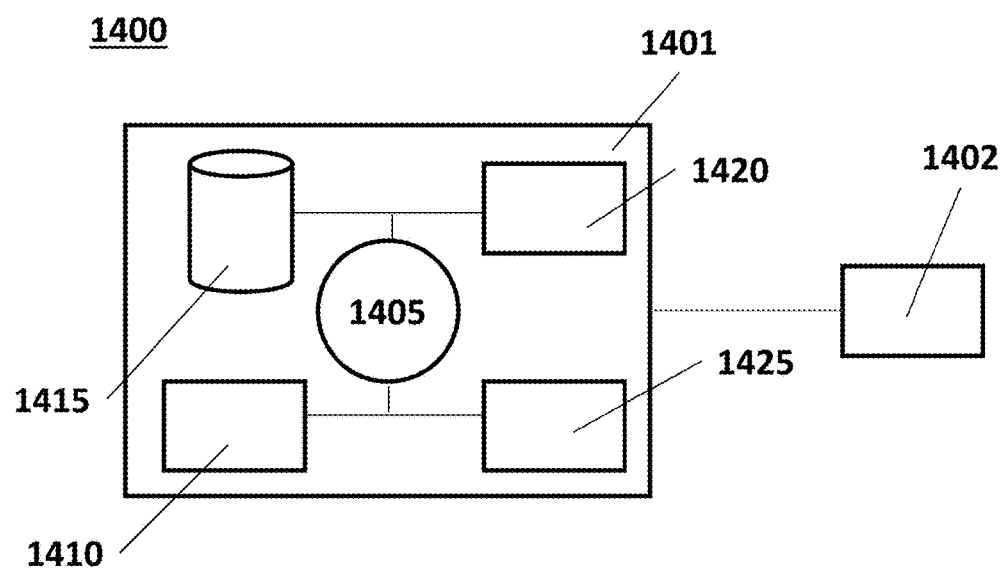
FIG. 14 shows a computer system configured to control a sequencer.

Nucleic acid sequencing systems and methods of the disclosure may be regulated with the aid of computer systems. FIG. 14 shows a system 1400 comprising a computer system 1401 coupled to a nucleic acid sequencing system 1402. The computer system 1401 may be a server or a plurality of servers. The computer system 1401 may be programmed to regulate sample preparation and processing, and nucleic acid sequencing by the sequencing system 1402. The sequencing system 1402 may be a nanopore-based sequencer (or detector), as described elsewhere herein.

The computer system may be programmed to implement the methods of the invention. The computer system 1401 includes a central processing unit (CPU, also "processor" herein) 1405, which can be a single core or multi core processor, or a plurality of processors for parallel processing. The computer system 1401 also includes memory 1410 (e.g., random-access memory, read-only memory, flash memory), electronic storage unit 1415 (e.g., hard disk), communications interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communications bus (solid lines), such as a motherboard. The storage unit 1415 can be a data storage unit (or data repository) for storing data. The computer system 1401 may be operatively coupled to a computer network ("network") with the aid of the communications interface 1420. The network can be the Internet, an internet and/or extranet, or an intranet and/or extranet that is in communication with the Internet. The network can include one or more computer servers, which can enable distributed computing.

Methods of the invention can be implemented by way of machine (or computer processor) executable code (or software) stored on an electronic storage location of the computer system 1401, such as, for example, on the memory 1410 or electronic storage unit 1415. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine have a processer adapted to execute the code, or can be compiled during runtime. The code can be supplied in a programming language that can be selected to enable the code to execute in a pre-compiled or as-compiled fashion.

The computer system 1401 can be adapted to store user profile information, such as, for example, a name, physical address, email address, telephone number, instant messaging (IM) handle, educational information, work information, social likes and/or dislikes, and other information of potential relevance to the user or other users. Such profile information can be stored on the storage unit 1415 of the computer system 1401.

Aspects of the systems and methods provided herein, such as the computer system 1401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., ROM, RAM) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Synthesis of a Coumarin-PEG-dG4P Tagged Nucleotide

In this example, nucleotides are purified by reverse-phase HPLC on a 150×4.6 mm column (Supelco), mobile phase: A, 8.6 mM $Et_3N$/100 mM 1,1,1,3,3,3-hexafluoro-2-propanol in water (pH 8.1); B, methanol. Elution is performed from 100% A isocratic over 10 min followed by a linear gradient of 0-50% B for 20 mM and then 50% B isocratic over another 30 min.

Figure 16:
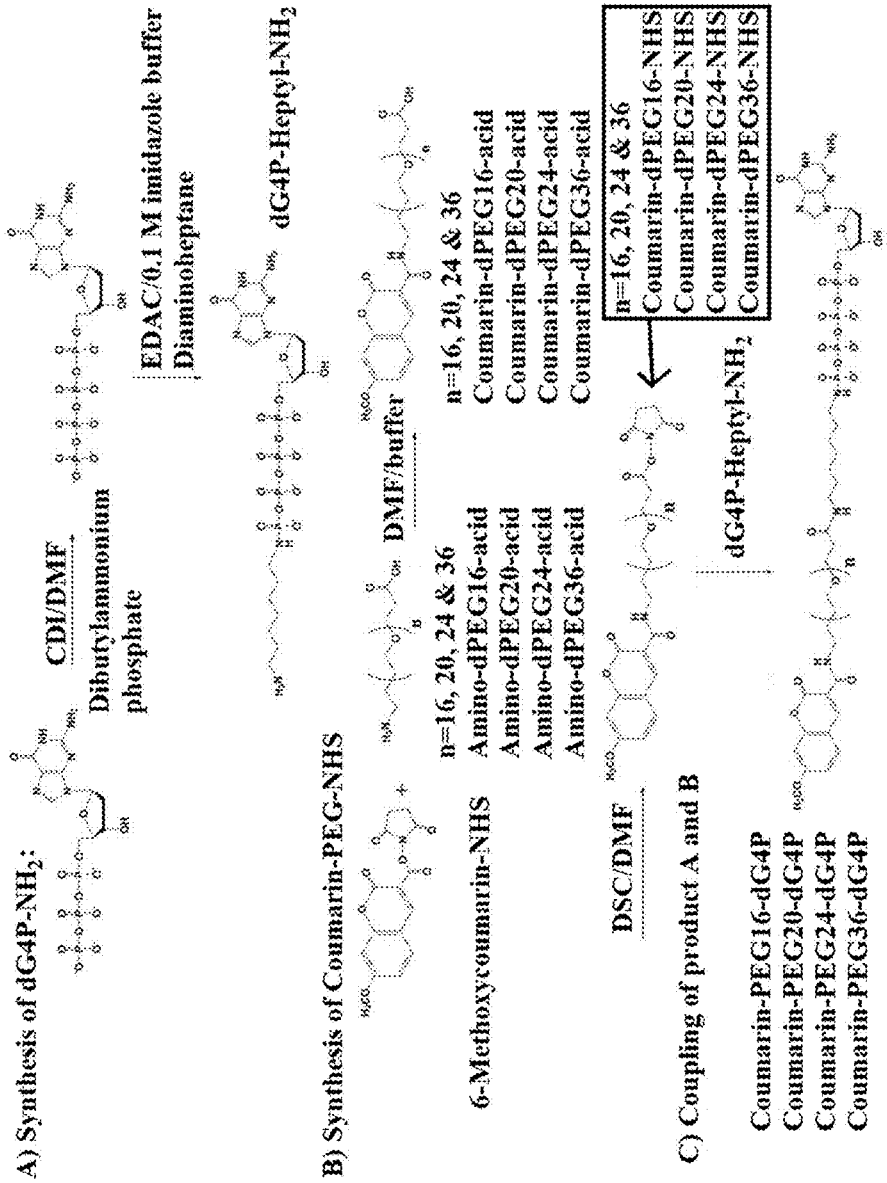
FIG. 16 shows an example of synthesis of coumarin-PEG-dG4P tagged nucleotides.

The synthesis of coumarin-$PEG_n$-dG4P involves three synthesis operations, A, B, and C as shown in the scheme in FIG. 16.

A. Syntheses of 2'-deoxyguanosine-5'-tetraphosphate (dG4P) and dG4P-$NH_2$: First, the synthesis of 2'-dG4P is carried out starting from 2'-dGTP. 300 umoles of 2'-dGTP (triethylammonium salt) is converted to the tributylammonium salt by using 1.5 mmol (5 eq) of tributylamine in anhydrous pyridine (5 ml). The resulting solution is concentrated to dryness and co-evaporated with 5 ml of anhydrous DMF (×2). The dGTP (tributylammonium salt) is dissolved in 5 ml anhydrous DMF, and 1.5 mmol 1, 1-carbonyldiimidazole added. The reaction is stirred for 6 hr, after which 12 ul methanol added and stirring continued for 30 min. To this solution, 1.5 mmol phosphoric acid (tributylammonium salt, in DMF) added and the reaction mixture stirred overnight at room temperature. The reaction mixture is diluted with water and purified on a Sephadex-A25 column using 0.1 M to 1M TEAB gradient (pH 7.5). The dG4P elutes at the end of the gradient. The appropriate fractions are combined and further purified by reverse-phase HPLC to provide 175 umol of the pure tetraphosphate (dG4P). $^{31}$P-NMR: δ, −10.7 (d, 1P, α-P), −11.32 (d, 1P, δ-P), −23.23 (dd, 2P, β, γ-P); ESI-MS (-ve mode): Calc. 587.2. Found 585.9 (M−2).

To 80 μmol dG4P in 2 ml water and 3.5 ml 0.2M 1-methylimidazole-HCl (pH 6) added 154 mg EDAC and 260 mg diaminoheptane. The pH of the resulting solution is adjusted to 6 with concentrated HCl and stirred at room temperature overnight. This solution is diluted with water and purified by Sephadex-A25 ion-exchange chromatography followed by reverse-phase HPLC to give ~20 μmol dG4P-NH$_2$. This is confirmed by ESI-MS data (-ve mode): talc. 699.1. Found (698.1, M−1).

B. Synthesis of coumarin-PEG-acids and NHS esters: The commercially available amino-dPEG-acids [Amino-d(PEG) 16, 20, 24, 36-acids; Quanta Biodesign] are reacted with 6-methoxy coumarin-NHS ester to provide the corresponding coumarin-(PEG)$_n$-acid. Amino-PEG-acid (1 eq) is dissolved in carbonate-bicarbonate buffer (pH 8.6), followed by addition of coumarin-NHS (1 eq) in DMF, and the reaction mixture stirred overnight. The coumarin-PEG-acid is purified by silica-gel chromatography using a CH$_2$Cl$_2$-MeOH (5-15%) mixture and the appropriate fractions combined. These compounds are analyzed by $^1$H NMR and MALDI-TOF MS analysis. Results are shown in Table 2.

TABLE 2

MALDI-TOF MS Data:

|  | Coumarin-PEG16-acid | Coumarin-PEG20-acid | Coumarin-PEG24-acid | Coumarin-PEG36-acid |
|---|---|---|---|---|
| Expected MW | 996 | 1,172 | 1,348 | 1,877 |
| Observed MW* | 1,016 | 1,192 | 1,368 | 1,899 |

*Difference in observed values due to presence of sodium salt.

The coumarin-PEG-acids are converted to the corresponding NHS esters by reacting with 1.5 eq. of disuccinimidyl carbonate (DSC) and 2 eq of triethylamine in anhydrous DMF for 2 h. The resulting NHS ester, which moves slightly higher than the acid on silica-gel plates, is purified by silica-gel chromatography using a CH$_2$Cl$_2$-MeOH (5-15%) mixture and used in the next operation.

Coupling of operation A and B products to form coumarin-PEG$_n$-dG4P: dG4P-heptyl-NH2 from operation A) above is taken up in 0.1 M carbonate-bicarbonate buffer (pH 8.6) and to this stirred solution added one of the coumarin-PEG-NHS compounds (in DMF). The resulting mixture stirred overnight at room temperature and then purified on a silica-gel cartridge (15-25% MeOH in CH$_2$Cl$_2$ to remove unreacted coumarin-acid or —NHS and then 6:4:1 isopropanol/NH$_4$OH/H$_2$O). This is further purified twice by reverse-phase HPLC to provide pure coumarin-PEG-dG4P. The structure is confirmed by analysis on MALDI-TOF MS. Coumarin-PEG16-dG4P: retention time, 31.7 min; coumarin-PEG20-dG4P: retention time, 32.2 min; coumarin-PEG24-dG4P: retention time, 33.0 min; coumarin-PEG36-dG4P: retention time, 34.3 min. Results are shown in Table 3.

TABLE 3

MALDI-TOF MS Data:

|  | Coumarin-PEG16-dG4P | Coumarin-PEG20-dG4P | Coumarin-PEG24-dG4P | Coumarin-PEG36-dG4P |
|---|---|---|---|---|
| Expected MW | 1,673 | 1,850 | 2,025 | 2,554 |
| Observed MW | 1,682 | 1,858 | 2,036 | 2,569 |

Example 2

Characterization of the Released Tags by MALDI-TOF MS

Figure 17:
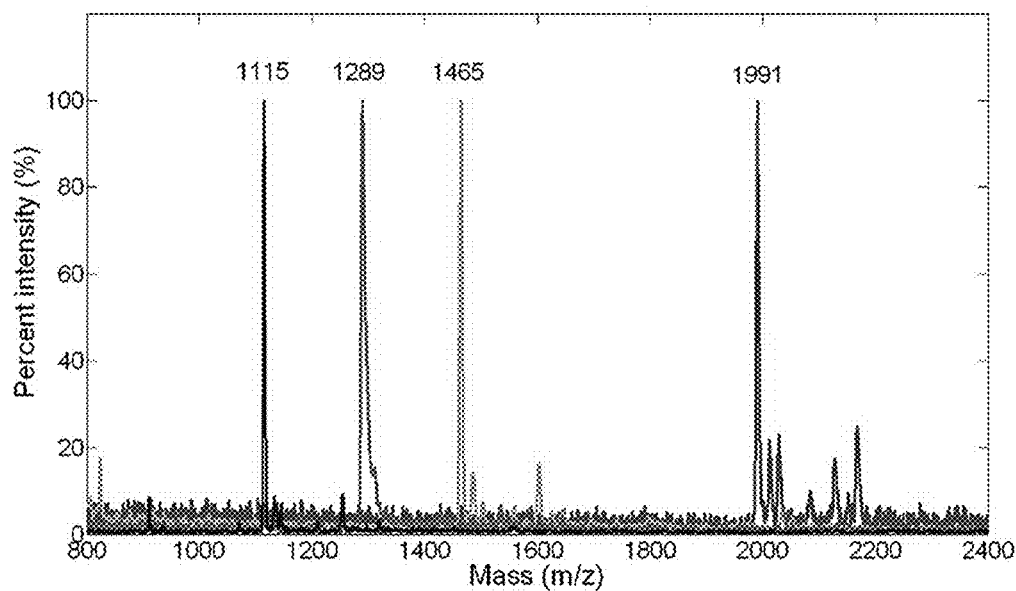
FIG. 17 shows an example of characterization of the released tags by MALDI-TOF MS.
Figure 17:
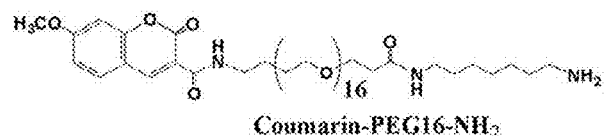
Figure 17:
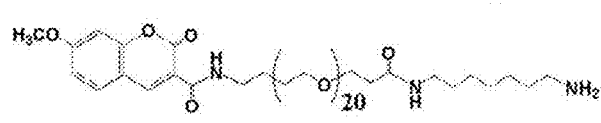
Figure 17:
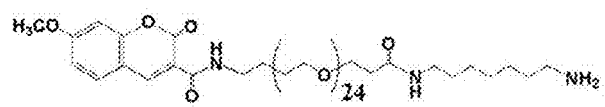
Figure 17:
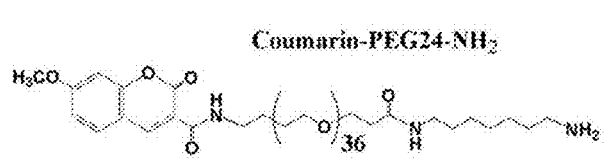

The expected coumarin-PEG-NH$_2$ molecules are confirmed by MALDI-TOF-MS analysis, following HPLC purification (FIG. 17). MALDI-TOF-MS results indicate that the coumarin-PEG-NH$_2$ tags generated by acid hydrolysis are identical to the released tags produced during polymerase reaction after alkaline phosphatase treatment.

With reference to FIG. 17, coumarin-PEG-NH$_2$ tags generated by acid hydrolysis of coumarin-PEG16-dG4P yielding coumarin-PEG16-N1-19, coumarin-PEG20-dG4P yielding coumarin-PEG20-NW, coumarin-PEG24-dG4P yielding coumarin-PEG24-NH9 and coumarin-PEG36-dG4P yielding coumarin-PEG36-NH2, are identical to the corresponding released tags generated in polymerase extension reactions after treatment with alkaline phosphatase, as shown by MALDI-TOF-MS analysis. A composite image of four separately obtained MS spectra is shown. The structures of the coumarin-PEG-NH$_2$ tags are shown to the right.

Example 3

Detection of Oligonucleotide Tags

Figure 18:
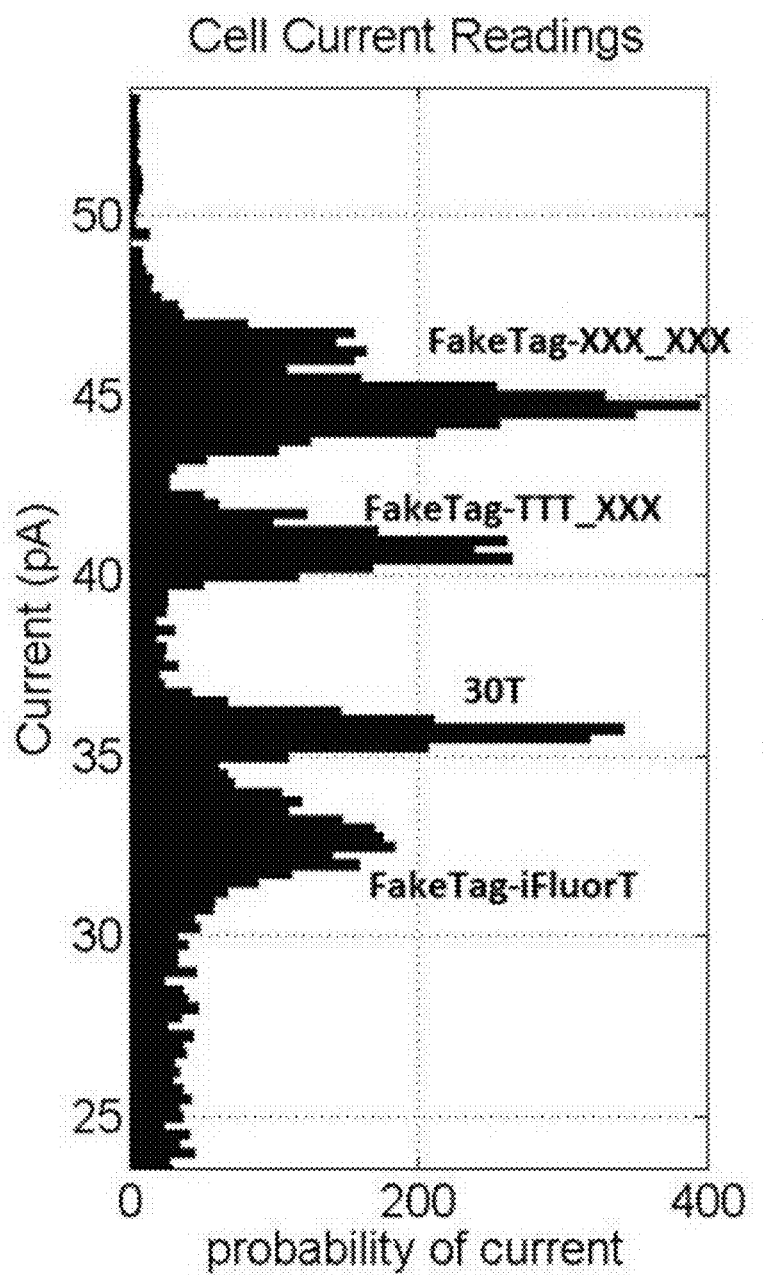
FIG. 18 shows a histogram of cell current readings.

A nanopore array device (see e.g., FIG. 12) is used to detect 4 distinct current levels for 4 different tags. As seen in FIG. 18, each of the tags can be distinguished from any of the other three (i.e., the histogram shows four distinct peaks labeled in the graphic with the corresponding tag). Each tag is an oligonucleotide homopolymer of "T" approximately 30 bases in length, biotinylated on the 3' end with two regions in the strand potentially modified. In each 30 base long molecule, the regions modified are; from the 3'end, base positions 11, 12, and 13 and positions 17, 18, and 19. As used here "x" is an abasic site (no base) and "T" is thymine. The four tags are:

(a) "Fake tag-XXX_XXX" has sequence: Streptavidin-Biotin-10T-xxx-3T-xxx-11T (SEQ ID NO. 1)
(b) "Fake tag-TTT_XXX" has sequence: Streptavidin-Biotin-10T-TTT-3T-xxx-11T (SEQ ID NO. 2)
(c) "30T" tag has sequence: Streptavidin-Biotin-30T (SEQ ID NO. 3)
(d) "Fake tag-iFluorT" has the sequence: Streptavidin-Biotin-10T-TTT-3T-T-iFluorT-T-11T, where the T at position 18 is labeled with fluorescein. (SEQ ID NO. 4)

The results are for one pore in an array capturing multiple tag molecules from solution over time. The detection conditions are 1M KCl, buffered with 20 mM HEPES, pH7.5 at room temperature. Each molecule is captured and held in the pore while a voltage is applied. The applied voltage is increased to +160 mV, a new molecule is captured, and the voltage is reduced below 0V and the tag molecule falls out of the pore. The cycle is then repeated. Four different tags are in the sample mix at once.

As shown in FIG. 18, the clear bands seen during the application of 160 mV become connected or slightly smeared in the histogram because the current during the ramp down is also plotted. Despite this, distinct, repeatable capture bands can be seen for each tag.

Figure 19:
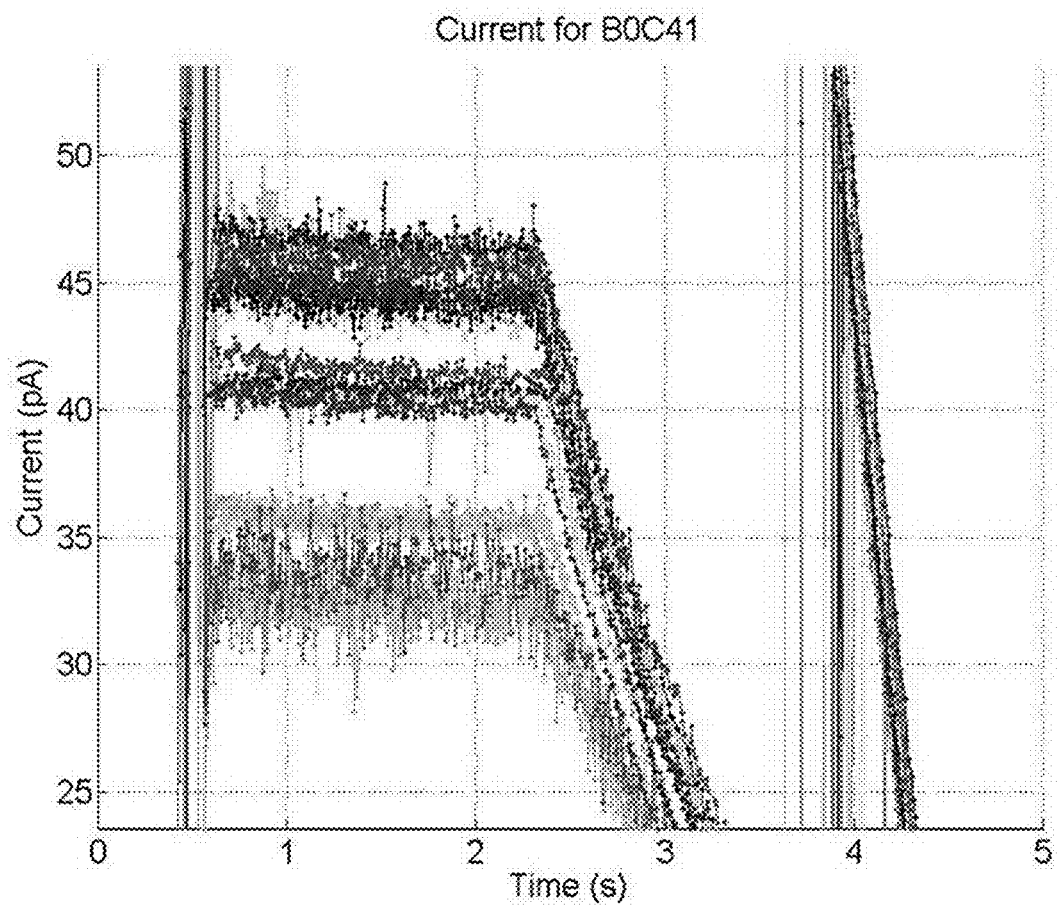
FIG. 19 shows a plot of current measured in pico-amps versus time measured in seconds for 4 different tags.

As shown in FIG. 19, the horizontal axis of the plot is time (measured in seconds) vs. current (measured in pico amps (pA)) on the vertical axis. The applied voltage waveform is not shown. The applied voltage waveform starts below 0V and quickly increases to +160 mV and is held there for approximately 2.3 seconds. The voltage is then ramped down to below 0V. The current readings follow the applied voltage with a captured molecule's current being flat while the applied voltage is at +160 mV and then ramps down as the voltage ramps down.

Example 4

Examples of Conjugation Reactions

Figure 20:
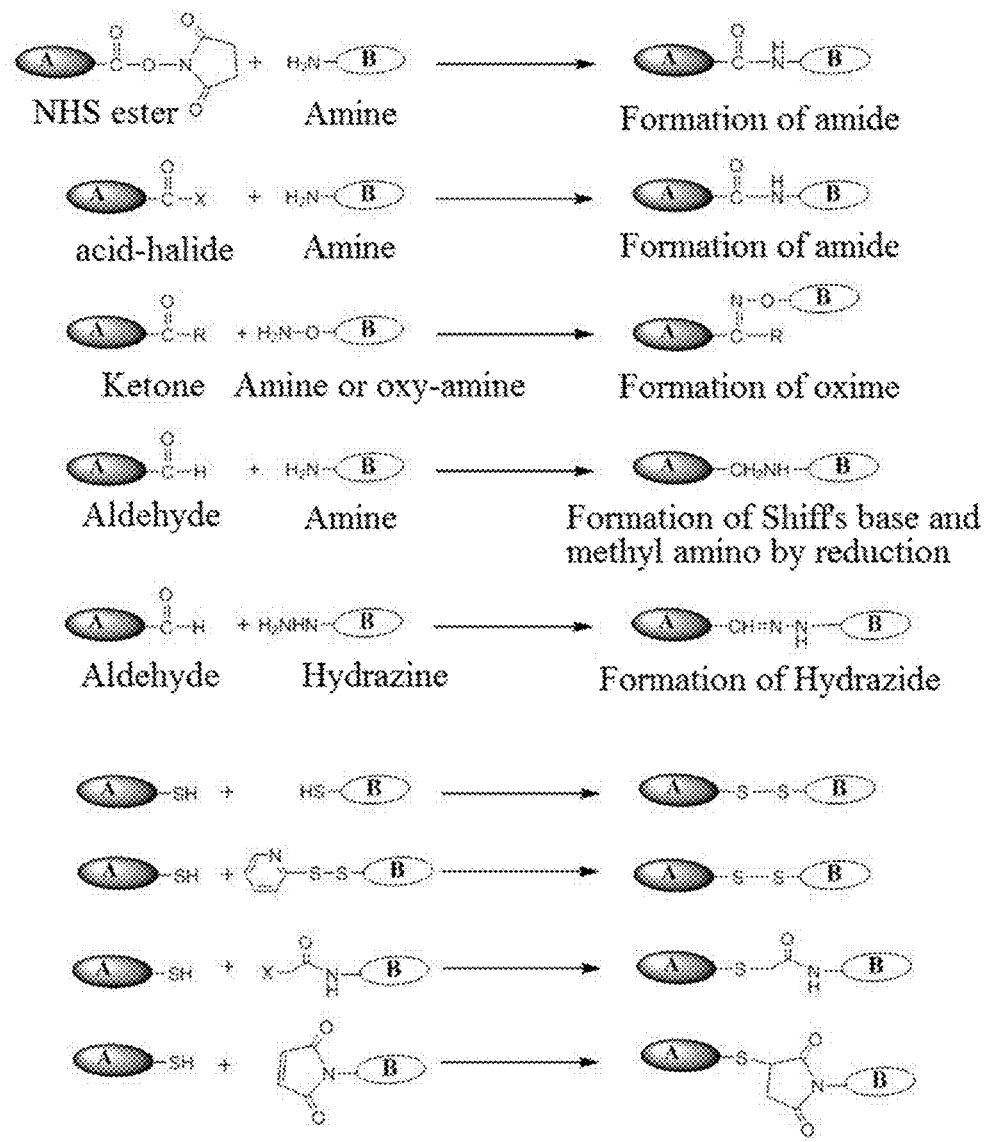
FIG. 20 shows examples of conjugation reactions.

Examples of conjugation reactions are shown in FIG. 20. As shown, (i.) amine reacts with NHS ester to form an amide, (ii.) amine reacts with acid halide to form an amide, (iii.) amine or oxy-amine reacts with ketone to form an oxime, (iv.) amine reacts with aldehyde to form Schiff's base and methyl amino by reduction, and (v.) hydrazine reacts with aldehyde to form a hydrazide. As shown, thiols react with thiols, maleimide or halo-acetamides.

Example 5

Examples of Click Chemistry

Examples of click chemistry using compounds with azide, alkyne, alkene and tetrazine containing moieties are shown in FIG. 21. As shown, conjugation can be accomplished to provide a triazole or 1,2-diazine (dihydropyridazine tautomer) linkage. Azide-containing molecule A reacts with alkyne-containing molecule B to form a conjugate of A and B via a triazole. Also, azide-containing molecule A can react with cyclooctyne-containing molecule B to form a conjugate of A and B via a triazole fused with a cyclooctyl moiety. Alternatively, a tetrazine-containing molecule A reacts with trans-cyclooctene-containing molecule B to form a conjugate of A and B via a dihydropyridazine.

Example 6

Examples of Tagged Nucleotides

Table 4 shows examples of tagged nucleotides that may act as polymerase substrates. Exemplary tagged nucleotides shown in Table 4 may be synthesized from a 5'-azido-hexaphosphate-nucleotide ("dN6P-N3") and an alkyne-tag using either the azide-alkyne or azide-cyclooctyne "click" reaction (see e.g., FIG. 21). Further description of reagents and conditions for the azide-alkyne and azide-cyclooctyne click reaction syntheses are provided below in Examples 7-11.

Table 4 includes numerous tag structures that comprise a natural or unnatural oligonucleotide. These oligonucleotide tags are shown in 5' to 3' orientation and were prepared by phosphoramidite synthesis, and are commercially available based on our design from custom oligonucleotide vendors such as Integrated DNA Technologies (Coralville, Iowa, USA) or TriLink Biotechnologies (San Diego, Calif., USA) or Glen Research (Sterling, Va., USA). There are hundreds of non-standard phosphoramidite monomer unit "building blocks" published and commercially available from custom oligonucleotide vendors that can be easily incorporated into custom synthesized oligonucleotides useful as tags. Many of these non-standard monomer units are classified as spacers (e.g., "iSp"), dyes (e.g., "iCy3"), and linkers (e.g., "hexynyl"). All oligonucleotide tag structures in Table 4 are described using well-known oligonucleotide synthesis nomenclature to indicate the non-standard monomer units. (See e.g., the web-site of Integrated DNA Technologies at www.idtdna.com for further details of commonly used oligonucleotide nomenclature.) For example, non-standard monomer units are enclosed in forward slashes "/" and an asterisk "*" between units indicates a thiophosphate diester linkage. Thus, "/5Hexynyl//iSpC3//iCy3/T" indicates 5'-hexyne-phosphate-dihydroxypropane-phosphate-cyanine 3 (dye)-phosphate-thymidine-3' (OH). A key of further selected abbreviations is included in Table 4.

TABLE 4

| Tagged Nucleotide Name | Tag Structure (including alkyne or cyclooctyne moiety) | SEQ ID No. |
|---|---|---|
| dT6P-Cy3 | DBCO-Cy3 | — |
| dA6P-Cy3 | DBCO-Cy3 | — |
| dT6P-Cy3-T$_{25}$ | /5Hexynyl//iCy3/TTTTT TTTTT TTTTT TTTTT TTTTT | 5 |
| dA6P-T*$_{30}$_ODD | /5Hexynyl/T*TT*TT*TT*TT*TT*TT*TT*TT*TT*TT*TT*TT*TT*TT*T | 6 |
| dG6P-T$_{30}$ | /5Hexynyl/TTTTT TTTTT TTTTT TTTTT TTTTT TTTTT | 7 |
| dT6P-T$_6$-dSp$_8$-T$_{16}$ | /5Hexynyl/TTTTTT/idSp//idSp//idSp//idSp//idSp//idSp//idSp/TTTTT TTTTT TTTTT T | 8 |
| dC6P-T$_6$-T*$_{10}$-T$_{14}$ | /5Hexynyl/TTTTTTT*T*T*T*T*T*T*T*T*T*TTTTT TTTTT TTTT | 9 |
| dC6P-T$_4$-dSp$_3$-T$_{23}$ | /5Hexynyl/TTTT/idSp//idSp//idSp/TTTTT TTTTT TTTTT TTTTT TTT | 10 |
| dC6P-T$_7$-dSp$_3$-T$_{20}$ | /5Hexynyl/TTTTT TT/idSp//idSp//idSp/TTTTT TTTTT TTTTT TTTTT TTTTT | 11 |
| dC6P-T$_{10}$-dSp$_3$-T$_{17}$ | /5Hexynyl/TTTTT TTTTT/idSp//idSp//idSp/TTTTT TTTTT TTTTT TT | 12 |
| dC6P-T$_{13}$-dSp$_3$-T$_{14}$ | /5Hexynyl/TTTTT TTTTT TTT/idSp//idSp//idSp/TTTTT TTTTT TTTT | 13 |

TABLE 4-continued

| Tagged Nucleotide Name | Tag Structure (including alkyne or cyclooctyne moiety) | SEQ ID No. |
|---|---|---|
| dG6P-$T_{30}$-C6 | /5Hexynyl/TTTTT TTTTT TTTTT TTTTT TTTTT TTTTT/3C6/ | 14 |
| dG6P-Cy3-$T_{30}$-C6 | /5Hexynyl//iCy3/TTTTT TTTTT TTTTT TTTTT TTTTT TTTTT/3C6/ | 15 |
| dT6P-$T_4$-$dSp_{10}$-$T_{16}$-C6 | /5Hexynyl/TTTT/idSp//idSp//idSp//idSp//idSp//idSp//idSp//idSp/TTTTT TTTTT TTTTT T/3C6/ | 16 |
| dG6P-$(T_4$-$Npy_2)_6$-C3 | /5Hexynyl/TTTT/X//X/TTTT/X//X/TTTT/X//X/TTTT/X//X/TTTT/X//X/TTTT/X//X//3SpC3/ X = NitroPyrrol | 17 |
| dC6P-$(T_4$-$Neb_2)_6$-C3 | /5Hexynyl/TTTT/X//X/TTTT/X//X/TTTT/X//X/TTTT/X//X/TTTT/X//X/TTTT/X//X//3SpC3/ | 18 |
| dA6P-$T_4$-Sp18-$T_{22}$-C3 | /5Hexynyl/TTTT/iSp18/TTTTT TTTTT TTTTT TTTTT TT/3SpC3/ | 19 |
| dA6P-$T_4$-$Sp18_2$-$T_{19}$-C3 | /5Hexynyl/TTTT/iSp18//iSp18/TTTTT TTTTT TTTTT TTTT/3SpC3/ | 20 |
| dA6P-$T_4$-$Sp9_2$-$T_{22}$-C3 | /5Hexynyl/TTTT/iSp9//iSp9/TTTTT TTTTT TTTTT TTTTT TT/3SpC3/ | 21 |
| dT6P-$dT_6$-$C7NH_6$-$dT_{18}$-C3 | /5Hexynyl/TTTTtT/iUniAmM//iUniAmM//iUniAmM//iUniAmM//iUniAmM/TTTT TTTTT TTTTT TTT/3SpC3/ | 22 |
| dT6P-$dT_6$-$Pyrd_6$-$dT_{18}$-C3 | /5Hexynyl/TTTTTT/X//X//X//X//X//X/TTTT TTTTT TTTTT TTTT/3SpC3/ | 23 |
| dA6P-$dT_6$-$dTNH_6$-$dT_{18}$-C3 | /5Hexynyl/TTTTTT/iAmMC6T//iAmMC6T//iAmMC6T//iAmMC6T//iAmMC6T/TTTT TTTTT TTTTT TTTT/3SpC3/ | 24 |
| dG6P-$dT_4$-sperm-$dT_{22}$-C3 | /5Hexynyl/TTTT/Spermine/TTTTT TTTTT TTTTT TTTTT TT/3SpC3/ | 25 |
| dT6P-$dT_4$-sperm-$dSp_3$-$dT_{19}$-C3 | /5Hexynyl/TI'1 1/SperminelIidSpllidSpllidSp/TT TTTTT TTTTT TTTTT TT/3SpC3/ | 26 |
| dC6P-$dT_4$-sperm-iFlrT-$dT_{21}$-C3 | /5Hexynyl/TTTT/Spermine//iFluorT/TTTT TTTTT TTTTT TTTTT TT/3SpC3/ | 27 |
| dG6P-sperm-$dT_{30}$-C3 | /5Hexynyl//Spermine/TTTTT TTTTT TTTTT TTTTT TTTTT TTTTT/3SpC3/ | 28 |
| dT6P-Cy3.5-$dT_{30}$-C3 | /5Hexynyl/iCy3.5/TTTTT TTTTT TTTTT TTTTT TTTTT TTTTT/3SpC3/ | 29 |
| dT6P-Cy3-Cy3-$dT_{30}$-C3 | /5Hexynyl/iCy3//iCy3/TTTTT TTTTT TTTTT TTTTT TTTTT/3SpC3/ | 30 |
| dT6P-$dT_6$-Cy3-$dT_{23}$-C3 | /5Hexynyl/TTTTT T/iCy3/TTTTT TTTTT TTTTT TTTTT TTT/3SpC3/ | 31 |
| dT6P-$dT_{10}$-Cy3-$dT_{19}$-C3 | /5Hexynyl/TTTTT TTTTT/iCy3/TTTT TTTTT TTTTT TTTTT/3SpC3/ | 32 |
| dT6P-Hairpin Block | /5Hexynyl/TT TTC GGC GCG TAA GCG CCG TTT TTT TTT TTT TTT TTT TTT TTT T/3SpC3/ | 33 |
| dC6P-Cy3 | DBCO-Cy3 | — |
| dG6P-Cy3 | DBCO-Cy3 | — |
| dT6P-$T_6$-$dSp_8$-$T_{16}$-C3 | /5Hexynyl/TTTTTT/idSp//idSp//idSp//idSp//idSp//idSp//idSp//idSp/TTTTT TTTTT TTTTT T/3SpC3/ | 34 |
| dA6P-Cy3-$T_{30}$-C6 | /5Hexynyl//iCy3/TTTTT TTTTT TTTTT TTTTT TTTTT TTTTT/3C6/ | 15 |
| dT6P-Cy3-$T_{30}$-C6 | /5Hexynyl//iCy3/TTTTT TTTTT TTTTT TTTTT TTTTT TTTTT/3C6/ | 15 |
| dC6P-Cy3-$T_{30}$-C6 | /5Hexynyl//iCy3/TTTTT TTTTT TTTTT TTTTT TTTTT TTTTT/3C6/ | 15 |
| dA6P-Cy3-$dT*_{30}$_ODD | /5Hexynyl//iCy3/T*TT*TT*TT*TT*TT*TT*TT*TT*TT*TT*TT*TT*TT*TT*T | 35 |
| dA6P-$T*_{30}$ | /5Hexynyl/T*T*T*T*T*T*T*T*T*T* T*T*T*T*T* T*T*T*T*T* T*T*T*T*T* T*T*T*T*T | 36 |

TABLE 4-continued

| Tagged Nucleotide Name | Tag Structure (including alkyne or cyclooctyne moiety) | SEQ ID No. |
|---|---|---|
| dA6P-Cy3-T*$_{30}$ | /5Hexynyl//iCy3/T*T*T*T*T* T*T*T*T*T* T*T*T*T*T* T*T*T*T*T* T*T*T*T*T* T*T*T*T*T | 37 |
| dG6P-Cy3-T$_{30}$-C3 | /5Hexynyl//iCy3/TTTTT TTTTT TTTTT TTTTT TTTTT TTTTT/3SpC3/ | 38 |
| dG6P-Cy3-T$_{15}$-C3 | /5Hexynyl//iCy3/TTTTT TTTTT TTTTT/3SpC3/ | 39 |
| dG6P-Cy3-T$_{20}$-C3 | /5Hexynyl//iCy3/TTTTT TTTTT TTTTT TTTTT/3SpC3/ | 40 |
| dG6P-Cy3-T$_{25}$-C3 | /5Hexynyl//iCy3/TTTTT TTTTT TTTTT TTTTT TTTTT/3SpC3/ | 41 |
| dA6P-Cy3 T2-Sp18-T$_{22}$-C3 | /5Hexynyl//iCy3/TT/iSP18/TTTTT TTTTT TTTTT TTTTT TT/3SpC3/ | 42 |
| dT6P-Cy3-dT4-dSp$_8$-T$_{18}$-C3 | /5Hexynyl//iCy3/TTTT/idSp//idSp//idSp//idSp//idSp//idSp//idSp//idSp/TTTTT TTTTT TTTTT TTT/3SpC3/ | 43 |
| dT6P-Hex-dT$_6$-dTC2NH$_6$-dT$_{18}$-C3 | /5Hexynyl/TTTTTT/iAmMC2T//iAmMC2T//iAmMC2T//iAmMC2T//iAmMC2T//iAmMC2T/TTTTT TTTTT TTTTT TTT/3SpC3/ | 44 |
| dA6P-Cy3-dT$_4$-Sp9-T$_{23}$-C3 | /5Hexynyl//iCy3/TTTT/iSP9/TTTTT TTTTT TTTTT TTTTT TTT/3SpC3/ | 45 |
| dC6P-Cy3-T-dSp$_3$-T$_{26}$-C3 | /5Hexynyl//iCy3/T/idSp//idSp//idSp/T TTTTT TTTTT TTTTT TTTTT TTTTT/3SpC3/ | 46 |
| dC6P-Cy3-T$_4$-dSp$_3$-T$_{23}$-C3 | /5HexynyllliCy3/TTTT/idSplliidSplliidSp/TTT TTTTT TTTTT TTTTT TTTTT/3SpC3/ | 47 |
| dC6P-Cy3-T$_7$-dSp$_3$-T$_{20}$-C3 | /5Hexynyl//iCy3/TTTTT TT/idSp//idSp/TTTTT TTTTT TTTTT/3SpC3/ | 48 |
| dC6P-Cy3-T$_{10}$-dSp$_3$-T$_{17}$-C3 | /5Hexynyl//iCy3/TTTTT TTTTT/idSp//idSp//idSp/TTTTT TTTTT TTTTT TT/3SpC3/ | 49 |
| dC6P-Cy3 T$_4$-iFluorT$_3$-T23-C3 | /5Hexynyl//iCy3/TTTT/iFluorT//iFluorT//iFluorT/TTT TTTTT TTTTT TTTTT TTTTT/3SpC3/ | 50 |
| dC6P-Cy3 T$_4$-iFluorT-T-iFluorT-T$_{23}$-C3 | /5Hexynyl//iCy3/TTTT/iFluorT/T/iFluorT/TTT TTTTT TTTTT TTTTT TTTTT/3SpC3/ | 51 |
| Bio-Spermine-dT$_{30}$-C3 | /5Hexynyl//Spermine/TTTTT TTTTT TTTTT TTTTT TTTTT TTTTT/3SpC3/ | 52 |
| dT6P-dT$_{30}$-Cy3-C3 | /5Hexynyl/TTTTT TTTTT TTTTT TTTTT TTTTT TTTTT/iCy3//3SpC3/ | 53 |
| dG6P-dT$_8$-Spermine-dT$_{20}$-C3 | /5Hexynyl/TTTTT TTT/Spermine/TTTTT TTTTT TTTTT TTTTT/3SpC3/ | 54 |
| dA6P-Cy3- T$_4$-iFluorT-T-iFluorT-T$_{23}$-C3 | /5Hexynyl//iCy3/TTTT/iFluorT/T/iFluorT/TTT TTTTT TTTTT TTTTT TTTTT/3SpC3/ | 51 |
| dT6P-CY3-dT4-Aptamer-dT25-C3 | /5Hexynyl//iCy3/TTT TGG TTG GTG TGG TTG GTT TTT TTT TTT TTT TTT TTT TT/3SpC3/ | 55 |
| dT6P-Cy3-dT4-12Hairpin-dT25-C3 | /5Hexynyl//iCy3/TTT TCC GGC GCG GCG CGT AAG CGC CGC GCC GGT TTT TTT TTT TTT TTT TTT TTT TTT /3SpC3/ | 56 |
| dT6P-Cy3-dT$_5$-dSp$_3$-dT$_{22}$-C3 | /5Hexynyl//iCy3/TTT TT/idSp//idSp//idSp/T TTT TTT TTT TTT TTT TTT TTT /3SpC3/ | 57 |
| dT6P-Cy3-dT$_6$-dSp$_3$-dT$_{21}$-C3 | /5Hexynyl//iCy3/TTT TTT /idSp//idSp//idSp/TTT TTT TTT TTT TTT TTT /3SpC3/ | 58 |
| dT6P-Cy3-dT4-dSp$_4$-dT$_{22}$-C3 | /5Hexynyl//iCy3/TTT T/idSp//idSp//idSp//idSp/TT TTT TTT TTT TTT TTT TT/3SpC3/ | 59 |
| dT6P-Cy3-dT4-dSp$_5$-dT$_{21}$-C3 | /5Hexynyl//iCy3/TTT T/idSp//idSp//idSp//idSp//idSp/T TTT TTT TTT TTT TTT TTT TT/3SpC3/ | 60 |
| dC6P-Cy3-dT$_5$-SpC12-dT$_{23}$-C3 | /5Hexynyl//iCy3/TTT TT /iSpC12/TTTTT TTTTT TTTTT TTTTT TTT/3SpC3/ | 61 |
| dC6P-Cy3-dT$_4$-SpC6-SpC6-dT$_{24}$-C3 | /5Hexynyl//iCy3/TTT T/iSpC6//iSpC6/T TTTTT TTTTT TTTTT TTTTT TTT/3SpC3/ | 62 |

TABLE 4-continued

| Tagged Nucleotide Name | Tag Structure (including alkyne or cyclooctyne moiety) | SEQ ID No. |
|---|---|---|
| dC6P-Cy3-dT$_4$-(SpC3)$_3$-dT$_{23}$-C3 | /5Hexynyl//iCy3/TTT T/iSpC3//iSpC3//iSpC3/TT TTT TTT TTT TTT TTT TTT TTT /3SpC3/ | 63 |
| dG6P-Cy3-dT$_{30}$-C3 | /5Hexynyl//iCy3/TTTTT TTTTT TTTTT TTTTT TTTTT TTTTT/3SpC3/ | 64 |
| dT6P-Cy3-dT$_2$-dSp$_8$-dT$_{20}$-C3 | /5Hexynyl//iCy3/TT/idSp//idSp//idSp//idSp//idSp//idSp//idSp//idSp/TTT TTT TTT TTT TTT TT/3SpC3/ | 65 |
| dC6P-Cy3-T$_{30}$-(C$_3$)$_4$-PO$_4$ | /5Hexynyl//iCy3/TTT TTT TTT TTT TTT TTT TTT TTT TTT TTT /iSpC3//iSpC3//iSpC3//iSpC3//3Phos/ | 66 |
| dC6P-Cy3-T$_{30}$-PO$_4$ | /5Hexynyl//iCy3/TTT TTT TTT TTT TTT TTT TTT TTT TTT TTT /3Phos/ | 67 |
| dC6P-Cy3-T$_{30}$-C3-NH$_2$ | /5Hexynyl//iCy3/TTT TTT TTT TTT TTT TTT TTT TTT TTT TTT /3Propylamine/ | 68 |
| dG6PαS-Cy3-dT$_2$-dSp$_8$-dT$_{20}$-C3 | /5Hexynyl//iCy3/TT/idSp//idSp//idSp//idSp//idSp//idSp//idSp//idSp/TTT TTT TTT TTT TTT TT/3SpC3/ | 69 |
| Rev-P-T$_{30}$-Cy3-dG6P | /5Phos/TTTTT TTTTT TTTTT TTTTT TTTTT TTTTT/iCy3//3'-propylamine/ + propargyl-propionamide | 70 |
| Rev-P-T$_{24}$-dSp$_3$-T$_3$-Cy3-dC6P | /5Phos/TTTTT TTTTT TTTTT TTTTT TTTTT TTTT /idSp//idSp//idSp/TTT/iCy3//3'-propylamine/ + propargyl-propionamide | 71 |
| dT6P-Cy3-dT$_4$-HP6-dT$_{25}$-C3 | /5Hexynyl//iCy3/TT TTC GGC GCG TAA GCG CCG TTT TTT TTT TTT TTT TTT TTT T/3SpC3/ | 72 |
| dT6P-Cy3-dC$_{30}$-C3 | /5Hexynyl//iCy3/CCCCCCCCCCCCCCCCCCCCCCCCCCCCCC/3SpC3/ | 73 |
| dA6P-Cy3-dT4-dI6-dT20-C3 | /5Hexynyl//iCy3/TTT T/ideoxyI//ideoxyI//ideoxyI//ideoxyI//ideoxyI//ideoxyI/TT TTT TTT TTT TTT TTT TTT /3SpC3/ | 74 |
| dA6P-Cy3-dT4-NitrIndole6-dT20-C3 | /5Hexynyl//iCy3/TTT T/i5NitInd//i5NitInd//i5NitInd//i5NitInd//i5NitInd//i5NitInd/TT TTT TTT TTT TTT TTT /3SpC3/ | 75 |
| dA6P-Cy3-dT4-dC6-dT20-C3 | /5Hexynyl//iCy3/TTTT CCCCCC TTTTT TTTTT TTTTT TTTTT/3SpC3/ | 76 |
| dA6P-Cy3-dT4-5IU6-dT20-C3 | /5Hexynyl//iCy3/TTT T/i5I-dU//i5I-dU//i5I-dU//i5I-dU//i5BI-dU//i5I-dU/TT TTT TTT TTT TTT TTT /3SpC3/ | 77 |
| dA6P-Cy3-dT4-PyrndU6-dT20-C3 | /5Hexynyl//iCy3/TTT T/i5Pyrene-dU/$_6$TT TTT TTT TTT TTT TTT /3SpC3/ | 78 |
| dT6P-Cy3-dT$_4$-(idSP-T)$_4$-dT$_{18}$-C3 | /5Hexynyl//iCy3/TTTT/idSp/T/idSp/T/idSp/T/idSp/TTT TTTTT TTTTT TTTTT/3SpC3/ | 79 |
| dT6P-Cy3-dT5-(idSP-T)$_4$-dT$_{17}$-C3 | /5Hexynyl//iCy3/TTTTT/idSp/T/idSp/T/idSp/T/idSp/TT TTTTT TTTTT TTTTT/3SpC3/ | 80 |
| dT6P-Cy3-dT$_4$-Propyl$_6$-dT$_{20}$-C3 | /5Hexynyl//iCy3/TTT T/iSpC3//iSpC3//iSpC3//iSpC3//iSpC3//iSpC3/TT TTT TTT TTT TTT TTT /3SpC3/ | 81 |
| dT6P-Cy3-LdT$_{30}$-C3 | /5Hexynyl//iCy3/($_L$dT)$_{30}$/3SpC3/ | 82 |
| dT6P-Cy3-LdT$_4$-dSp$_3$-LdT$_{23}$-C3 | /5Hexynyl//iCy3/($_L$dT)4/idSp//idSp//idSp/i($_L$dT)$_{23}$/3SpC3/ | 83 |
| dT6P-Cy3-LdT$_4$-dSp$_8$-LdT$_{18}$-C3 | /5Hexynyl//Cy3/($_L$dT)4/idSp//idSp//idSp//idSp//idSp//idSp//idSp//idSp/($_L$dT)$_{18}$/3SpC3/ | 84 |
| dT6P-Cy3-LdT4-dI$_6$-LdT$_{20}$-C3 | /5Hexynyl//iCy3/($_L$dT)4/ideoxyI//ideoxyI//ideoxyI//ideoxyI//ideoxyI//ideoxyI/ ($_L$dT)$_{20}$/3SpC3/ | 85 |
| dT6P-Cy3-dT$_4$-L111-dT$_{26}$-C3 | /5Hexynyl//iCy3/TTTT GGG T GGG T GGG T GGG TTTTTTTTTTTTTTTTTTTTTTTT/3SpC3/ | 86 |
| dT6P-Cy3-dT$_4$-L121-dT$_{26}$-C3 | /5Hexynyl//iCy3/TTTT GGG T GGG TT GGG T GGG TTTTTTTTTTTTTTTTTTTTTTT/3SpC3/ | 87 |
| dT6P-Cy3-dT$_4$- | /5Hexynyl//iCy3/TTTT /iSpC12//iSpC12/TTTTT TTTTT TTTTT TTTTT | 88 |

TABLE 4-continued

| Tagged Nucleotide Name | Tag Structure (including alkyne or cyclooctyne moiety) | SEQ ID No. |
|---|---|---|
| SpC12-SpC12-dT$_{24}$-C3 | TTTT/3SpC3/ | |
| dT6P-Cy3-dT$_3$-(SpC12)$_3$-dT$_{24}$-C3 | /5Hexynyl//iCy3/TTT /iSpC12//iSpC12//iSpC12/TTTTT TTTT TTTTT TTTTT TTTT/3SpC3/ | 89 |
| dT6P-Cy3-dT$_4$-(SpC6)$_4$-dT$_{25}$-C3 | /5Hexynyl//iCy3/TTTT/dSpC6//dSpC6//dSpC6//dSpC6/TTTTT TTTTT TTTTT TTTTT/3SpC3/ | 90 |
| dT6P-Cy3-dT$_4$-(SpC6)$_5$-dT$_{23}$-C3 | /5Hexynyl//Cy3/TTTT/dSpC6//dSpC6//dSpC6//dSpC6//dSpC6/TTT TTTTT TTTTT TTTTT/3SpC3/ | 91 |
| dT6P-Cy3-dT5-(SpC6)$_4$-dT$_{24}$-C3 | /5Hexynyl//iCy3/TTTTT/dSpC6//dSpC6//dSpC6//dSpC6/TTTTT TTTTT TTTTT TTTT/3SpC3/ | 92 |
| dT6P-Cy3-dT$_2$-(SpC6)$_5$-dT$_{25}$-C3 | /5Hexynyl//iCy3/TT/dSpC6//dSpC6//dSpC6//dSpC6//dSpC6/TTTTT TTTTT TTTTT TTTTT/3SpC3/ | 93 |
| dT6P-Cy3-dT$_4$-Spermine-dT$_{25}$-C3 | /5Hexynyl//iCy3/TTTT/Spermine/TTTTT TTTTT TTTTT TTTTT TTTTT/3SpC3/ | 94 |
| dT6P-Cy3-dT2-Spermine-dT$_{27}$-C3 | /5Hexynyl//iCy3/TT/Spermine/TTTTT TTTTT TTTTT TTTTT TTTTT TT/3SpC3/ | 95 |
| dT6P-Cy3-dT$_2$-Spermine-Spermine-dT$_{26}$-C3 | /5Hexynyl//iCy3/TT/Spermine//Spermine/TTTTT TTTTT TTTTT TTTTT TTTTT T/3SpC3/ | 96 |
| dT6P-Cy3-dT$_4$-Pyrn-dU-TT-Pyrn-dU-dT$_{22}$-C3 | /5Hexynyl//iCy3/TTT T/i5Pyrene-dU/TT/i5Pyrene-dU/ TTT TTT TTT TTT TTT TTT TTT T/3SpC3/ | 97 |
| dT6P-Cy3-dT$_4$-Tmp$_6$-dT$_{20}$-C3 | /5Hexynyl//iCy3/TTTT/dT(mp)//dT(mp)//dT(mp)//dT(mp)//dT(mp)//dT(mp)/TTTTTTTTTTTTTTTTTTTT/{Propyl-}/ | 98 |
| dT6P-Cy3-dT$_4$-Pyrrolidine$_6$-dT$_{20}$-C3 | /5Hexynyl//iCy3/TTTT /{Pyrrolidine}$_6$/TTTTT TTTTT TTTTT TTTTT/3SpC3/ | 99 |
| dT6P-Pyrrolidine-dT$_{30}$-C3 | /5Hexynyl//{Pyrrolidine}/TTTTT TTTTT TTTTT TTTTT TTTTT TTTTT /3SpC3/ | 100 |
| dT6P-Pyrrolidine-Pyrrolidine-dT$_{30}$-C3 | /5Hexynyl//{Pyrrolidine}//{Pyrrolidine}/TTTTT TTTTT TTTTT TTTTT TTTTT TTTTT /3SpC3/ | 101 |
| dT6P-Pyrrolidine$_3$-dT$_{30}$-C3 | /5Hexynyl//{Pyrrolidine}//{Pyrrolidine}//{Pyrrolidine}/TTTTT TTTTT TTTTT TTTTT TTTTT TTTTT/3SpC3/ | 102 |
| dT6P-SpC3-Cy3-dT$_{30}$-C3 | /5Hexynyl//iSpC3//iCy3/TTTTT TTTTT TTTTT TTTTT TTTTT TTTTT/3SpC3/ | 103 |
| dT6P-SpC3-SpC3-Cy3-dT$_{30}$-C3 | /5Hexynyl//iSpC3//iSpC3//iCy3/TTTTT TTTTT TTTTT TTTTT TTTTT TTTTT/3SpC3/ | 104 |
| dT6P-SpC6-Cy3-dT$_{30}$-C3 | /5Hexynyl//iSpC6//iCy3/TTTTT TTTTT TTTTT TTTTT TTTTT TTTTT /3SpC3/ | 105 |
| dT6P-Cy3-dT$_4$(alpha-dT)$_3$-dT$_{23}$-C3 | /5Hexynyl//iCy3/TTTT/alpha-dT//alpha-dT//alpha-dT/TTTTT TTTTT TTTTT TTTTT TTT/3SpC3/ | 106 |

Selected abbreviations
"DBCO" = dibenzylcyclooctyne
"*" = thiophosphate diester
"ODD" = thiophosphates only at odd-numbered linkages in sequence
"idSp" = furan amidite (abasic amidite)
"3C6" = 3'-hexanol
"Npy" = 3-nitropyrrole
"3SpC3" = 3'-propanol
"Neb" = nebularine
"iSp18" = polyethyleneglycol 18 atom length
"iSp9" = polyethyleneglycol 9 atom length
"UniAmM" = heptylamine amidite
"Pyrd" = pyrrolidine amidite"
"iAmMC6T" = aminohexyl dT amidite
"iFluorT" = fluorescein dT amidite
"iAmMC2T" = aminoethyl dT amidite TABLE 4-continued

| Tagged Nucleotide Name | Tag Structure (including alkyne or cyclooctyne moiety) | SEQ ID No. |
|---|---|---|

"iSpC12" = dodecyl amidite
"iSpC6" = hexyl amidite
"iSpC3" = propyl amidite
"dG6PaS" = Sp isomer of alpha-thio dG6P
"Rev" = oligonucleotide tag has 5'-phosphate and has alkyne group at its 3'-end
"HP6" = hairpin structure
"ideoxyI" = 2'-deoxyinosine
"i5NitInd" = 5-nitroindole
"i5I-dU" = 5-iodo deoxyuridine
"i5Pyrene-dU" = 5-pyrene-deoxyuridine
"$_L$dT" = L isomer of thymidine
"L111" = G-quadraplex structure
"L121" = G-quadraplex structure
"Pra" = propargylglycine
"Dab" = diaminobutyric acid
"U" = beta-alanine (in context of peptide tags)
"dT(mp)" = thymidine methyl phosphonate
"{pyrrolidine}" = pyrrolidine amidite
"alpha-dT" = alpha anomer of thymidine

Example 7

Synthesis of dT6P-DBCO-Cy3

Figure 22:
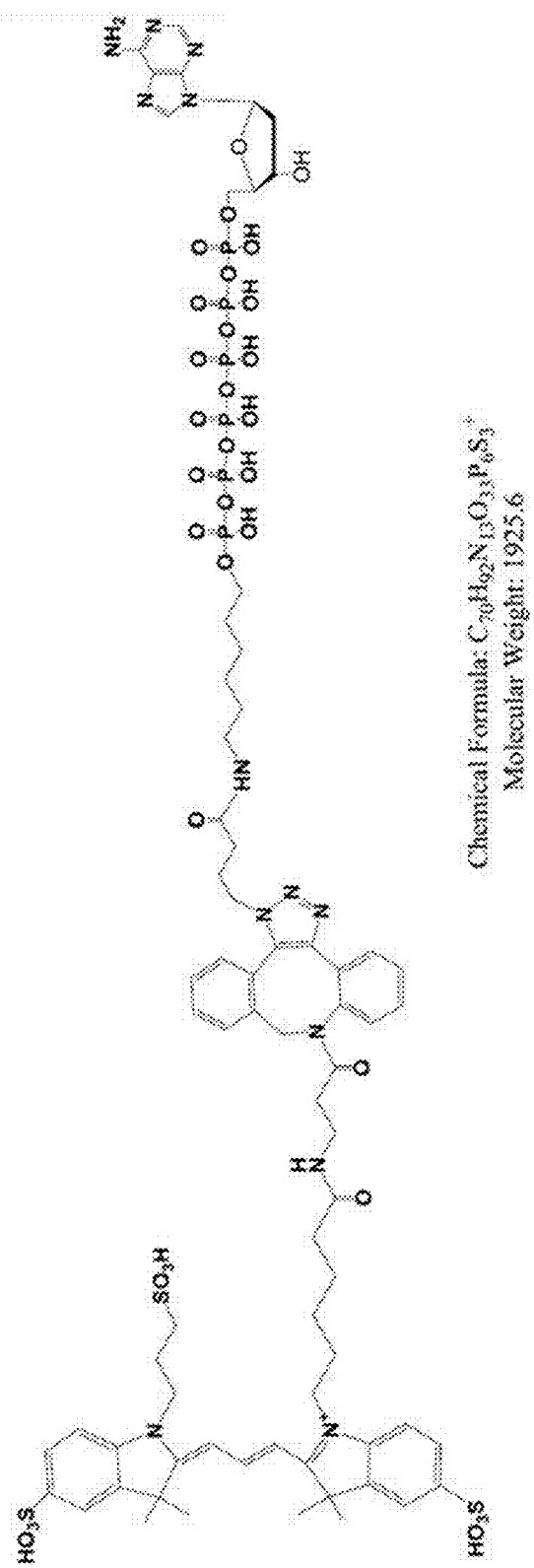
FIG. 22 shows the result of a click reaction between dA6P-N$_3$ and DBCO-Cy3.
Figure 23:
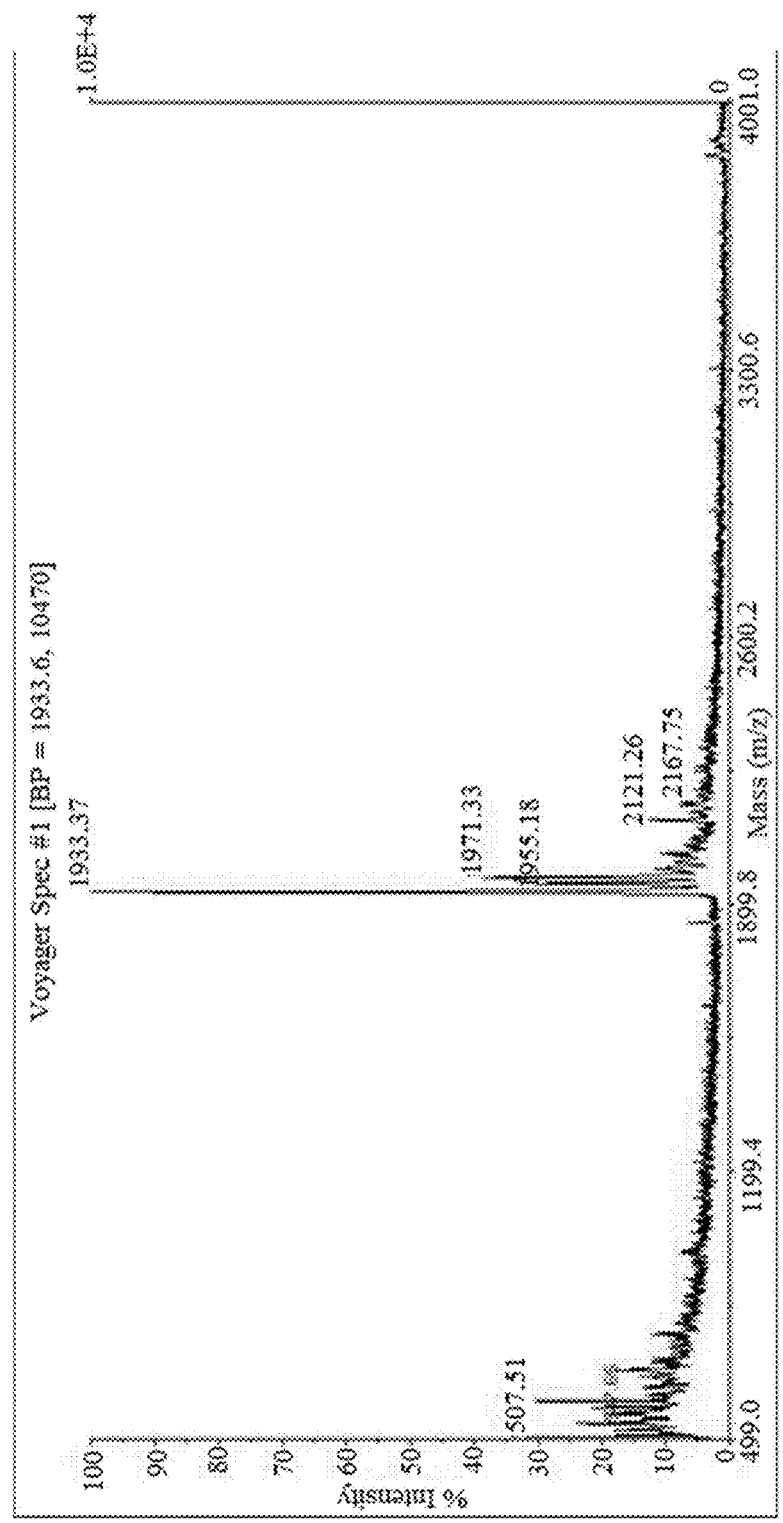
FIG. 23 shows a MALDI-TOF MS spectrum that indicates the conversion of azido-nucleotide to the product, DBCO-Cy3-dT6P.

FIG. 22 shows the result of a click reaction between dA6P-$N_3$ and DBCO-Cy3. In this example, dT6P-$N_3$ (500 nmol, 100 µl $H_2O$) and DBCO-Cy3 (700 nmol, 100 µl DMF) are mixed together and stirred at room temperature for 2 hours. FIG. 23 shows a MALDI-TOF mass spectrum that indicates the conversion of azido-nucleotide to the product, DBCO-Cy3-dT6P. The product is characterized by MALDI-TOF mass spectroscopy and single base extension reaction. The molecular weight is 1933 Daltons according to MALDI-TOF.

Example 8

Synthesis of dT6P-Cy3-dT$_{25}$

Figure 24:
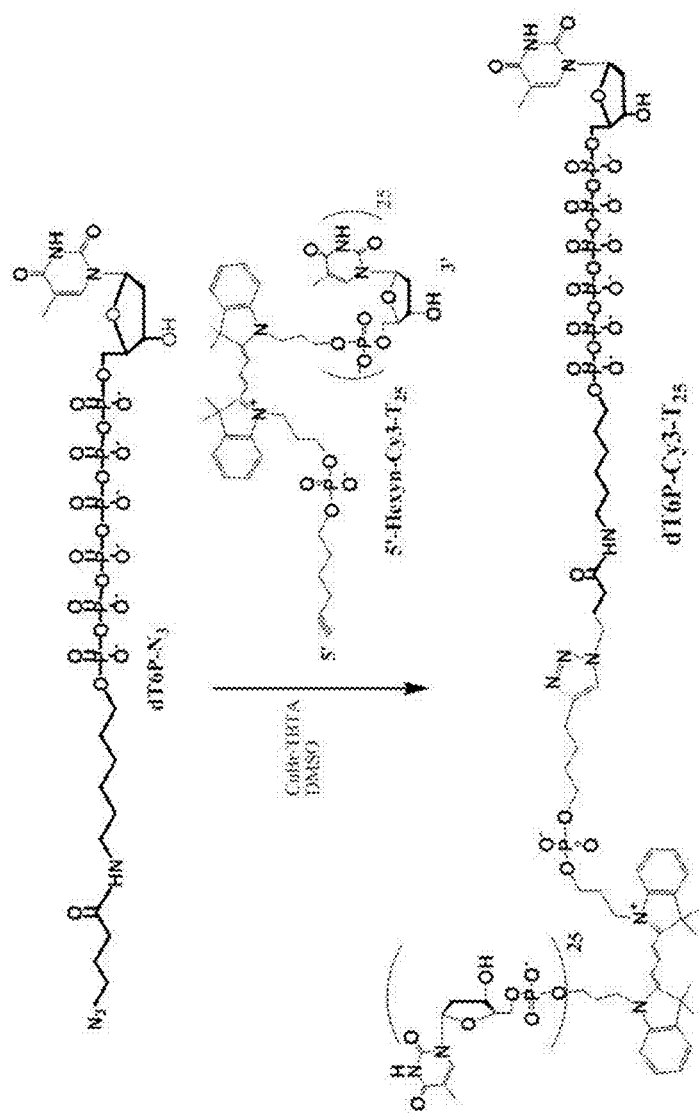
FIG. 24 shows a click reaction between dT6P-N$_3$ and Hexynyl-Cy3-T$_{25}$ oligonucleotide to form a dT6P-Cy3-T$_{25}$ tag.

FIG. 24 shows a click reaction between the 5'-azido-hexaphosphate-nucleotide, dT6P-$N_3$ and the 5'-alkyne-oligonucleotide tag, 5'-Hexynyl-Cy3-$T_{25}$ to form the tagged nucleotide, dT6P-Cy3-$T_{25}$. A solution of dT6P-$N_3$ (750 nmol) is added to 5'-Hexynyl-Cy3-$T_{25}$ oligonucleotide (obtained from TriLink, 500 nmol in 200 µl $H_2O$), followed by the addition of copper bromide (50 µl, 0.1 M solution in 3:1 DMSO/t-BuOH) and TBTA (100 µl, 0.1 M solution in 3:1 DMSO/t-BuOH). The reaction mixture is stirred at 40° C. for 16 hours. Purification is performed by HPLC using 0.1 M TEAC buffer (pH 7.5) and acetonitrile gradient. The tagged-nucleotide product, dT6P-Cy3-$T_{25}$ is characterized by MALDI-TOF mass spectroscopy and single base extension reaction. MALDI-TOF indicates a mass of 9179 Daltons.

Example 9

Synthesis of 2'-Deoxythymidine-5'-hexaphosphate-azide (dT6P-$N_3$)

Synthesis of Fmoc-6-aminohexyltriphosphate: Fmoc-6-aminohexanol (1 g, 2.94 mmol) is co-evaporated with anhydrous acetonitrile (2×20 ml) and then dissolved in triethylphosphate (10 ml). Phosphorous oxychloride (550 µl, 5.88 mmol) is added to this solution once cooled and stirred for 2 hours. To the reaction mixture, tributylammonium pyrophosphate (5 equivalents, 15 mmol, 0.5 M solution in anhydrous DMF) is added and stirred for 20 minutes. The solution is quenched with 0.1 M triethylammonium bicarbonate buffer (200 ml, pH 7.5) and adjusted to pH ~7. This solution is loaded on a Sephadex A-25 column and purified using 0.1 M to 1.0 M TEAB buffer (pH 7.0) gradient. The appropriate fractions are pooled and further purified on HPLC to provide pure triphosphate, $^{31}$P-NMR ($D_2O$) δ −10.5 (d, 2P), −22.84 (t, 1P).

Synthesis of dT6P-$NH_2$: Fmoc-aminohexyltriphosphate (200 mg, 0.35 mmol) is co-evaporated with anhydrous acetonitrile (2×10 ml) and then dissolved in anhydrous DMF (3 ml). Carbonyldiimidazole (CDI) (4 equivalents, 1.4 mmol) is added and stirred at room temp for 4 hours. Methanol (6 equivalents, 85 ml) is added and further stirred for 30 minutes. To this, a solution of 2'-deoxythymidine-5'-triphosphate (dTTP, triethyl or tributylammonium salt, 0.4 mmol) in DMF and $MgCl_2$ (10 equivalent, 3.5 mmol) is added. The reaction mixture is stirred for 18 hours followed by the addition of 10% triethylamine in water (25 ml) to hydrolyze the Fmoc group. The reaction mixture is stirred further for 16 hours and the precipitated solid is filtered and the solution extracted with ether. The aqueous layer is concentrated and purified on HPLC using 0.1 M TEAC buffer (pH 7.5) and acetonitrile gradient. This is characterized by $^{31}$P NMR and mass spectroscopic data. $^{31}$P-NMR: d−10.63 (bs, 1P), −11.65 (bs, 1P), −23.35 (bm, 4P).

Synthesis of dT6P-$N_3$: The prepared dT6P-$NH_2$ (10 µmol) is dissolved in 0.1 M bicarbonate-carbonate buffer (500 pH 8.7) and azidobutyric acid-NHS (25 µmol) in 200 µl DMF is added. The reaction mixture is stirred overnight. The reaction mixture is purified by HPLC using 0.1 M TEAC buffer (pH 7.5) and acetonitrile gradient.

Example 10

Figure 25:
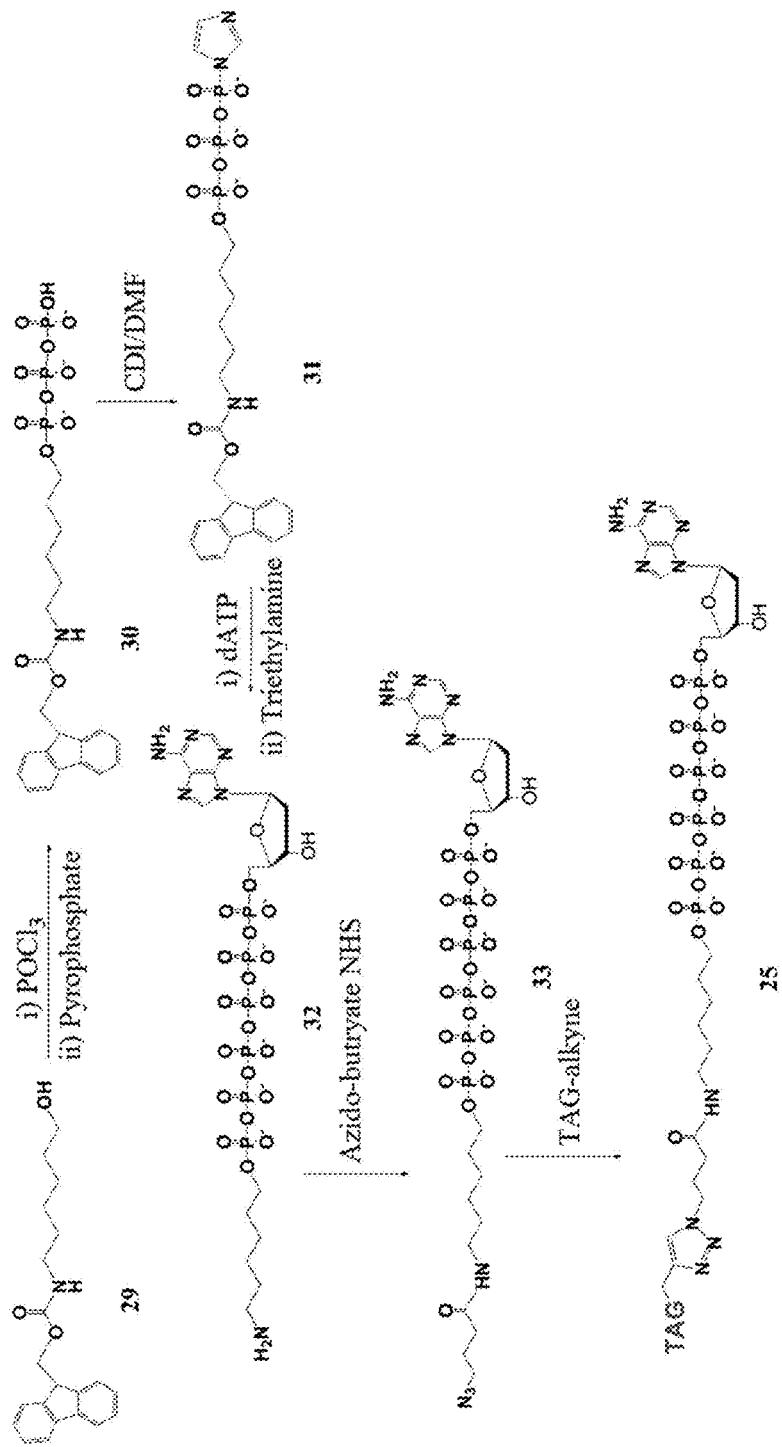
FIG. 25 shows examples of the synthesis of 2'-Deoxy-adenosine-5'-hexaphosphate and attachment of a tag to the terminal phosphate using click chemistry.

Synthesis of 2'-Deoxyadenosine-5'-Hexaphosphate and Attachment of Tag to the Terminal Phosphate Using Click Chemistry This example illustrates the general synthetic scheme for making a tagged nucleotide using a alkyne-azido cycloaddition click reaction. FIG. 25 shows the synthesis of 2'-deoxyadenosine-5'-hexaphosphate ("dA6P") and attachment of a tag to the terminal phosphate using the azide-alkyne click chemistry. Following the reaction arrows from beginning to end, reagents include (i) POCl$_3$ and pyrophosphate, (ii) CDI and DMF, (iii) dATP, (iv) triethylamine and azidobutyrate NHS, and (v) TAG-alkyne.

As shown in FIG. 25, the synthesis of a tagged nucleotide, exemplified here for a tagged dATP (25), starts with 6-Fmoc-aminohexanol (29), which reacts with phosphorus oxychloride (POCl$_3$) and pyrophosphate with triethyl phosphate as solvent at 0° C. to form 6-aminohexyltriphosphate (30). The 6-aminohexyltriphosphate is activated by N, N carbonyl diimidazole (CDI) forming compound (31), which reacts with the dATP to obtain the respective aminohexyl-dA6P (32). Then, the modified dA6P reacts with azido-butyric acid-NHS to afford derivatives containing an azido group (33). Finally, the azido derivatives and hexyne-derivatized tag (TAG-alkyne) react to obtain the target tagged nucleotide TAG-dA6P (25) through an alkyne-azido cycloaddition click reaction.

Example 11

Click Reaction Between dT6P-N3 and Oligo-Alkyne

Figure 26:
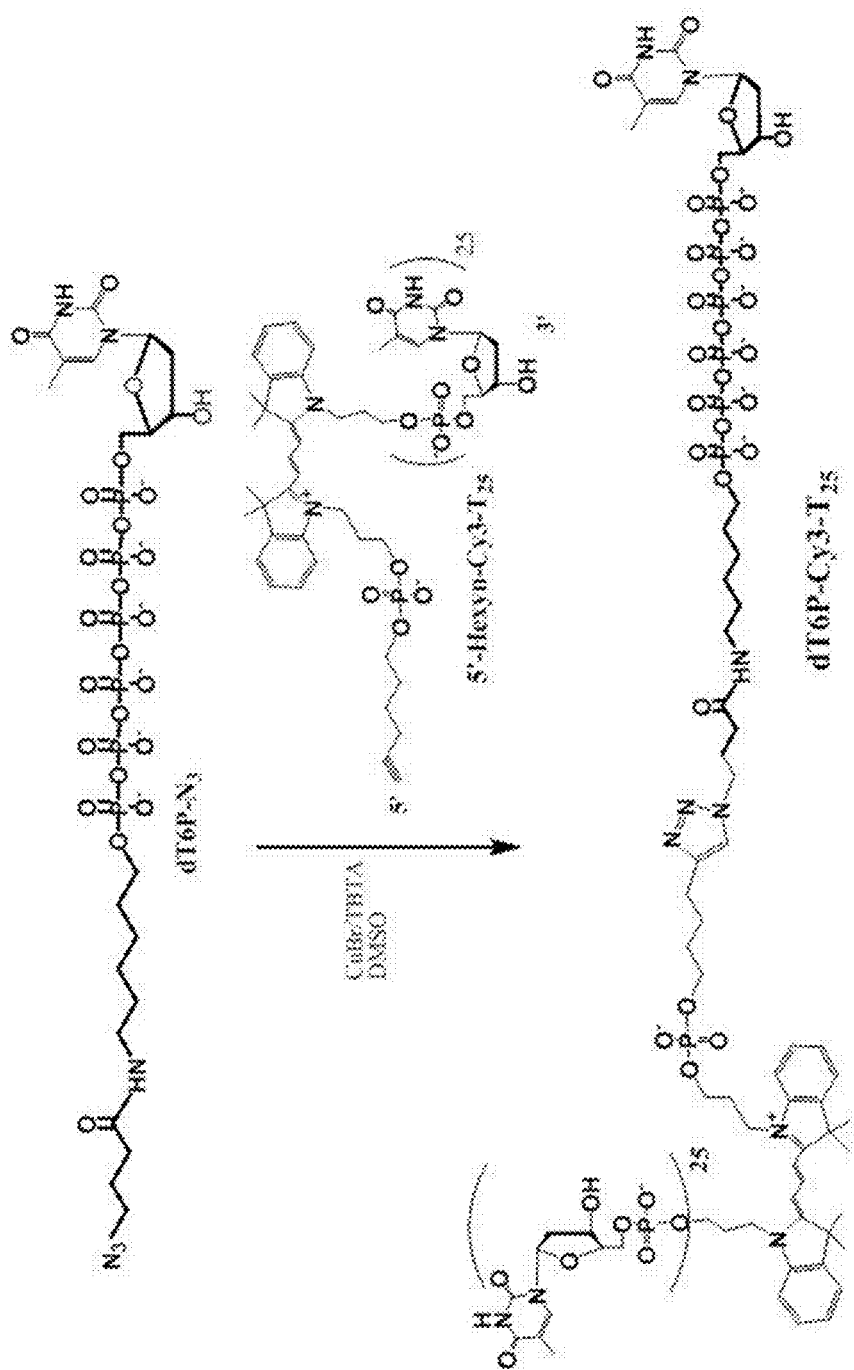
FIG. 26 shows an example of a click reaction between dT6P-N3 and Oligo-Alkyne.

FIG. 26 shows an example of a click reaction between the 5'-azido-hexaphosphate-nucleotide, dT6P-N$_3$ and the 5'-alkyne-oligonucleotide tag, 5'-Hexyn-Cy3-T$_{25}$. The reaction starts with dT6P-N$_3$ to which 5'-Hexyn-Cy3-T$_{25}$ is added in the presence of CuBr/TBTA and DMSO to form dT6P-Cy3-T$_{25}$.

Example 12

Example of Thiol-Thiol (S—S) Coupling

Figure 27:
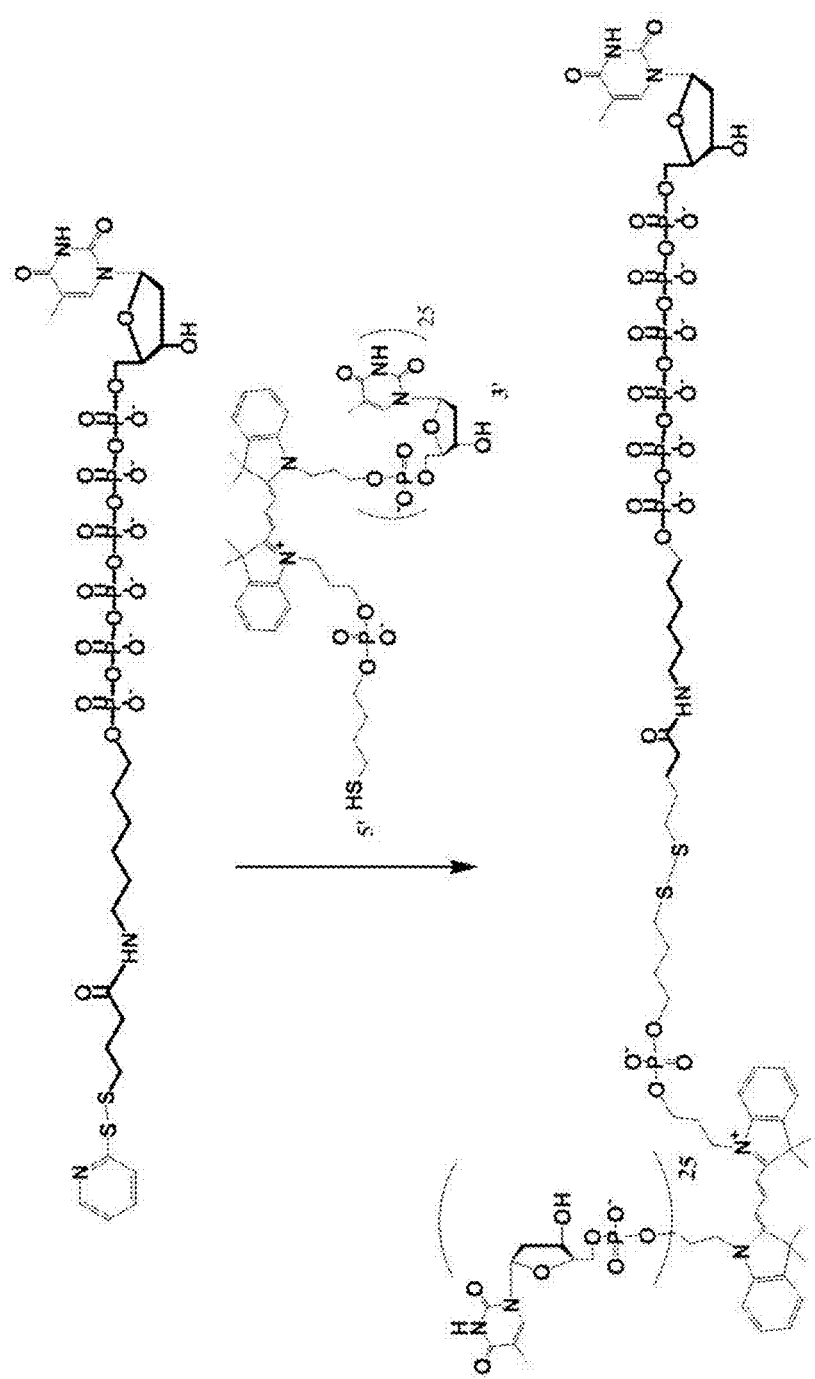
FIG. 27 shows an example of a thiol (disulfide bond) coupling of a tag to a nucleotide.

FIG. 27 shows an example of a thiol (disulfide bond) coupling of a tag to a nucleotide.

Example 13

DNA Polymerase Primer-Extension Reaction Using Tagged Nucleotides

Figure 28:
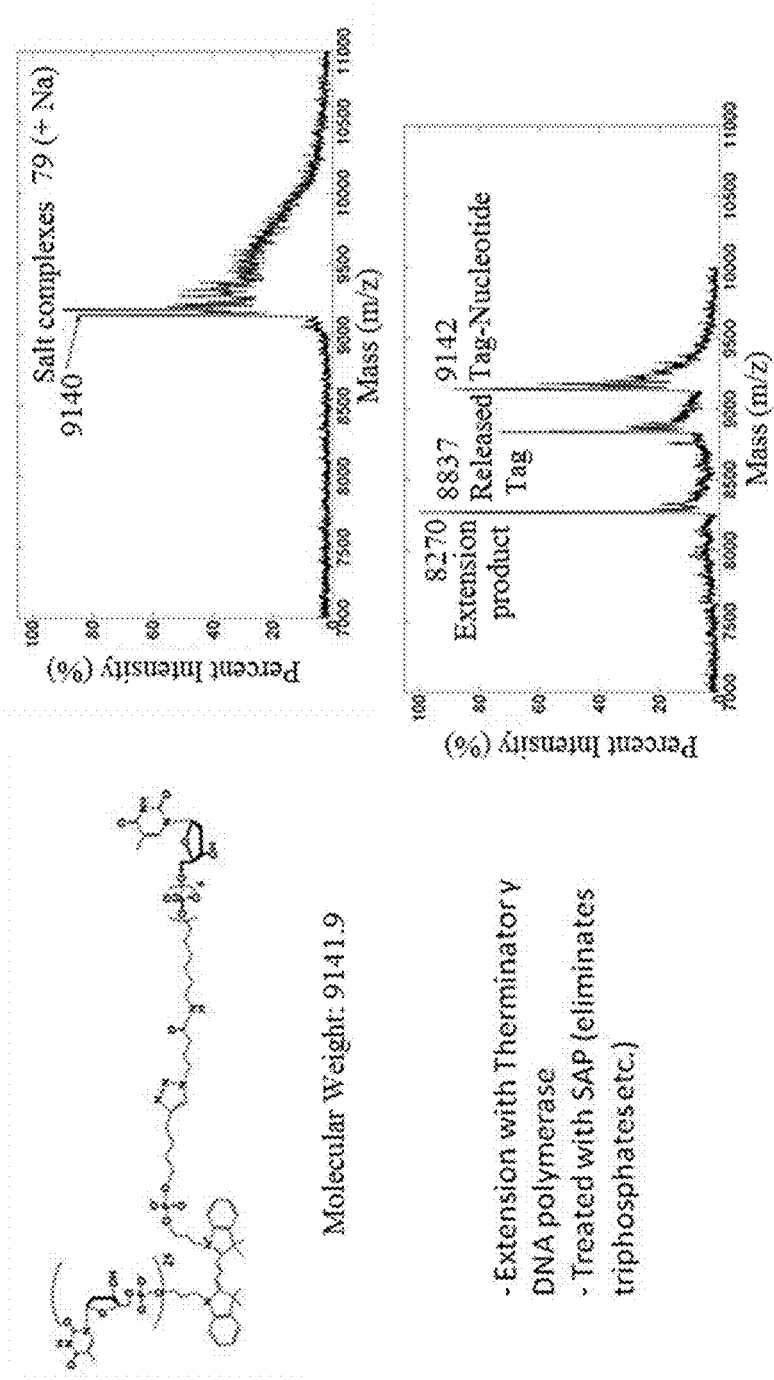
FIG. 28 shows mass spectra of Tag-Nucleotide dT6P-Cy3-T$_{25}$ and an extension reaction.

FIG. 28 shows an example of DNA polymerase extension reaction using tagged-nucleotide hexaphosphates. Extension reactions are carried out using a template-loop primer in which the next complementary base on the template is either A, G, C, or T, allowing extension by a single complementary nucleotide base. Each extension reaction is carried out in a thermal cycler at 65° C. for 25 minutes in 20 µl reactions consisting of 3 µM template-loop primer, 2 units of Therminator γ DNA polymerase or Bst2.0 DNA polymerase (New England Biolabs) and 15 µM of one of the oligonucleotide-tagged-dN6P nucleotides. The DNA extension products are precipitated with ethanol, purified through C18 ZipTip columns (Millipore), and characterized by MALDI-TOF MS analysis. As shown in FIG. 28, there is 100% extension of the primer (mol. Wt. 7983) with the addition of next nucleotide TMP from the dT6P-Cy3-T$_{25}$ tagged nucleotide (mol. wt. 8270). The other two peaks on the MALDI-TOF MS are the intact tagged-nucleotide (mol. wt. 8837) and the released product from the extension reaction (mol. wt. 9142). FIG. 29 shows examples of monomers that can be incorporated into oligonucleotides using amidite chemistry.

Example 14

Synthesis and Characterization of 5'-Oligonucleotide-Cy3-Tagged Nucleotides

This example illustrates the synthesis of four different tags comprising oligonucleotides 5'-linked to a Cy3 moiety and covalently coupled to the terminal phosphate of four different nucleotide hexaphosphates, and the characterization of these tagged nucleotides in polymerase extension reactions.

Figure 30:
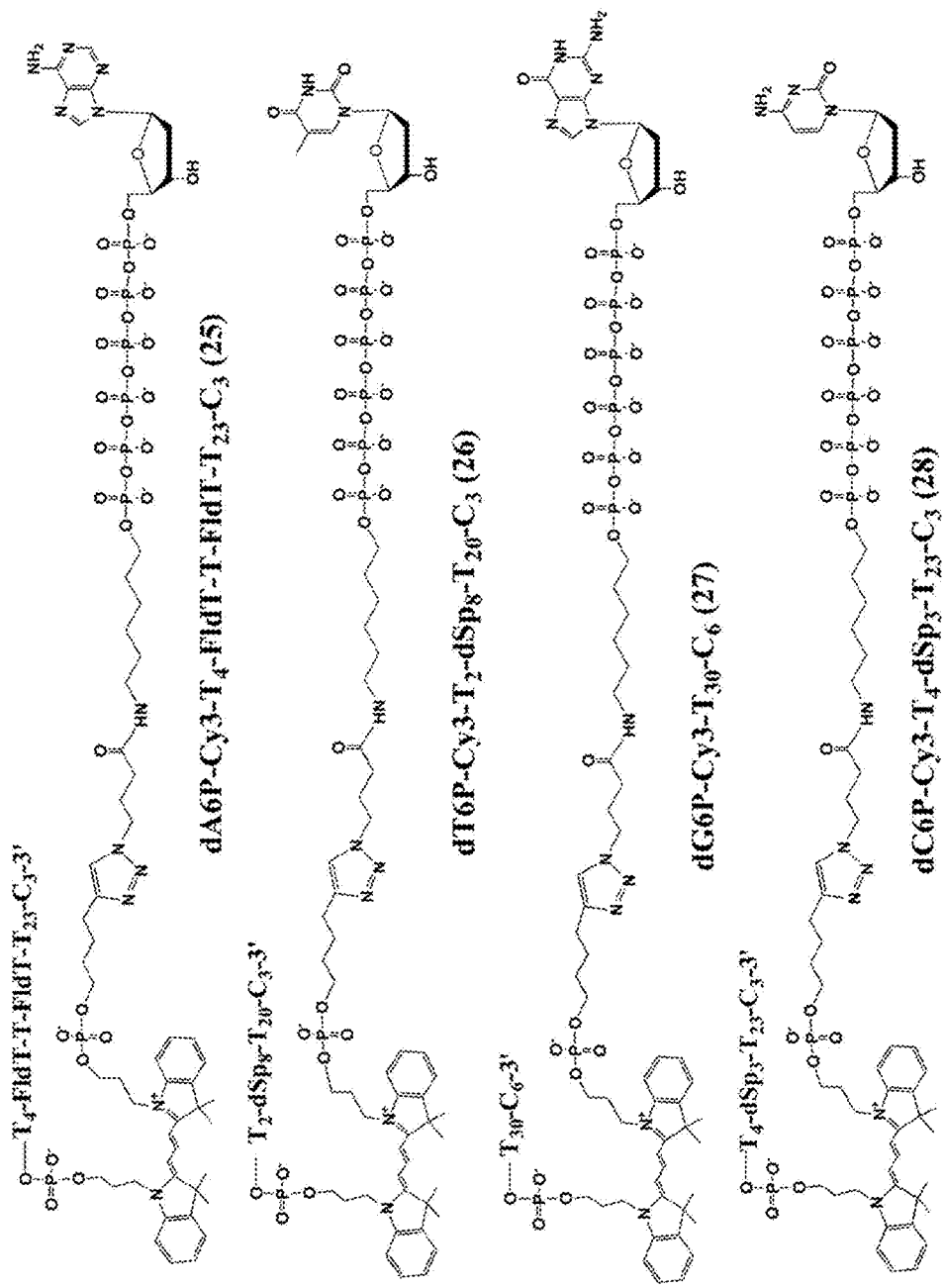
FIG. 30 shows four different tagged nucleotides prepared using azido-alkyne click chemistry and which comprise four different oligonucleotide-Cy3 tags.

The four tagged 2'-deoxy-5'-hexaphosphate nucleotides prepared and characterized in this example were: dA6P-Cy3-T4-FldT-T-FldT-T$_{23}$-C$_3$, dT6P-Cy3-T2-dSp$_8$-T$_{20}$-C$_3$, dG6P-Cy3-T$_{30}$-C$_6$, and dC6P-Cy3-T$_4$-dSp3-T$_{23}$-C$_3$. As shown in FIG. 30, each oligonucleotide tag is about 30 bases long and includes dT nucleotide units and a mix of spacers and modified bases. These differences in the oligonucleotide tags are designed to create size and charge differences at the constriction site in the nanopore and thereby provide unique current blockage characteristics under applied voltage to the nanopore. For example, the abasic dSp$_3$ and dSp$_8$ spacer residues have a smaller diameter than nucleotides in ssDNA, while the attached fluorescein on thymidines in the FldT-T-FldT tags have a larger diameter.

Synthesis of Oligonucleotide-Cy3-Tagged Nucleotides

Following the general reaction scheme shown in FIG. 25, 6-Fmoc-aminohexanol (29, 1 g, 2.94 mmol) was coevaporated with anhydrous acetonitrile (2×20 ml) and then dissolved in triethyl phosphate (10 ml). To this cooled and stirred solution was added fresh distilled phosphorous oxychloride (550 µl, 5.88 mmol) and the mixture stirred for 2 hr at 0° C. Tributylammonium pyrophosphate (5 eq., 15 mmol, 0.5 M solution in anhydrous DMF) and tributylamine (15 mmol) were added and the mixture was stirred for 20 min. The solution was quenched with 0.1 M triethylammonium bicarbonate buffer (TEAB, 200 ml, pH7.5) and adjusted to pH~7. This solution was loaded on a Sephadex A-25 column and eluted using 0.1 M to 1.0 M TEAB buffer (pH 7.0) gradient. The appropriate fractions were pooled and further purified on reverse phase HPLC on SUPELCOSIL™ LC-18-T (Supelco) 3 µM, 15 cm×4.6 mm. Mobile phase: A, 8.6 mM Et$_3$N, 100 mM HFIP in water at pH 8.1; B, 100% methanol. Started from 100% A/0% B to 0% A/100% B in 40 minutes. The pure triphosphate, $^{31}$P-NMR (D$_2$O) δ: −7.68 (d, 1P), −10.5 (d, 1P), −22.65 (t, 1P). The Fmoc-aminohexyltriphosphate produced (30, 200 mg, 0.35 mmol) was coevaporated with anhydrous acetonitrile (2×10 ml) and then dissolved in anhydrous DMF (3 ml). CDI (4 eq., 1.4 mmol) was added and the solution stirred at room temp for 4 hr. Methanol (6 eq., 85 µl) was added and further stirring was carried out for 30 min. To the above product (31), a solution of the desired 2'-deoxynucleoside-5'-triphosphate (dNTP, tributylammonium salt, 0.5 mmol) in DMF and MgCl$_2$ (10 equivalents, 3.5 mmol) was added. The reaction mixture was stirred for 18 hr followed by the addition of 10% triethylamine in water (25 ml) to hydrolyze the Fmoc group and yield the dN6P-NH$_2$ (32). The reaction mixture was stirred further for 16 hr and the precipitated solid was filtered and the solution extracted with ether. The aqueous layer was concentrated and purified on reverse phase HPLC. The product dN6P-NH$_2$ product was characterized by $^{31}$P-NMR: δ −10.63 (bs, 1P), −11.65 (bs, 1P), −23.35 (bm. 4P). MALDI-TOF MS data (not shown): dA6P-NH$_2$ (31); 832.02 (calculated 829), dT6P-NH$_2$ (not shown); 825.97

(calculated 820), dG6P-NH$_2$ (not shown); 848.33 (calculated 845), dC6P-NH$_2$ (not shown); 826.08 (calculated 828.0).

The azide (33) of the dN6P-NH2 (32, 10 μmol) was prepared by dissolving 32 in 0.1 M bicarbonate-carbonate buffer (500 μl, pH 8.7) and azidobutyric acid-NHS (25 mop in 200 μl DMF was added. The reaction mixture was stirred overnight and purified by HPLC using 0.1 M TEAA buffer (pH 7.5) and an acetonitrile gradient. MALDI-TOF MS data (not shown): dA6P-N$_3$ (33); 963.75 (calculated 963.3 as Na$^+$ salt), dT6P-N$_3$; 934.58 (calculated 932.3), dG6P-N$_3$; 960.27 (calculated 957.4), dC6P-N$_3$; 919.09 (calculated 917.4).

To 5'-hexynyl-modified oligonucleotide tag (obtained from TriLink, 500 nmol in 200 μl H$_2$O) a solution of dN6P-N$_3$ (33) (750 nmol) was added followed by the addition of copper bromide (50 μl, 0.1 M solution in 3:1 DMSO/t-BuOH) and TBTA (100 μl, 0.1 M solution in 3:1 DMSO/t-BuOH). The reaction mixture was stirred at 40° C. for 16 hr followed by HPLC purification using 0.1 M TEAA buffer (pH 7.5) and an acetonitrile gradient, and the oligonucleotide tagged-nucleotide (see FIG. 30, (25)-(28)) was characterized by MALDI-TOF MS and extension reaction. MALDI-TOF MS data (FIG. 31B): dA6P-Cy3-T$_4$-FldT-T-FldT-T$_{23}$-C3 (25): 11834 (calculated 11835); dT6P-Cy3-T$_2$-dSp$_8$-T$_{20}$-C$_3$ (26): 9806 (calculated 9808); dG6P-Cy3-T$_{30}$-C$_6$ (27): 10825 (calculated 10826); and dC6P-Cy3-T$_4$-dSp$_3$-T$_{23}$-C$_3$ (28): 10418 (calculated 10413).

For samples (25, 26, 27, 28, 32 and 33), the following HPLC method was carried out on SUPELCOSIL™ LC-C18-T (Supelco) 3.0 μm particle size, 15 cm×4.6 mm with 100% A/0% B in 4 min, then linear gradient change to 70% A/30% B for 30 minutes, and finally 0% A and 100% B for another 45 min at room temperature at a flow rate of 1 ml/min. (Mobile phase: A, 0.1 M TEAA; B, 100% ACN).

DNA Polymerase Extension Reactions

Screening for polymerase extension reaction activity with these four oligo dN6Ps as substrates identified Bst2.0 DNA polymerase (Bst2.0 DNAP) as capable to carry out primer extension quickly and precisely at room temperature. Additionally, Bst2.0 DNAP had the added advantage of lacking 3' to 5' exonuclease activity.

DNA polymerase extension reactions were performed using these four oligonucleotide-Cy3-tagged nucleotides, Bst2.0 DNAP, and "SimpleBell" primer-loop-template DNA (5'-GCG CTC GAG ATC TCC TCG TAA GAG GAG ATC TCG AGC GCA CTG ACT GAC TGA CCT CAG CTG CAC GTA AGT GCA GCT GAG GTC AG-3') (SEQ ID NO: 107). Each reaction was carried out at 65° C. for 30 minutes in 20 μL reactions consisting of 1.5 μM template-loop-primer, 1× isothermal amplification buffer [20 mM Tris-HCl, 10 mM (NH$_4$)$_2$SO4, 50 mM KCl, 2 mM MgSO$_4$, 0.1% Tween® 20, pH 8.8 @ 25° C.], 4 units of Bst2.0 DNAP, 2.25 μM natural dNTPs or 3.75 μM oligonucleotide-tagged nucleotides, with or without 1 mM MnSO$_4$. The DNA extension products were denatured at 95° C. for 5 minutes and then fast cooled to 4° C. The denatured extension products were separated in 15% TBE-Urea Precast Gels (Bio-Rad) under 250 mV for 25 minutes.

Results

Figure 31:
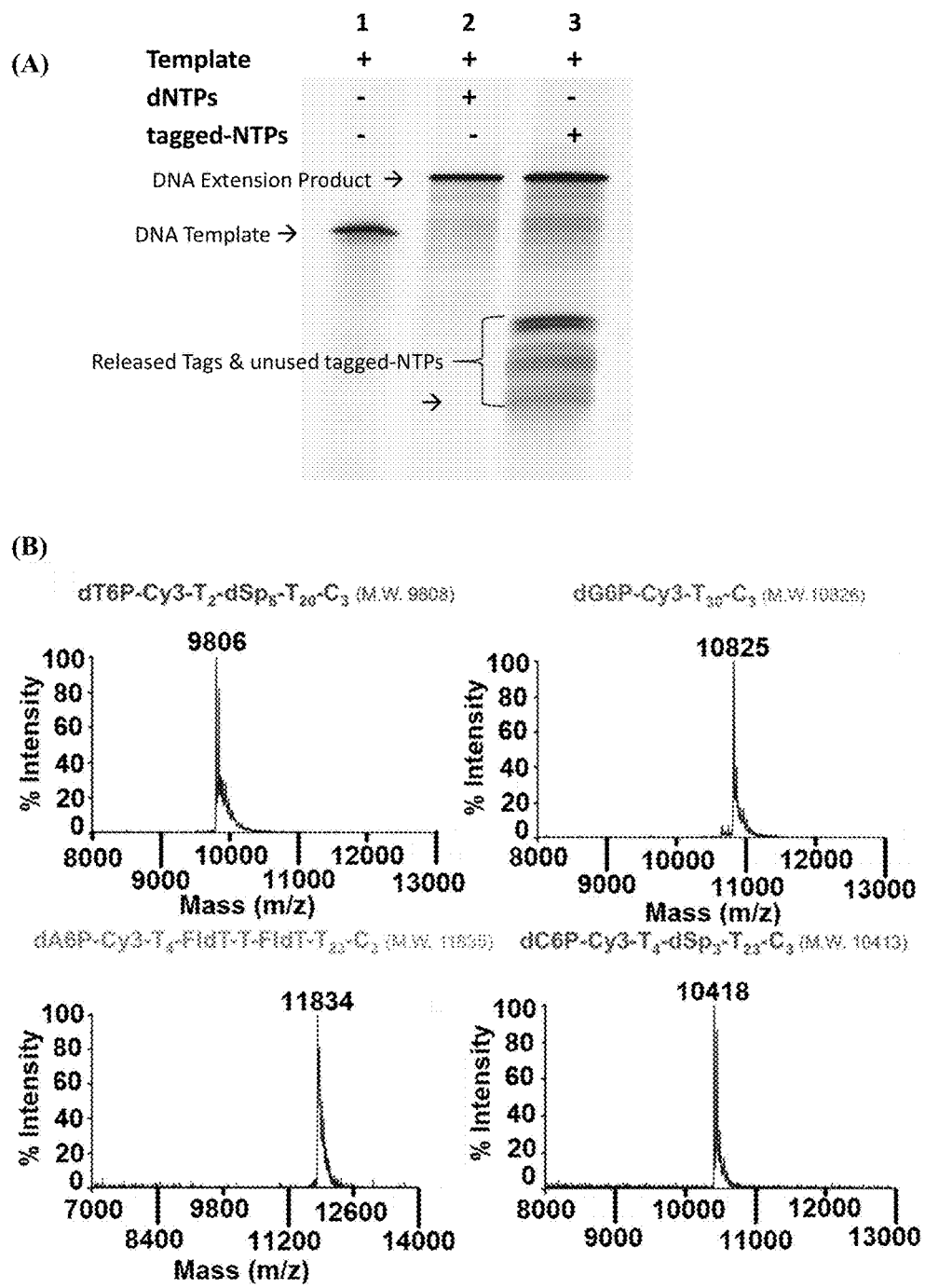
FIG. 31 depicts (A) denaturing gel images of samples from DNA polymerase extension reactions using four different tagged nucleotides which comprise different oligo-nucleotide-Cy3 tags, and which reactions carried out using Bst2.0 DNA polymerase; and (B) MALDI-TOF MS analysis of the four different oligonucleotide-Cy3 tagged nucleotides used in the reactions.

The DNA polymerase extension products were separated on a denaturing gel and the gel image is shown in FIG. 31A. Lane 1 shows a negative control using only the primer-loop-template DNA, lane 2 is a positive control following addition of the four natural dNTPs, and lane 3 is the extension reaction using the four oligonucleotide-Cy3-tagged nucleotides. The similar extension results in lanes 2 and 3 demonstrate that the primer-loop-template can be successfully extended by 48 bases using only the tagged nucleotides and Bst2.0 DNAP. The release of the oligonucleotide tags during the reaction, was demonstrated by the observation of the lower bands in lane 3.

The oligonucleotide tagged dN6Ps also were purified and measured by MALDI-TOF MS and their observed molecular weights correlated with the calculated numbers for each (see FIG. 31B).

The results demonstrate that the Bst2.0 polymerase is capable of carrying out full extension reactions with the four oligonucleotide-tagged nucleotide hexaphosphate substrates that were synthesized via an azido-alkyne click reaction that produces a triazole covalently coupling between the tag and the terminal phosphate.

Example 15

Exonuclease Protection of Oligonucleotide Tags with 3'-Modification

This example illustrates how oligonucleotide tags useful for tagging nucleotides in the embodiments of the present disclosure can be protected from exonuclease activity by chemical modification of the 3'-hydroxyl. Briefly, oligonucleotides with varying 3'-modifications were prepared, then incubated with Phi29 DNA polymerase (which has significant exonuclease activity), and the incubated samples analyzed by SDS-PAGE and HPLC to detect exonuclease degradation of the oligonucleotides.

Materials and Methods:

Oligonucleotide chains of dT nucleotides with 5'-biotin and various 3'-chemical modifications, as shown in Table 5 below, were prepared using standard oligonucleotide synthesis techniques.

TABLE 5

| Abbreviated Tag Name | Tag Structure | SEQ ID NO: |
|---|---|---|
| T$_{30}$ | /5Biosg/TT TTT TTT TTT TTT TTT TTT TTT TTT T | 108 |
| dSp | /5Biosg/TT TTT TTT TTT TTT TTT TTT TTT TTT T/3dSp/ | 109 |
| Phos | /5Biosg/TT TTT TTT TTT TTT TTT TTT TTT TTT T/3Phos/ | 110 |
| C3 | /5Biosg/TT TTT TTT TTT TTT TTT TTT TTT TTT T/3SpC3/ | 111 |
| C6 | /5Biosg/TT TTT TTT TTT TTT TTT TTT TTT TTT T/3SpC6/ | 112 |
| dSpC3 | /5Biosg/TTTTTTT TTT TTT TTT TTT TTT TTT T/dSp//3SpC3/ | 113 |

TABLE 5-continued

| Abbreviated Tag Name | Tag Structure | SEQ ID NO: |
|---|---|---|
| Tmp | /5Biosg/TTT TTT TTT TmpTmpTmp TTT TmpTmpTmp TTT TTT TTT TTT | 114 |

The various chemical modifications listed in the oligonucleotide structures of Table 5 are described in Table 6 below.

The oligonucleotide/exonuclease reaction samples were prepared as follows: 1 μL oligonucleotide (200 μM concentration), 5 units of Phi29 DNA polymerase (New England

TABLE 6

| Abbreviation | Chemical Modification |
|---|---|
| /Biosg/ | (structure of biotin with DMTr-protected amine linker connected via amide to hexyl phosphoramidite with N(Pr)$_2$ and O—CNEt groups) |
| /dSp/ | (5′-O-tetrahydrofuran-3′-O-phosphate abasic spacer structure) |
| /SpC3/ | 5′—O—CH$_2$CH$_2$CH$_2$—OH |
| /SpC6/ | 5′—O—(CH$_2$)$_6$—OH |
| /Tmp/ | (thymidine with R—O—5′, 3′-O-methylphosphonate linkage: O=P(CH$_3$)—O—R) |
| /Phos/ | (nucleotide with R—O—5′, base B, 3′-O-phosphate: O=P(O)—O) |

Biolabs, Ipswich, Mass., USA), and 1 μL 10×Phi29 Reaction Buffer (New England Biolabs, Ipswich, Mass., USA) (50 mM Tris-HCl, pH 7.5, 10 mM MgCl$_2$, 10 mM (NH$_4$)$_2$SO$_4$ and 4 mM DTT) were combined in 10 μL volume of buffer. This reaction sample was incubated for 15 min at 37 C. The reaction was stopped by adding 5 μL of PAGE loading dye (50% glycerol, 50 mM EDTA, 0.01% bromophenol blue). A 3 μL aliquot of the stopped reaction sample was loaded on a. 15% polyacrylamide gel containing 50% urea and buffered with TBE (MiniPROTEAN, Bio-Rad; Hercules, Calif., USA). Oligonucleotide products were stained using Sybr Gold (Thermo-Fisher; USA) and photographed under 300 nm UV illumination. The PAGE results were confirmed by HPLC analysis of the reaction samples.

Results

Figure 35:
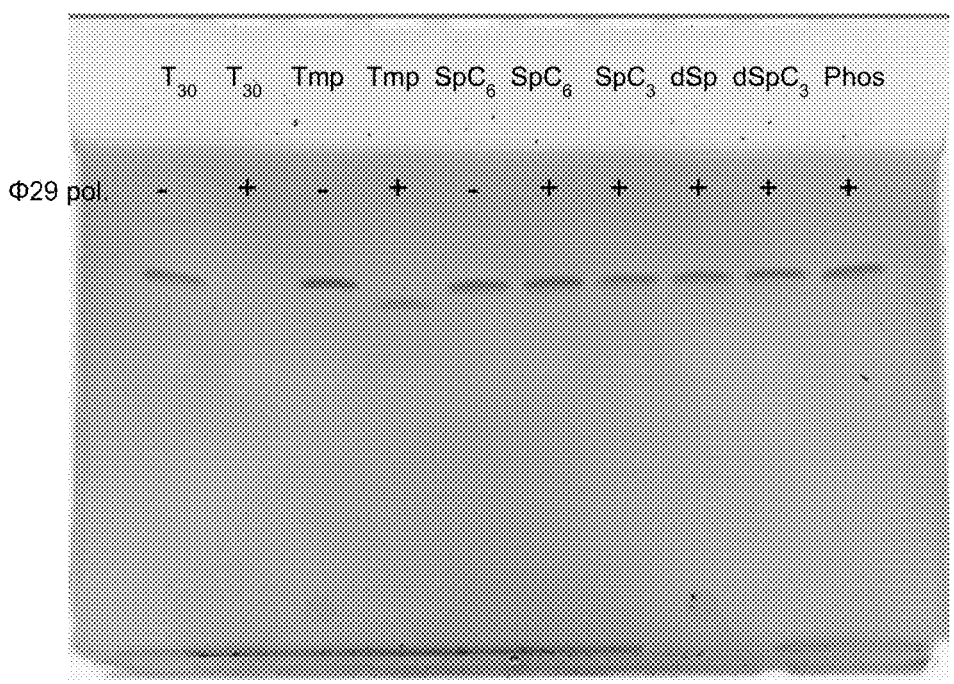
FIG. 35 depicts an SDS-PAGE gel image showing results demonstrating that 3'-chemical modification of oligonucleotide tags can protect the tag from exonuclease degradation by Phi29 polymerase.

As shown in FIG. 35, the T30 oligonucleotide reaction sample having no 3'-modification was completely degraded by the exonuclease activity under these conditions. The T30 oligonucleotide having an un-modified 3'-terminus and internal methyl-phosphonate ("Tmp") linkages also was degraded, but only from the un-modified 3'-terminus to the first Tmp linkage. On the other hand, the oligonucleotides having 3'-modifications with phosphate, or alkyl carbon spacer groups (e.g., SpC3, SpC6, or dSp) remained intact, demonstrating their resistance to the exonuclease activity of the Phi29 DNA polymerase.

Example 15

Oligonucleotide Tags Comprising a CyDye Moieties have Improved Rate of Capture by Polymerase Attached to Nanopores This example illustrates the use of oligonucleotide tagged nucleotides to detect capture of the nucleotide by a polymerase attached to an α-hemolysin nanopore. Moreover, the example illustrates that the inclusion of a cyanine dye ("CyDye") moiety in the linker between the oligonucleotide tag and the nucleotide results in significantly improved rate of capture by the polymerase-nanopore complex.

The protein α-hemolysin self-assembles in the presence of lipid bilayers to form heptameric nanopores. As discussed and referenced elsewhere herein, these nanopores can be modified with a DNA polymerase (with hybridized DNA primer and template) covalently attached adjacent to the pore. The nanopore can be inserted in a lipid bilayer that is immobilized above an electrode containing well fabricated on a CMOS microchip, and the current level changes across the nanopore can be detected upon binding of tagged nucleotides at the polymerase active site.

To perform the experiment described in this example, nanopores were prepared with a single biotin moiety displayed near the C-terminus of each of the seven monomers in the heptameric α-hemolysin pore. Then streptavidin (which has four biotin binding sites) and a biotinylated hairpin BioSingleBell C primer/template DNA (5'-AGA GGA GAT CTC GAG CGC ACT GAC TGC GTG ACC TCA GCT GCA CGT AAG TGC AGC TGA GGT CAC-3') (SEQ ID NO: 115) were added. The presence of streptavidin allowed formation of strong binding complex having one or more hairpin primer/template molecules attached adjacent to the pore. This nanopore complex was purified to remove excess BioSingleBell C DNA primer/template, then DNA polymerase was added and allowed to bind to the primer/template for at least 30 min. at room temperature. The resulting DNA polymerase/nanopore/DNA complex was exposed to lipid bilayers on a Genia chip to form pores. The attached hairpin DNA molecules do not interfere with ionic currents flowing through the pores because their exposed 3' ends are double-stranded and cannot enter the pore.

The two tagged nucleotides used in this example are shown in Table 7 below.

TABLE 7

| Tagged Nucleotide Name | Tag Structure (including alkyne) | SEQ ID NO: |
|---|---|---|
| dG6P-dT$_{30}$-C6 | /5Hexynyl/TTTTT TTTTT TTTTT TTTTT TTTTT TTTTT/3C6/ | 14 |
| dG6P-Cy3-dT$_{30}$-C6 | /5Hexynyl//iCy3/TTTTT TTTTT TTTTT TTTTT TTTTT TTTTT/3C6/ | 15 |

Both tagged nucleotides included were prepared from a 2'-deoxyguanosine hexaphosphate nucleotide ("dG6P") using the alkyne/azide cyclo-addition click chemistry reaction as disclosed elsewhere herein. Briefly, the dG6P was covalently coupled through its terminal phosphate to either 5'-hexynyl-oligo-dT$_{30}$ or 5'-hexynyl-Cy3-oligo-dT$_{30}$. Both tags were modified at the 3'-terminus of the dT$_{30}$ with a hexanol spacer (indicated by the abbreviation "3C6").

A mixture of tagged nucleotide (1 μM), polymerase, primer template, and Sr$^{2+}$ (3 mM) was added to the purified nanopore complex described above and any excess pore was washed away. Under these conditions with Sr$^{2+}$ present, the tagged nucleotide binds to the polymerase active site along with the primer template, and presents its oligonucleotide tag to the pore but does not undergo catalytic polymerization to the primer template chain as it would in the presence of catalytic metal ions. These non-catalytic binding events are readily observed as sudden decreases in ionic current through the pore lasting an average of about 300-600 msec.

Results

When the tagged nucleotide having the oligonucleotide tag with Cy3 in the linker is added to the nanopore array chip, significant current level changes or "current blockade" events that reduced the ionic current from ~12 pA to about 5 pA were detected at a rate of about 46 per minute. Each of the current blockade events indicated that a Cy3-dT$_{30}$-C6 tag was being captured in a nanopore. When the dG6P-dT$_{30}$-C6 tagged nucleotide that lacks the Cy3 moiety in the linker was subsequently added to the same nanopore array chip, the rate of blockade events indicating tag capture was substantially reduced to about 13 per minute. As a control, the dG6P-Cy3-dT$_{30}$-C6 tagged nucleotide subsequently was returned to the nanopore array and the rate of blockage events indicating tag capture increased back to nearly the original level.

A converse experiment also was performed, starting with dG6P-dT$_{30}$-C6 tagged nucleotide that lacked the Cy3 in the linker, then changing to the dG6P-Cy3-dT$_{30}$-C6 tagged nucleotide with Cy3, and finally back to the dG6P-dT$_{30}$-C6.

As would be expected if the Cy3 moiety were increasing the rate of tag capture, the gain, the number, and the rate of nucleotide captures in the nanopore was increased only when dG6P-Cy3-dT$_{30}$-C6 tagged nucleotide was used and decreased significantly when the tagged nucleotide without Cy3 was used.

Table 8 summarizes the results and shows a comparison of the capture rates, dwell times and waiting times from the nanopore capture experiments carried out using these tagged nucleotides with and without the Cy3 present in the linker.

TABLE 8

| Measurement | dG6P-dT$_{30}$-C6 | dG6P-Cy3-dT$_{30}$-C6 |
|---|---|---|
| Mean Captures per Min. | 12.8 | 46 |
| % time captured | 7.3 | 41 |
| Dwell time (msec) | 342 | 535 |
| Waiting time (sec) | 2.1 | 0.4 |
| Total Pores Measured | 118 | 82 |

As noted above, the mean current blockade event rate (as mean captures per minute) increased nearly 4-fold with the Cy3 moiety present as part of the oligonucleotide tag. Similarly, the percentage of time captured also increased—nearly 6-fold. On the other hand, the dwell time, which corresponds to the time the tag spends in the nanopore, increased only modestly ~1.5-fold, which also is favorable because it indicates that the presence of the Cy3 moiety does not cause a significant change in the rate of release of the tag by the nanopore.

Example 16

Identification of Four Different Tagged Nucleotides by Differential Current Blockade Signals at Nanopore-Polymerase Conjugate This example illustrates the use of a nanopore array chip to identify four different tagged nucleotides based on the distinct current blockade signals each provides when bound to a complementary primer-template DNA strand at the active site of Bst2.0 DNA polymerase conjugated to the nanopore. The four different tagged nucleotides used in this examples were: dT6P-Cy3-T$_2$-dSp$_8$-T$_{20}$-C$_3$; dC6P-Cy3-T$_4$-dSp3-T$_{23}$-C$_3$; dG6P-Cy3-T$_{30}$-C$_6$; and dA6P-Cy3-T$_4$-FldT-T-FldT-T$_{23}$-C$_3$. The Bst 2.0-α-HL nanopore conjugate was prepared using the trans-cyclooctene (TCO) to 6-methyltetrazine (6-Me-TZ) reagents and IEDDA click reaction and inserted in a membrane as described in U.S. Provisional Application No. 62/130,326.

Briefly, the Bst2.0 DNA polymerase-nanopore conjugate binds the tagged nucleotides to form a complex in the polymerase active site with the self-priming template. At the same time, under an applied voltage, the "tail" of the tag moiety becomes positioned in the pore of the adjacent α-hemolysin nanopore. The positioning of the tag in the nanopore causes a current decrease (or "current blockade") as compared to the open nanopore current. For example, the dG6P-Cy3-T$_{30}$-C$_6$ tagged nucleotide when captured by the nanopore-conjugated Bst2.0 polymerase was found to produce a consistent current blockade of from about 15 pA open pore current to about 7 pA, with a duration of the current blockade in the millisecond range.

The general method of preparing of the nanopore-polymerase conjugate included the steps of preparing a heptameric complex of α-hemolysin ("α-HL") wherein one of the seven monomer units was the α-HL-C46 mutant. α-HL-C46 has the naturally occurring lysine at position 46 substituted with a cysteine and an N-terminal 6-His tag for purification. The presence of the cysteine in this α-HL-C46 mutant monomer unit allows for the attachment of a single TCO-maleimide linker reagent to the complex. This TCO-group can then conjugate via an IEDDA click reaction with a TZ-group on a modified DNA polymerase. In this example, the single naturally-occurring cysteine residue of DNA polymerase Bst 2.0 was modified with a 6-Me-TZ-maleimide reagent. This 6-Me-TZ-Bst 2.0 adduct was then combined with the TCO-α-HL adduct in a 10:1 ratio to provide a α-HL heptamer conjugate with polymerase Bst 2.0 enzyme. Materials and methods for the modification α-HL-C46 with maleimide linker reagents, and the formation of heptameric α-hemolysin pores incorporating α-HL-C46 also are described in e.g., Valeva et al. (2001), and references cited therein.

Preparation of 6:1 α-HL:α-HL-C46 pore: The K46C (lysine at position 46 substituted with cysteine) mutant of a *Staphyloccocus aureus* α-HL monomer with a 6-His tag ("α-HL-C46") was prepared using standard protein engineering techniques. (see e.g., Valeva et al. (2001) and Palmer et al. (1993)) The α-HL-C46 was purified as described in the protocol for "PrepEase" His-tagged protein purification kits (USB-Affymetrix; USA) and exchanged into 1×PBS with 1 mM tris-carboxyethyl-phosphine (TCEP) at pH 7.2 at 1.0 mg/mL protein concentration. This purified α-HL-C46 was mixed with wild-type α-HL in the presence of lipid to form heptamers as follows.

To obtain the optimal 6:1 ratio of native α-HL monomers to the α-HL-C46 mutant monomer, an 11:1 ratio was used for oligomerization. Lipid (1,2-diphytanoyl-sn-glycero-3-phosphocholine, powder, Avanti Polar Lipids) was added to a final concentration of 5 mg/mL in 50 mM tris, 200 mM NaCl, pH 8.0 for 30 minutes at 40° C. 5% octyl-beta-glucoside (β-OG) was added to pop vesicles, as assessed by clearing, to solubilize the proteins. Then samples were concentrated using 100K MWCO filters and spun at 24000 RPM for 30 minutes to pellet the precipitated protein. After equilibrating size-exclusion columns with 30 mM βOG, 75 mM KCl, 20 mM HEPES at pH 7.5, 500 µL of the concentrated samples were loaded at low pressure to separate heptameric 6:1 α-HL pore complexes from monomers. After concentration to 5 mL in two consecutive size-exclusion columns, the samples were loaded on Mono S 5/50 GL columns (GE Healthcare; New Jersey, USA). Further FPLC was used to separate the 6:1 α-HL:α-HL-C46 pores from those having different subunit stoichiometries (e.g., 7:0, 5:2). The mobile phase consisted of: A, running buffer: 20 mM 2-(N-morpholino)ethanesulfonic acid (MES), 0.1% Tween® 20, at pH 5; B, elution buffer: 2M NaCl, 20 mM MES, 0.1% Tween® 20 at pH 5. Purification was performed from 100% A isocratic over 21 minutes followed by a linear gradient of 0-100% B for 20 minutes and then 100% B isocratic over another 2 minutes. The flow rate was 1 ml/min. Pure native 7:0 α-HL pores eluted first and the 6:1 α-HL:α-HL-C46 pore complexes eluted with a retention time of from about 24.5 min to about 25.5 min.

Preparation of TCO-PEG$_3$-α-HL reagent: A solution of 6:1 α-HL pore complex was exchanged into a phosphate reaction buffer (100 mM sodium phosphate, 150 mM NaCl, pH 7.2) and concentrated using a 100K cut-off desalting spin column to ~300 µg of 6:1 α-HL pore complex in~100 µL volume. A 50 mM TCO-PEG$_3$-maleimide (Jena Bioscience GmbH, Jena, Germany) stock solution was prepared in DMSO. The TCO-PEG$_3$-maleimide stock was added to the 6:1 α-HL pore solution (described above) resulting in a reaction mixture having 100-fold molar excess of the maleimide reagent. This mixture was allowed to react overnight with rotation at 4° C. The resulting TCO-PEG$_3$-α-HL reagent was purified on Sephadex G-50 and used in the IEDDA click reaction with the 6-Me-TZ-PEG$_4$-Bst 2.0 polymerase reagent prepared as described below.

Preparation of 6-Me-TZ-PEG$_4$-Bst 2.0 reagent: DNA polymerase Bst 2.0 (New England Biolabs, Massachusetts, USA) in phosphate reaction buffer (100 mM sodium phosphate, 150 mM NaCl, pH 7.2) was concentrated using a 10K cut-off desalting spin column to ~580 μg in ~100 μL volume. A 50 mM stock solution of 6-Me-TZ-PEG$_4$-maleimide (Jena Bioscience GmbH, Jena, Germany) in DMSO was prepared. The 6-Me-TZ-PEG$_4$-maleimide stock solution was added to the Bst 2.0 solution to yield a reaction mixture having 100-fold excess of the maleimide reagent. Following incubation at 4° C. on a rotator overnight, 1 M DTT was added to a final concentration of 5 mM, and incubation was carried out at room temperature to quench the reaction. The resulting 6-Me-TZ-PEG$_4$-Bst 2.0 reagent was purified on Sephadex G-50 and used in the IEDDA click reaction with the TCO-PEG$_3$-α-HL reagent as described above.

IEDDA click reaction of 6-Me-TZ and TCO conjugates: The IEDDA click reaction between TCO-PEG$_3$-α-HL and 6-Me-TZ-PEG$_4$-Bst 2.0 was carried out using a 5:1 molar excess of 6-Me-TZ-PEG$_4$-Bst 2.0 reagent to the TCO-PEG$_3$-α-HL reagent. Generally, the 6-Me-TZ-PEG$_4$-Bst 2.0 solution was added with mixing to a volume of the TCO-PEG$_3$-α-HL solution to provide the desired 5:1 mole excess in 1×PBS, 5 mM EDTA, at pH 7.0. The mixture was allowed to react at room temperature with rotation for 1 h. Then samples from the reaction mixture was prepared for SDS-PAGE and Bioanalyzer (Agilent) analysis by spin filtering (100K) followed by purification on a Superdex 200 gel-filtration column. Heat denatured samples were prepare by heating at 95° C. for 5 min under. Further purification of the conjugates was carried out using the His-tag on the α-HL-C46 by using a Ni$^{2+}$ column (PrepEase Histidine-tagged Protein Purification Mini Kit High Yield column; Affymetrix, CA, USA). The Ni$^{2+}$ column was run according the manufacturer's protocol. The α-HL nanopore-BST 2.0 conjugate product was stored in 1×PBS buffer at 4° C. prior to further use in preparing nanopore array.

264-well nanopore array microchip: The nanopore current blockade measurements were performed using a ~1×1 mm CMOS microchip that has an array of 264 silver electrodes (5 μm diameter) within shallow wells (chip fabricated by Genia Technologies, Mountain View, Calif., USA). Methods for fabricating and using such nanopore array microchips can also be found in U.S. Patent Application Publication Nos. 2013/0244340 A1 and US 2013/0264207 A1, each of which is hereby incorporated by reference herein. Each well in the array is manufactured using a standard CMOS process with surface modifications that allow for constant contact with biological reagents and conductive salts. Each well can support a phospholipid bilayer membrane with the nanopore conjugate embedded therein, and is individually addressable by computer interface. All reagents used are introduced into a simple flow cell above the chip using a computer-controlled syringe pump. The chip supports analog to digital conversion and reports electrical measurements from all electrodes independently at a rate of over 1000 points per second. Current blockade measurements can be made asynchronously at each of 264 addressable nanopore-containing membranes in the array at least once every millisecond (msec) and recorded on the interfaced computer.

Formation of lipid bilayer on chip: The phospholipid bilayer membrane on the chip was prepared using 1,2-diphytanoyl-sn-glycero-3-phosphocholine (Avanti Polar Lipids). The lipid powder was dissolved in decane at 15 mM and then painted in a layer across the 264 wells on the chip. A thinning process then was initiated by pumping air through the cis side of the wells, thus reducing multi-lamellar lipid membranes to a single bilayer. Bilayer formation was tested using a ramping voltage from 0 to 1000 mV. A typical single bilayer would temporarily open at an applied voltage of between 300 to 500 mV.

Nanopore-conjugate insertion in membrane: After the lipid bilayer formed on the 256 wells of the chip, a solution (150 mM KCl, 3 mM SrCl$_2$, 20 mM Hepes, pH 7.5 at 25° C.) containing 0.05 μg of the Bst2.0-α-HL nanopore conjugate (as described above), 3 μM of the desired "SimpleBell" DNA templates, and 30 μM of one or more of the four tagged nucleotides was added to the cis side of the chip. The Bst2.0-α-HL nanopore conjugate in the mixture spontaneously inserts into the lipid bilayer. Since Sr$^{2+}$ was the only metal ion present in this experiment, the ternary complex at the DNA polymerase was able to form at the active site but the nucleotide was not incorporated and the 5'-phosphate-linked tag was not released.

The SimpleBell DNA template is an 83-mer self-priming single-strand that have the sequence 5'-GCG CTC GAG ATC TCC TCG TAA GAG GAG ATC TCG AGC GCA CTG ACT GXC TGA CCT CAG CTG CAC GTA AGT GCA GCT GAG GTC AG-3' (SEQ ID NO: 116), where X, the first open position on the template, could be any one of the four bases A, C, G or T. The four SimpleBell DNA templates used in these nanopore experiments differed only in the first available position on the template for binding to the complementary nucleotide and incorporation by the polymerase.

The four different tagged nucleotides used in the nanopore experiments were: dT6P-Cy3-T$_2$-dSp$_8$-T20-C$_3$; dC6P-Cy3-T$_4$-dSp$_3$-T$_{23}$-C$_3$; dG6P-Cy3-T$_{30}$-C6; and dA6P-Cy3-T$_4$-FldT-T-FldT-T$_{23}$-C$_3$. (See also, Table 4 above.) Each of the four tagged nucleotides had a Cy3 moiety linked to an oligonucleotide tag made up of varying 30-mer sequences comprising dT nucleotides, fluoro-modified base dT nucleotides (FldT), abasic spacers (dSp), and a 3' exonuclease protective group.

Nanopore current level measurements: The same solution used for inserting nanopore conjugate and DNA template (150 mM KCl, 3 mM SrCl$_2$, 20 mM Hepes, pH 7.5 at 25° C.) was also used as the electrolyte solution for the nanopore current blockade measurements. A 100 mV (cis vs. trans) voltage was applied across the chip-board between two Ag/AgCl electrodes placed on either side of the membrane and pore. Numerous current blockade events were plotted for each of the different tagged nucleotides with the application of voltage across the pore. Plots were recorded based on the two types of current blockade events observed: (1) blockade amplitude, I, as a ratio of the pore current I$_0$, and (2) average dwell time in milliseconds. A histogram of current blockade event dwell times observed for each different tagged nucleotide was fit to the exponential function y=A e$^{-Bx}$ and the reciprocal of constant B used as the calculated average dwell time. Current blockade events with average dwell times longer than 10 ms and a blockade amplitude from 0.6 to 0.2 were deemed to be indicative of productive capture of the tagged nucleotide by the Bst2.0 polymerase conjugated to the nanopore (i.e., binding of the tagged nucleotide with the complementary template base at the polymerase active site and the "tail" of the tagged nucleotide positioned in the adjacent pore).

Experiments were carried out wherein the current blockade levels of each of the four different tagged nucleotides were measured when exposed to an array of its complementary SimpleBell DNA template bound to a membrane embedded nanopore-polymerase conjugate on the array. The results were analyzed for distinct preferred current blockade signatures associated with each different tagged nucleotide.

Additionally, "mismatch" control experiments was carried out wherein only tagged nucleotides that were not complementary to the SimpleBell DNA template were included in the solution exposed to the nanopore array. Specifically, the SimpleBell template used on the array had adenine in the next position on the template and the three mismatch tagged nucleotides applied were: dA6P-Cy3-$T_4$-FldT-T-FldT-$T_{23}$-$C_3$, dG6P-Cy3-$T_{30}$-$C_6$, and dC6P-Cy3-$T_4$-dSp$_3$-$T_{23}$-$C_3$. The conditions used in the mismatch experiment were as described above for detecting the current blockade signatures for the complementary tagged nucleotides.

Results

As shown in Table 9 below, the four different oligonucleotide tagged nucleotides each exhibited distinct blockade amplitudes and average dwell times.

TABLE 9

| Tagged nucleotide | blockade amplitude ($I/I_o$) | avg. dwell time (ms) |
| --- | --- | --- |
| dT6P-Cy3-$T_2$-dSp$_8$-$T_{20}$-$C_3$ | 0.5 to 0.6 | 16.9 |
| dC6P-Cy3-$T_4$-dSp$_3$-$T_{23}$-$C_3$ | 0.4 to 0.5 | 29.7 |
| dG6P-Cy3-$T_{30}$-$C_6$ | 0.3 to 0.4 | 28.6 |
| dA6P-Cy3-$T_4$-FldT-T-FldT-$T_{23}$-$C_3$ | 0.2 to 0.3 | 16.9 |

The current level changes in the nanopore for the mismatch tagged nucleotides, however, were significantly different from the blockade events measured for the complementary tagged nucleotides. The plot of the mismatch current level changes showed very few large changes indicative of a current blockade, and the majority of the mismatch "events" were very close to the open pore current level. Further, the mismatch dwell time histogram for the measured current level changes showed that the majority of events were shorter than 20 msec, which corresponds to the background signal range for complementary tagged nucleotides. Of the 1041 total mismatch "events" detected, only 34.9% events for the mismatch nucleotides were in the usual range for a current blockade and only 19.8% exhibited the typical dwell times for a current blockade. Based on these results, the overall error rates due to tagged nucleotides mismatches was estimated at 6.9%.

Example 17

Sequencing on a Nanopore Array Chip Using Four Different Tagged Nucleotides

This example illustrates the use of four different tagged nucleotides on a nanopore array chip to detect the sequence of DNA template. The four different tagged nucleotides (dT6P-Cy3-$T_2$-dSp$_8$-$T_{20}$-$C_3$; dC6P-Cy3-$T_4$-dSp$_3$-$T_{23}$-$C_3$; dG6P-Cy3-$T_{30}$-$C_6$; and dA6P-Cy3-$T_4$-FldT-T-FldT-$T_{23}$-$C_3$), the nanopore protein (α-hemolysin), DNA template (SimpleBell 83-mer) and the nanopore array chip used (i.e., ~1×1 mm CMOS microchip with a 264 array of 5 μm diameter silver electrodes in shallow wells, fabricated by Genia Technologies, Mountain View, Calif., USA) were the same as used in Example 16. The DNA polymerase used in this example, however, was the Phi29 polymerase and was attached to the α-hemolysin nanopore using the SpyCatcher approach described in Zakeri and Howarth (2010).

Additionally, this sequencing example included the presence of all four different tagged nucleotides and the catalytic metal ion salt $MgCl_2$ to allow for the complete polymerase reaction to occur with incorporation of the complementary tagged nucleotide into the extended primer strand and release of the tag.

Preparation of α-HL-Phi29 conjugates: In this approach, two fragments of the collagen adhesion domain (CnaB2) of the *Streptococcus pyogenes* fibronectin-binding protein FbaB recognize each other and subsequently generate a peptide bond between the c-amino group of a lysine in one fragment (i.e., the "SpyCatcher") and the carboxyl side group of an aspartic acid in the other fragment (i.e., the "SpyTag"). In the present example, the SpyTag fragment was attached via a short peptide linker to the N-terminus of the α-HL monomer, and the SpyCatcher fragment was attached to N-terminus of the Phi29 DNA polymerase via a similar short peptide linker. α-HL monomers with and without the SpyTag were mixed allowing assembly of heptameric nanopores, and those heptameric nanopores with only one SpyTag-modified α-HL monomer were purified by chromatography to provide the desired 6:1 α-HL nanopores. The 6:1 α-HL nanopore solution was then combined with the SpyCatcher-modified Phi29 DNA polymerase to form the 6:1 α-HL-Phi29 conjugates.

Preparation of nanopore array chip: Lipid bilayers were prepared on the 264-well CMOS chip array and the 6:1 α-HL-Phi29 conjugate were inserted in the bilayer together with the DNA template in a buffer solution of 150 mM KCl, 3 mM $SrCl_2$, 20 mM Hepes (pH 7.5 at 25° C.) as described in Example 16. Two different DNA templates were used for the sequencing reactions described in this Example. In the first two reactions (see FIGS. 36A and 36B) the template was the 83-mer self-priming single-stranded SimpleBell DNA template used in Example 16, with an A nucleotide selected at the X position indicating the beginning of the at the start of self-primed region: 5'-GCG CTC GAG ATC TCC TCG TAA GAG GAG ATC TCG AGC GCA CTG ACT GAC TGA CCT CAG CTG CAC GTA AGT GCA GCT GAG GTC AG-3' (SEQ ID NO: 116). In a third sequencing reaction (see FIG. 37), a self-priming single-stranded DNA template with a homopolymeric region was used: 5'-GCA CAC AAG CTT ACC TTT TGG TAA GCT TGT GTC GAA AAT TTT CCC CTA GTA GAA GCA AGT GTT TTC ACT TGC TTC TAC TAG GGG AAA ATT TT-3' (SEQ ID NO: 117).

Sequencing using the nanopore array chip: Following the insertion of the 6:1 α-HL-Phi29 conjugate with self-priming DNA template in the lipid bilayer membrane on the array, the buffer solution on the cis side of the membrane, which contained only $SrCl_2$ metal ion salt, was replaced with a buffer solution that included a buffer solution of 150 mM KCl, 3 mM $MgCl_2$, 3 mM $SrCl_2$, 20 mM HEPES, pH 7.5 at 25° C., and either 0.1 mM $MnCl_2$ (see current trace of FIG. 36A), a mixture of 3.0 mM $MgCl_2$ and 0.7 mM $SrCl_2$ (see current trace of FIG. 36B), or just 3.0 mM $MgCl_2$ (see current trace of FIG. 37). The presence of the catalytic divalent $Mn^{2+}$ or $Mg^{2+}$ ions on the cis side, resulted in the initiation of the catalytic processivity of the Phi29 DNA polymerase. The potential applied across the pore was also varied. A 160 mV potential was applied and maintained in the experiments of FIGS. 36A and 36B, whereas a 100 mV potential was applied, and maintained in the experiment of FIG. 37. The varying amounts of the non-catalytic $Sr^{2+}$ on the cis and/or trans sides of the membrane also affected the polymerase processivity and the resulting ion current level traces (as shown in FIGS. 36A, 36B, and 37). Changes in ion current levels across the nanopores in the array were measured for 3-10 minutes.

Results

Figure 36:
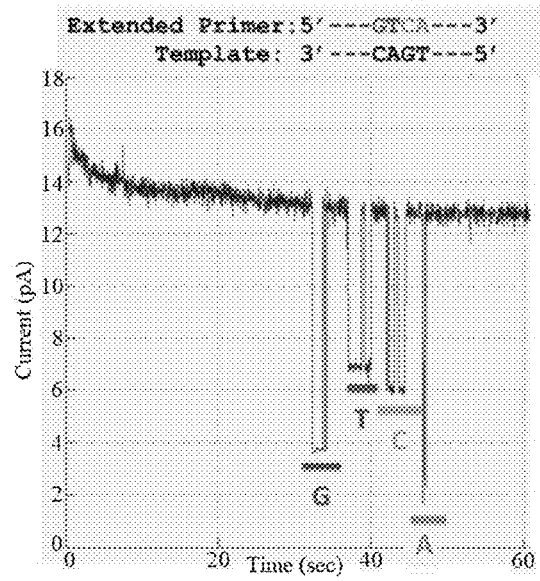
FIG. 36 depicts current level traces corresponding to tag capture events measured under slightly different conditions using a nanopore array chip, a primer (SEQ ID NO: 118) and four different oligonucleotide tagged nucleotides (dT-Tag1 is dT6P-Cy3-dT$_2$-dSp$_8$-dT$_{20}$-C3; dC-Tag2 is dC6P-Cy3-dT$_4$-dSp$_3$-dT$_{23}$-C3; dG-Tag3 is dG6P-Cy3-dT$_{30}$-C6; dA-Tag4 is dA6P-Cy3-dT$_4$-FldT-dT-FldT-dT$_{23}$-C3) to sequence a portion of a DNA template (SEQ ID NO: 120). Conditions used for both (A) and (B) were: 150 mM KCl, 20 mM HEPES, pH 7.5 buffer; 3.0 mM SrCl$_2$ on trans side of pore; 160 mV potential was applied and maintained. The following cis side of the pore conditions differed: (A) 0.1 mM MnCl$_2$ on cis side; (B) 3.0 mM MgCl$_2$+0.7 mM SrCl$_2$ on cis side.
Figure 36:
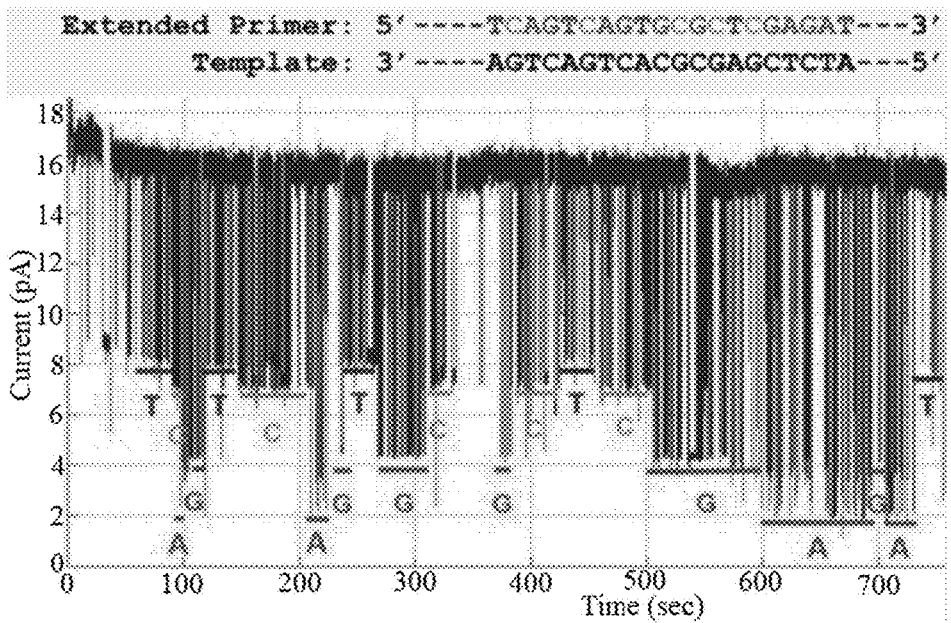
Figure 37:
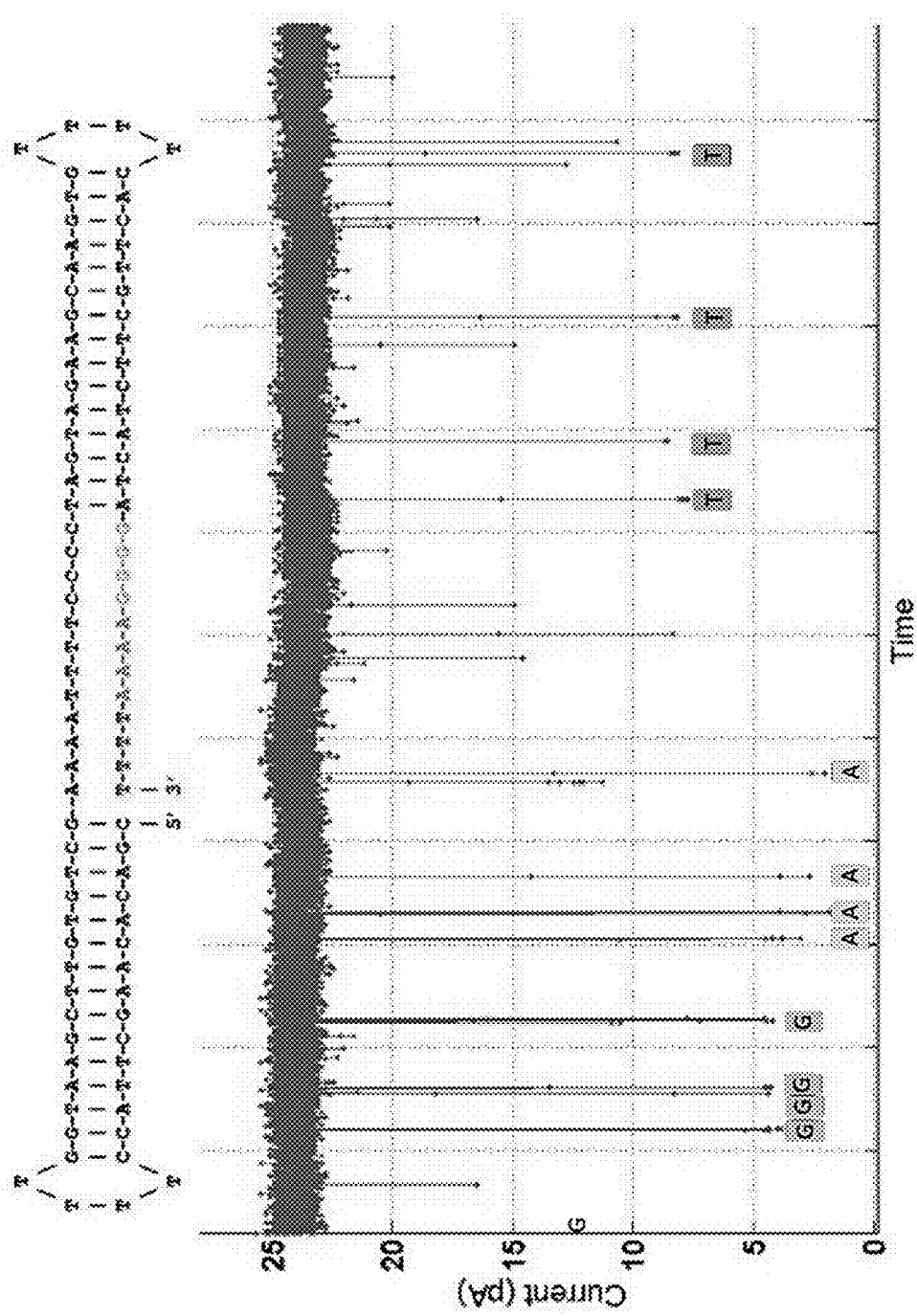
FIG. 37 depicts a current level trace corresponding to tag capture events measured under slightly different conditions using a nanopore array chip and oligonucleotide tagged nucleotides for single molecule, real time, electronic sequencing by synthesis of a 12-base homopolymeric region of a double hairpin template shown above trace. Conditions used were 150 mM KCl, 3.0 mM MgCl$_2$ on cis side of pore, 3.0 mM SrCl$_2$ on trans side of pore, and 100 mV potential was applied and maintained. Tagged nucleotides were as described in FIG. 36.

As shown in FIG. 36, four distinct current levels below the open current level were transiently observed, indicating the capture by the nanopore of four different the tags associated with each of the four different nucleotides. The relative current level changes observed during this sequencing experiment with all four tagged nucleotides present were in agreement with those observed during nanopore array measurements with only a single tag and non-catalytic $Sr^{2+}$ divalent metal ions present (see e.g., Example 16). As expected, the ranking of lowest to highest residual currents ($I/I_0$) observed for the four different tagged nucleotides was consistent with the relative residual currents observed for these tagged nucleotides using the nanopore array chips of Example 16: dA6P-Cy3-$T_4$-FldT-T-FldT-$T_{23}$-$C_3$ (~0.15), <dG6P-Cy3-$T_{30}$-$C_6$ (~0.25), <dC6P-Cy3-$T_4$-$dSp_3$-$T_{23}$-$C_3$ (~0.42), <dT6P-Cy3-$T_2$-$dSp_8$-$T_{20}$-$C_3$ (~0.50). Moreover, the traces of the current level changes indicating tag capture events corresponded to the incorporation of the correct sequence of nucleotides based on the complementary sequence of the self-priming SimpleBell DNA template which is the "Extended Primer" sequence, 5'—TCAGTCA-GTGCGCTCGAGAT—3' (SEQ ID NO: 118), depicted at the top of FIG. 36.

As shown in FIG. 37, a homopolymeric template region, 5'—GGGGAAAATTTT—3' (SEQ ID NO: 119), could be sequenced by detecting the signature current level changes of the tagged nucleotides using a nanopore array chip. Brief reductions in current are indicative of tag capture within the pore, the depth of the deflection characteristic of the different structures of the 4 tags as marked, and very brief (<2 ms) background deflections were ignored. The current trace of FIG. 37 is raw data output with no post processing or noise reduction.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

REFERENCES

Asseline et al. (1991) "Synthesis and physicochemical properties of oligonucleotides built with either alpha-L or beta-L nucleotides units and covalently linked to an acridine derivative" *Nucleic Acids Research* 19:4067-4074.

Sefah et al. (2014) "In vitro selection with artificial expanded genetic information systems" *Proc. Natl. Acad. Sci. USA* 111:1449-1454.

Bhan et al. (1997) "2',5'-Linked oligo-3'-deoxyribonucleoside phosphorothioate chimeras: thermal stability and antisense inhibition of gene expression" *Nucleic Acids Research,* 1997, 25, 3310-3317.

Kim et al. (2005) "A Series of Nonpolar Thymidine Analogues of Increasing Size: DNA Base Pairing and Stacking Properties" *J. Org. Chem.* 70:2048-2053.

Garbesi et al. (1993) "L-DNAs as potential antimessenger oligonucleotides: a reassessment" *Nucleic Acids Research* 21:4159-4165.

Hermanson, "Bioconjugate Techniques", published May 2, 2008, ISBN-13: 978-0123705013.

Himo et al. (2005) "Copper(I)-Catalyzed Synthesis of Azoles. DFT Study Predicts Unprecedented Reactivity and Intermediates," *J. Am. Chem. Soc.,* 127:210-216.

Jewett and Bertozzi (2010) "Cu-free click cycloaddition reactions in chemical biology," *Chem. Soc. Rev.* 39:1272-1279.

Kumar et al. (2012) "PEG-Labeled Nucleotides and Nanopore Detection for Single Molecule DNA Sequencing by Synthesis," *Scientific Reports,* 2:684.

Palmer et al. (1993) "*Staphylococcus aureus* α-Toxin: Production of functionally intact, site-specifically modifiable protein by introduction of cysteine at positions 69, 130, and 186" *J. Biol. Chem.* 268:11959-11962.

Presolski et al. (2011) "Copper-Catalyzed Azide-Alkyne Click Chemistry for Bioconjugation" *Current Protocols in Chemical Biology* 3:153-162.

Reiner et al. (2014) "The inverse electron demand Diels-Alder click reaction in radiochemistry," *J. Label Compd. Radiopharm.* 57:285-290.

Robertson et al. (2007) "Single-molecule mass spectrometry in solution using a single nanopore," *Proc. Natl. Acad. Sci. USA* 104(20):8207-8211.

Romesberg et al. (2014) "Natural-like replication of an unnatural base pair for the expansion of the genetic alphabet and biotechnology applications" *J. Am. Chem. Soc.* 136:826-829.

Romesberg et al. (2014) "Systematic exploration of a class of hydrophobic unnatural base pairs yields multiple new candidates for the expansion of the genetic alphabet" *Nucleic Acids Research* 42:10235-10244.

Valeva et al. (2001) "Membrane insertion of the heptameric staphylococcal alpha-toxin pore—A domino-like structural transition that is allosterically modulated by the target cell membrane", *J. Biol. Chem.* 276(18):14835-14841.

Wang et al. (2003) "Bioconjugation By Copper(I)-Catalyzed Azide-Alkyne [3+2] Cycloaddition," *J. Am. Chem. Soc.* 125 (11):3192-3193.

Zakeri and Howarth (2010) "Spontaneous intermolecular amide bond formation between side chains for irreversible peptide targeting" *J. Am. Chem. Soc* JACS 132(13):4526-27.

U.S. Pat. No. 6,664,079, Ju et al., issued Dec. 16, 2003.
U.S. Pat. No. 8,889,348, Ju et al., issued Nov. 18, 2014.
U.S. Pat. No. 8,324,914, Chen et al., issued Dec. 4, 2012.
U.S. Patent Application Publication No. US 2013/0085271 A1, Wiessler et al., published Apr. 4, 2013.

U.S Patent Application Publication No. US 2013/0244340 A1, Davis et al., published Sep. 19, 2013.

U.S Patent Application Publication No. US 2013/0266512 A1, Fox et al., published Oct. 10, 2013.

U.S. Patent Application Publication No. US 2013/0264207 A1, Ju et al., published Oct. 10, 2013.

U.S. Provisional Application No. 62/130,326, Ju et al., filed Mar. 9, 2015.

PCT International Application Publication No. PCT/US13/35630, Ju et al., filed Apr. 8, 2013.

PCT International Application Publication No. PCT/US13/35635, Ju et al., filed Apr. 8, 2013.

What is claimed is:

1. A tagged nucleotide, comprising a poly-phosphate moiety having a terminal phosphate at the 5' position of the nucleotide, and a tag covalently coupled to the terminal phosphate of the nucleotide by a triazole, a 1,2-diazine, a disulfide, a secondary amine, a hydrazone, a thio-acetamide, or a maleimide-thioadduct,
wherein the tag comprises an oligonucleotide, wherein:
(i) the oligonucleotide comprises a non-naturally occurring internucleotide linkage;
(ii) the 5'-end of the oligonucleotide is covalently coupled to the terminal phosphate and the 3' terminus of the oligonucleotide has a chemical modification which protects it from exonuclease degradation, or the 3'-end of the oligonucleotide is covalently coupled to the terminal phosphate and the 5' terminus of the oligonucleotide has a chemical modification which protects it from exonuclease degradation; or
(iii) the oligonucleotide comprises at least one abasic spacer (dSp).

2. The tagged nucleotide of claim 1, wherein the tag is covalently coupled to the terminal phosphate at the 5' position of the nucleotide by a 1,2-diazine or a triazole having the structure:

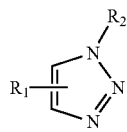

wherein $R_1$ comprises the tag, and $R_2$ comprises the nucleotide; or
wherein $R_1$ comprises the nucleotide, and R2 comprises the tag; or
a triazole having the structure:

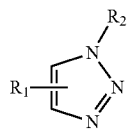

wherein $R_1$ and $R_3$ combine to form a cyclic moiety; and
wherein $R_1$ and $R_3$ combined comprise a tag, and $R_2$ comprises a nucleotide; or
wherein $R_1$ and $R_3$ combined comprise a nucleotide, and $R_2$ comprises a tag.

3. The tagged nucleotide of claim 1, wherein the poly-phosphate moiety comprises at least 3 phosphates, or from 4 to 6 phosphates; wherein the tag further comprises nucleotides, peptides, polyethylene glycol (PEG), or any combination thereof; wherein the oligonucleotide of the tag comprises at least 7 monomer units, or at least 30 monomer units; wherein the 5'-end of the oligonucleotide of the tag is covalently coupled to the terminal phosphate; or wherein the 3'-end of the oligonucleotide of the tag is covalently coupled to the terminal phosphate.

4. The tagged nucleotide of claim 3,
wherein the 5'-end of the oligonucleotide of the tag is covalently coupled to the terminal phosphate and the oligonucleotide comprises a chemical modification of its 3' terminus that protects it from exonuclease degradation; wherein the 5'-end of the oligonucleotide of the tag is covalently coupled to the terminal phosphate and the oligonucleotide comprises a chemical modification of its 3' terminus that protects it from exonuclease degradation, and the chemical modification of its 3' terminus is selected from phosphorylation, and covalent coupling with $C_3$-alkyl to $C_{12}$-alkyl spacers having terminal hydroxyl groups; wherein the 3'-end of the oligonucleotide of the tag is covalently coupled to the terminal phosphate and the oligonucleotide comprises a chemical modification of its 5' terminus that protects it from exonuclease degradation; or wherein the 3'-end of the oligonucleotide of the tag is covalently coupled to the terminal and the oligonucleotide comprises a chemical modification of its 5' terminus that protects it from exonuclease degradation, and the chemical modification of its 5' terminus is selected from phosphorylation, and covalent coupling with $C_3$-alkyl to $C_{12}$-alkyl spacers having terminal hydroxyl groups.

5. The tagged nucleotide of claim 3, wherein the oligonucleotide of the tag comprises a cyanine dye moiety, or a cyanine dye moiety which is a Cy3 moiety; wherein the oligonucleotide of the tag comprises a spacer moiety comprising an alkyl group of at least 2 carbons to about 12 carbons; wherein the oligonucleotide of the tag comprises a spacer comprising an abasic unit; wherein the oligonucleotide of the tag comprises a spacer selected from the group consisting of idSp, iSp9, iSp18, iSpC3, iSpC6, and iSpC12; or wherein the oligonucleotide of the tag comprises a spacer selected from the group consisting of pyrolidine, spermine, nitropyrrole, nitroindole, nebularine, benimidazole, benzene, 7-deazapurines, 5-substituted pyrimidine, fluorescein-dT, fluorescein, rhodamine, and ROX.

6. The tagged nucleotide of claim 1, wherein the tag further comprises oligo-saccharides, carbohydrates, peptide nucleic acids (PNA), vinyl polymers, other water-soluble polymers or any combination thereof; wherein the oligonucleotide of the tag comprises an unnatural nucleotide; wherein the oligonucleotide of the tag comprises an unnatural nucleotide comprising a group selected from the group consisting of an L-nucleotide, a 2', 5'-linkage, an α-D-nucleotide, a non-naturally occurring internucleotide linkage, a non-naturally-occurring base, a non-naturally occurring sugar moiety, and any combination thereof; wherein the oligonucleotide of the tag comprises an unnatural nucleotide comprising a non-naturally occurring base selected from the group consisting of nitropyrrole, nitroindole, nebularine, zebularine, benzene, and benzene derivatives; or wherein the oligonucleotide of the tag comprises an unnatural nucleotide comprising a non-naturally occurring internucleotide linkage selected from the group consisting of a phosphotriester, phosphorothioate, methylphosphonate, boronophosphate, phosphoramidate, and a morpholino moiety.

7. The tagged nucleotide of claim 1, wherein the tag is represented by SEQ ID NOS. 109-114, or the tag is represented by SEQ ID NOS. 17, 18, 22-33, 42-72, 74-82, 86-88, 90, or 94-102; wherein the tag is represented by SEQ ID NOS. 6, 8-16, 19-21, or 34-41; wherein the tag is represented by SEQ ID NOS. 89, 91-93, or 103-105; wherein the tag is represented by SEQ ID NOS. 73, 83-85, or 106; wherein the tagged nucleotide is selected from the group consisting of dG6P-(T$_4$-Npy2)$_6$-C3, dG6P-(T$_4$-Neb2) $_6$-C3, dT6P-dT$_6$-C7-NH$_6$-dT$_{18}$-C3, dT6P-dT$_6$ -Pyrd$_6$-dT$_{18}$-C3, dA6P-dT$_6$-dTNH$_6$-dT$_{18}$-C3, dG6P-dT$_4$-sperm-dT$_{22}$-C3, dT6P-dT$_4$-sperm-dSp$_3$-dT$_{19}$-C3, dC6P-dT$_4$-sperm-iFlrT-dT$_{21}$-C3, dG6P-sperm-dT$_{30}$-C3, dT6P-Cy3.5-dT$_{30}$-C3, dT6P-Cy3-Cy3-dT$_{30}$-C3, dT6P -dT$_6$-Cy3-dT$_{23}$-C3, dT6P-dT$_{10}$-Cy3-dT$_{19}$-C3, dT6P -Hairpin Block, dA6P-Cy3-T2-Sp18-T$_{22}$-C3, dT6P-Cy3-dT4-dSp$_8$-T$_{18}$-C3, dT6P-Hex-dT$_6$-dTC2NH$_6$-dT$_{18}$-C3, dA6P-Cy3-dT$_4$-Sp9-T$_{23}$-C3, dC6P-Cy3-T-dSp$_3$-T$_{26}$_C3, dC6P-Cy3-T$_4$-dSp$_3$-T$_{23}$_C3, dC6P-Cy3-T$_7$-dSp$_3$-T$_{20}$_C3, dC6P-Cy3-T$_{10}$-dSp$_3$-T$_{17}$_C3, dC6P-Cy3-T$_4$-iFluorT$_3$-T23-C3, dC6P-Cy3 T$_4$-iFluorT-T-iFluorT-T$_{23}$-C3, Bio-Spermine-dT$_{30}$-C3, dT6P-dT$_{30}$-Cy3-C3, dG6P-dT$_8$-Spermine-dT$_{20}$-C3, dA6P-Cy3-T$_4$-iFluorT-T-iFluorT-T$_{23}$-C3, dT6P-CY3-dT4-Aptamer-dT25-C3, dT6P-Cy3-dT4-12Hairpin-dT25-C3, dT6P-Cy3-dT$_5$-dSp$_3$-dT$_{22}$-C3, dT6P-Cy3-dT$_6$-dSp$_3$-dT$_{21}$-C3, dT6P-Cy3-dT$_4$-dSp$_4$-dT$_{22}$-C3, dT6P-Cy3-dT$_4$-dSp$_5$-dT$_{21}$-C3, dC6P-Cy3-dT$_5$-SpC12-dT$_{23}$-C3, dC6P-Cy3-dT$_4$-SpC6-SpC6-dT$_{24}$-C$_3$, dC6P-Cy3-dT$_4$-(SpC3)$_3$-dT$_{23}$-C3, dG6P-Cy3-dT$_{30}$-C3, dT6P-Cy3-dT$_2$-dSp$_8$-dT$_{20}$-C3, dC6P-Cy3-T$_{30}$-(C$_3$)$_4$-PO$_4$, dC6P-Cy3-T$_{30}$-PO$_4$, dC6P-Cy3-T$_{30}$-C$_3$-NH$_2$, dG6PαS-Cy3-dT$_2$-dSp$_8$-dT$_{20}$-C3, Rev-P-T$_{30}$-Cy3-dG6P, Rev-P-T$_{24}$-dSp$_3$-T$_3$-Cy3-dC6P, dT6P-Cy3-dT$_4$-HP6-dT$_{25}$-C$_3$, dA6P-Cy3-dT4-dI6-dT20-C3, dA6P-Cy3-dT4-Nitrindole6-dT20-C3, dA6P-Cy3-dT4-dC6-dT20-C3, dA6P-Cy3-dT4-5IU6-dT20-C3, dA6P-Cy3-dT4-PyrndU6-dT20-C3, dT6P-Cy3-dT$_4$-(idSP-T)$_4$-dT$_{18}$-C3, dT6P-Cy3-dT$_5$-(idSP-T)$_4$-dT$_{17}$-C3, dT6P-Cy3-dT$_4$-Propyl$_6$-dT$_{20}$-C3, dT6P-Cy3-LdT$_{30}$-C3, dT6P-Cy3-dT$_4$-L111-dT$_{26}$-C3, dT6P-Cy3-dT$_4$-L121-dT$_{26}$-C3, dT6P-Cy3-dT$_4$-SpC12-SpC12-dT$_{24}$-C3, dT6P-Cy3-dT$_4$-(SpC6) $_4$-dT$_{25}$-C3, dT6P-Cy3-dT$_4$-Spermine-dT$_{25}$-C3, dT6P-Cy3-dT2-Spermine-dT$_{27}$-C3, dT6P-Cy3-dT2-Spermine-Spermine-dT$_{26}$-C3, dT6P-Cy3-dT$_4$-Pyrn-dU-TT-Pyrn-dU-dT$_{22}$-C3, dT6P-Cy3-dT$_4$-Tmp$_6$-dT$_{20}$-C3, dT6P-Cy3-dT$_4$-Pyrrolidine$_6$-dT$_{20}$-C3, dT6P-Pyrrolidine-dT$_{30}$-C3, dT6P-Pyrrolidine-Pyrrolidine-dT$_{30}$-C3, and dT6P-Pyrrolidine$_3$-dT$_{30}$-C3; wherein the tagged nucleotide is selected from the group consisting of dA6P-T*$_{30}$_ODD, dT6P-T$_6$-dSp$_8$-T$_{16}$, dC6P-T$_6$-T*$_{10}$-T$_{14}$, dC6P-T$_4$-dSp$_3$-T$_{23}$, dC6P-T$_7$-dSp$_3$-T$_{20}$, dC6P-T$_{10}$-dSp$_3$-T$_{17}$, dC6P-T$_{13}$-dSp$_3$-T$_{14}$, dG6P-T$_{30}$-C6, dG6P-Cy3-T$_{30}$-C6, dT6P-T$_4$-dSp$_{10}$-T$_{16}$-C6, dA6P-T$_4$-Sp18-T$_{22}$-C3, dA6P-T$_4$-Sp18$_2$-T$_{19}$_ C$_3$, dA6P-T$_4$-Sp9$_2$-T$_{22}$_C3, dT6P-T$_6$-dSp$_8$-T$_{16}$-C3, dA6P-Cy3-T$_{30}$-C6, dT6P-Cy3-T$_{30}$-C6, dC6P-Cy3-T$_{30}$-C6, dA6P-Cy3-dT*$_{30}$_ODD, dA6P-T*$_{30}$, dA6P-Cy3-T*$_{30}$, dG6P-Cy3-T$_{30}$-C3, dG6P-Cy3-T$_{15}$-C3, dG6P-Cy3-T$_{20}$-C3, and dG6P-Cy3-T$_{25}$-C3; wherein the tagged nucleotide is selected from the group consisting of dT6P-Cy3-dT$_3$-(SpC12)$_3$-dT$_{24}$-C3, dT6P-Cy3-dT$_4$-(SpC6)$_5$-dT$_{23}$-C3, dT6P-Cy3-dT5-(SpC6)$_4$-dT$_{24}$-C3, dT6P-Cy3-dT$_2$-(SpC6)$_5$-dT$_{25}$-C3, dT6P-SpC3-Cy3-dT$_{30}$-C3, dT6P-SpC3-SpC3-Cy3-dT$_{30}$-C3, and dT6P-SpC6-Cy3-dT$_{30}$-C3; wherein the tagged nucleotide is selected from the group consisting of dT6P-Cy3-dC$_{30}$-C3, dT6P-Cy3-LdT$_4$-dSp$_3$-LdT$_{23}$-C3, dT6P-Cy3-LdT$_4$-dSp$_8$-LdT$_{18}$-c3, dT6P-Cy3-LdT$_4$-dI$_6$-LdT$_{20}$-C3, and dT6P-Cy3-dT$_4$(alpha-dT)$_3$-dT$_{23}$-C3; wherein the tag comprises a chemical modification selected from the group consisting of the chemical modifications listed in Table 6; or wherein the tagged nucleotide comprises a linker comprising a cyanine dye moiety, or a cyanine dye moiety which is a Cy3 moiety has an improved rate of capture by a polymerase.

8. The tagged nucleotide of claim 1, wherein the tag is covalently coupled to the terminal phosphate at the 5' position of the nucleotide by a 1,2-diazine or a triazole having the structure:

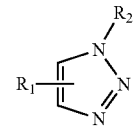

wherein R$_1$ comprises the tag, and R$_2$ comprises the nucleotide; or wherein R$_1$ comprises the nucleotide, and R$_2$ comprises the tag.

9. The tagged nucleotide of claim 8, wherein:
(i) the poly-phosphate moiety comprises 6 phosphates; and
(ii) the 5'-end of the oligonucleotide of the tag is covalently coupled to the terminal phosphate of a poly-phosphate moiety.

10. The tagged nucleotide of claim 9, wherein the oligonucleotide of the tag comprises an unnatural nucleotide comprising a group selected from the groups consisting of an L-nucleotide, a 2',5'-linkage, an α-D-nucleotide, a non-naturally occurring internucleotide linkage, a non-naturally occurring base, a non-naturally occurring sugar moiety, an abasic unit, a chemical modification selected from the group consisting of the chemical modifications listed in table 6, and any combination thereof.

11. The tagged nucleotide of claim 9, wherein the oligonucleotide of the tag comprises at least 30 monomer units.

12. The tagged nucleotide of claim 9, wherein the oligonucleotide of the tag comprises an unnatural nucleotide comprising a group selected from the groups consisting of a non-naturally occurring base, a non-naturally occurring sugar moiety, an abasic unit, a chemical modification selected from the group consisting of the chemical modifications listed in table 6, and any combination thereof.

13. The tagged nucleotide of claim 12, wherein the oligonucleotide of the tag comprises an unnatural nucleotide comprising a non-naturally occurring internucleotide linkage.

14. The tagged nucleotide of claim 13 wherein the non-naturally occurring internucleotide linkage is a phosphotriester or thiophosphate diester.

15. The tagged nucleotide of claim 14 wherein the tag is represented by SEQ ID NOS. 6, 9, and 36, or wherein the tagged nucleotide is selected from the group consisting of dA6P-T*$_{30}$—ODD, dC6P-T$_6$-T*$_{10}$-T$_{14}$, and dA6P-T*$_{30}$.

16. The tagged nucleotide of claim 13, wherein the oligonucleotide of the tag comprises an unnatural nucleotide comprising a spacer moiety comprising an alkyl group of at least 2 carbons to about 12 carbons.

17. The tagged nucleotide of claim 16, wherein the oligonucleotide of the tag comprises a chemical modification at its 3'-terminus that protects it from exonuclease degradation.

18. The tagged nucleotide of claim 17, wherein the chemical modification is selected from the group consisting of phosphorylation and covalent coupling with C3-alkyl to C12-alkyl spacers having terminal hydroxyl groups.

19. The tagged nucleotide of claim 18, wherein the tag is represented by SEQ ID NOS. 16, 19-21, 24, or 34, or wherein the tagged nucleotide is selected from the group consisting of dT6P-T$_4$-dSp$_{10}$-T$_{16}$-C6, dA6P-T$_4$-Sp18-T$_{22}$-C3, dA6P-T$_4$-Sp18$_2$-T$_{19}$-C$_3$, dA6P-T$_4$-Sp9$_2$-T$_{22}$-C3, dA6P-dT$_6$-dTNH$_6$-dT$_{18}$.-C3, and dT6P-T$_6$-dSp$_B$-T$_{16}$-C3.

20. A kit for sequencing nucleic acid comprising a tagged nucleotide of claim 1.

* * * * *

SEQUENCE LISTING

```
<160> NUMBER OF SEQ ID NOS: 122

<210> SEQ ID NO 1
<211> LENGTH: 30
<212> TYPE: DNA
<213> ORGANISM: Artificial Sequence
<220> FEATURE:
<223> OTHER INFORMATION: Synthesized sequence
<220> FEATURE:
<221> NAME/KEY: misc_feature
<222> LOCATION: (1)..(1)
<223> OTHER INFORMATION: T-biotin-streptavidin
<220> FEATURE:
<221> NAME/KEY: misc_feature
<222> LOCATION: (11)..(13)
<223> OTHER INFORMATION: abasic site
<220> FEATURE:
<221> NAME/KEY: misc_feature
<222> LOCATION: (17)..(19)
<223> OTHER INFORMATION: abasic site

<400> SEQUENCE: 1
tttttttttt nnntttnnnt tttttttttt                30

<210> SEQ ID NO 2
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: T-biotin-streptavidin
<220> FEATURE:
<221> NAME/KEY: misc_feature
<222> LOCATION: (17)..(19)
<223> OTHER INFORMATION: abasic site

<400> SEQUENCE: 2
tttttttttt ttttttnnnt tttttttttt                30

<210> SEQ ID NO 3
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: T-biotin-streptavidin

<400> SEQUENCE: 3
tttttttttt tttttttttt tttttttttt                30

<210> SEQ ID NO 4
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
```

```
<222> LOCATION: (1)..(1)
<223> OTHER INFORMATION: T-biotin-streptavidin
<220> FEATURE:
<221> NAME/KEY: misc_feature
<222> LOCATION: (18)..(18)
<223> OTHER INFORMATION: T-fluorescein

<400> SEQUENCE: 4
tttttttttt tttttttttt tttttttttt                                              30

<210> SEQ ID NO 5
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5'-hexyne-phosphate-cyanine 3-phosphate-T

<400> SEQUENCE: 5
tttttttttt tttttttttt tttttttttt                                              30

<210> SEQ ID NO 6
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5'-hexyne-phosphate-T
<220> FEATURE:
<221> NAME/KEY: misc_feature
<222> LOCATION: (1)..(1)
<223> OTHER INFORMATION: thiophosphate diester bond to following T
<220> FEATURE:
<221> NAME/KEY: misc_feature
<222> LOCATION: (3)..(3)
<223> OTHER INFORMATION: thiophosphate diester bond to following T
<220> FEATURE:
<221> NAME/KEY: misc_feature
<222> LOCATION: (5)..(5)
<223> OTHER INFORMATION: thiophosphate diester bond to following T
<220> FEATURE:
<221> NAME/KEY: misc_feature
<222> LOCATION: (7)..(7)
<223> OTHER INFORMATION: thiophosphate diester bond to following T
<220> FEATURE:
<221> NAME/KEY: misc_feature
<222> LOCATION: (9)..(9)
<223> OTHER INFORMATION: thiophosphate diester bond to following T
<220> FEATURE:
<221> NAME/KEY: misc_feature
<222> LOCATION: (11)..(11)
<223> OTHER INFORMATION: thiophosphate diester bond to following T
<220> FEATURE:
<221> NAME/KEY: misc_feature
<222> LOCATION: (13)..(13)
<223> OTHER INFORMATION: thiophosphate diester bond to following T
<220> FEATURE:
<221> NAME/KEY: misc_feature
<222> LOCATION: (15)..(15)
<223> OTHER INFORMATION: thiophosphate diester bond to following T
<220> FEATURE:
<221> NAME/KEY: misc_feature
<222> LOCATION: (17)..(17)
<223> OTHER INFORMATION: thiophosphate diester bond to following T
<220> FEATURE:
<221> NAME/KEY: misc_feature
<222> LOCATION: (19)..(19)
<223> OTHER INFORMATION: thiophosphate diester bond to following T
<220> FEATURE:
```

```
<221> NAME/KEY: misc_feature
<222> LOCATION: (21)..(21)
<223> OTHER INFORMATION: thiophosphate diester bond to following T
<220> FEATURE:
<221> NAME/KEY: misc_feature
<222> LOCATION: (23)..(23)
<223> OTHER INFORMATION: thiophosphate diester bond to following T
<220> FEATURE:
<221> NAME/KEY: misc_feature
<222> LOCATION: (25)..(25)
<223> OTHER INFORMATION: thiophosphate diester bond to following T
<220> FEATURE:
<221> NAME/KEY: misc_feature
<222> LOCATION: (27)..(27)
<223> OTHER INFORMATION: thiophosphate diester bond to following T
<220> FEATURE:
<221> NAME/KEY: misc_feature
<222> LOCATION: (29)..(29)
<223> OTHER INFORMATION: thiophosphate diester bond to following T

<400> SEQUENCE: 6
tttttttttt tttttttttt tttttttttt                                    30

<210> SEQ ID NO 7
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-hexyne-phosphate-T

<400> SEQUENCE: 7
tttttttttt tttttttttt tttttttttt                                    30

<210> SEQ ID NO 8
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (7)..(14)
<223> OTHER INFORMATION: furan amidite

<400> SEQUENCE: 8 tttttttnnnn nnnntttttt tttttttttt                                   30

<210> SEQ ID NO 9
<211> LENGTH: 30
<212> TYPE: DNA
<213> ORGANISM: Artificial sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (7)..(16)
<223> OTHER INFORMATION: thiophosphate diester bond to following T

<400> SEQUENCE: 9
tttttttttt tttttttttt tttttttttt                                    30
```

<210> SEQ ID NO 10
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (4)..(6)
<223> OTHER INFORMATION: furan amidite

<400> SEQUENCE: 10
tttnnntttt tttttttttt tttttttttt                                    30

<210> SEQ ID NO 11
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (8)..(10)
<223> OTHER INFORMATION: furan amidite

<400> SEQUENCE: 11
tttttttnnn tttttttttt tttttttttt                                    30

<210> SEQ ID NO 12
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (11)..(13)
<223> OTHER INFORMATION: furan amidite

<400> SEQUENCE: 12
tttttttttt nnnttttttt tttttttttt                                    30

<210> SEQ ID NO 13
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (14)..(16)
<223> OTHER INFORMATION: furan amidite

<400> SEQUENCE: 13
tttttttttt tttnnnttttt tttttttttt                             30

<210> SEQ ID NO 14
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (30)..(30)
<223> OTHER INFORMATION: hexanol-T

<400> SEQUENCE: 14
tttttttttt tttttttttt tttttttttt                             30

<210> SEQ ID NO 15
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (30)..(30)
<223> OTHER INFORMATION: hexanol

<400> SEQUENCE: 15
tttttttttt tttttttttt tttttttttt                             30

<210> SEQ ID NO 16
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (5)..(14)
<223> OTHER INFORMATION: furan amidite
<220> FEATURE:
<221> NAME/KEY: misc_feature
<222> LOCATION: (30)..(30)
<223> OTHER INFORMATION: hexanol-T

<400> SEQUENCE: 16
ttttnnnnnn nnnnttttt tttttttttt                              30

<210> SEQ ID NO 17
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature

```
<222> LOCATION: (5)..(6)
<223> OTHER INFORMATION: nitropyrrole
<220> FEATURE:
<221> NAME/KEY: misc_feature
<222> LOCATION: (11)..(12)
<223> OTHER INFORMATION: nitropyrrole
<220> FEATURE:
<221> NAME/KEY: misc_feature
<222> LOCATION: (17)..(18)
<223> OTHER INFORMATION: nitropyrrole
<220> FEATURE:
<221> NAME/KEY: misc_feature
<222> LOCATION: (23)..(24)
<223> OTHER INFORMATION: nitropyrrole
<220> FEATURE:
<221> NAME/KEY: misc_feature
<222> LOCATION: (29)..(29)
<223> OTHER INFORMATION: nitropyrrole
<220> FEATURE:
<221> NAME/KEY: misc_feature
<222> LOCATION: (30)..(30)
<223> OTHER INFORMATION: nitropyrrole-propanol

<400> SEQUENCE: 17
ttttnntttt nntttttnntt ttnnttttnn                                         30

<210> SEQ ID NO 18
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (5)..(6)
<223> OTHER INFORMATION: nebularine
<220> FEATURE:
<221> NAME/KEY: misc_feature
<222> LOCATION: (11)..(12)
<223> OTHER INFORMATION: nebularine
<220> FEATURE:
<221> NAME/KEY: misc_feature
<222> LOCATION: (17)..(18)
<223> OTHER INFORMATION: nebularine
<220> FEATURE:
<221> NAME/KEY: misc_feature
<222> LOCATION: (23)..(24)
<223> OTHER INFORMATION: nebularine
<220> FEATURE:
<221> NAME/KEY: misc_feature
<222> LOCATION: (29)..(29)
<223> OTHER INFORMATION: nebularine
<220> FEATURE:
<221> NAME/KEY: misc_feature
<222> LOCATION: (30)..(30)
<223> OTHER INFORMATION: nebularine-propanol

<400> SEQUENCE: 18
ttttnntttt nntttttnntt ttnnttttnn                                         30

<210> SEQ ID NO 19
<211> LENGTH: 27
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
```

-continued

```
<221> NAME/KEY: misc_feature
<222> LOCATION: (5)..(5)
<223> OTHER INFORMATION: 18-atom PEG
<220> FEATURE:
<221> NAME/KEY: misc_feature
<222> LOCATION: (27)..(27)
<223> OTHER INFORMATION: T-propanol

<400> SEQUENCE: 19
ttttnttttt tttttttttt ttttttt                                          27

<210> SEQ ID NO 20
<211> LENGTH: 25
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (5)..(6)
<223> OTHER INFORMATION: 18-atom PEG-phosphate
<220> FEATURE:
<221> NAME/KEY: misc_feature
<222> LOCATION: (25)..(25)
<223> OTHER INFORMATION: T-propanol
<220> FEATURE:
<221> NAME/KEY: misc_feature
<222> LOCATION: (28)..(28)
<223> OTHER INFORMATION: propanol-T

<400> SEQUENCE: 20
ttttnntttt tttttttttt ttttt                                            25

<210> SEQ ID NO 21
<211> LENGTH: 28
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (5)..(6)
<223> OTHER INFORMATION: 9-atom PEG-phosphate
<220> FEATURE:
<221> NAME/KEY: misc_feature
<222> LOCATION: (28)..(28)
<223> OTHER INFORMATION: T-propanol

<400> SEQUENCE: 21
ttttnntttt tttttttttt tttttttt                                         28

<210> SEQ ID NO 22
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (7)..(12)
<223> OTHER INFORMATION: heptylamine amidite
```

```
<220> FEATURE:
<221> NAME/KEY: misc_feature
<222> LOCATION: (30)..(30)
<223> OTHER INFORMATION: T-propanol

<400> SEQUENCE: 22
tttttthnnn nntttttttt tttttttttt                                      30

<210> SEQ ID NO 23
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (7)..(12)
<223> OTHER INFORMATION: pyrrolidine amidite
<220> FEATURE:
<221> NAME/KEY: misc_feature
<222> LOCATION: (30)..(30)
<223> OTHER INFORMATION: T-propanol

<400> SEQUENCE: 23
tttttthnnn nntttttttt tttttttttt                                      30

<210> SEQ ID NO 24
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (7)..(12)
<223> OTHER INFORMATION: aminoethyl dT amidite
<220> FEATURE:
<221> NAME/KEY: misc_feature
<222> LOCATION: (30)..(30)
<223> OTHER INFORMATION: T-propanol

<400> SEQUENCE: 24
tttttthnnn nntttttttt tttttttttt                                      30

<210> SEQ ID NO 25
<211> LENGTH: 27
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (5)..(5)
<223> OTHER INFORMATION: spermine
<220> FEATURE:
<221> NAME/KEY: misc_feature
<222> LOCATION: (27)..(27)
<223> OTHER INFORMATION: T-propanol

<400> SEQUENCE: 25
```
ttttnttttt tttttttttt ttttttt                                              27

<210> SEQ ID NO 26
<211> LENGTH: 27
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (5)..(5)
<223> OTHER INFORMATION: spermine
<220> FEATURE:
<221> NAME/KEY: misc_feature
<222> LOCATION: (6)..(8)
<223> OTHER INFORMATION: furan amidite
<220> FEATURE:
<221> NAME/KEY: misc_feature
<222> LOCATION: (27)..(27)
<223> OTHER INFORMATION: T-propanol

<400> SEQUENCE: 26
ttttnnnntt tttttttttt ttttttt                                              27

<210> SEQ ID NO 27
<211> LENGTH: 27
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (5)..(5)
<223> OTHER INFORMATION: spermine
<220> FEATURE:
<221> NAME/KEY: misc_feature
<222> LOCATION: (6)..(6)
<223> OTHER INFORMATION: fluorescein dT amidite
<220> FEATURE:
<221> NAME/KEY: misc_feature
<222> LOCATION: (27)..(27)
<223> OTHER INFORMATION: T-propanol

<400> SEQUENCE: 27
ttttnntttt tttttttttt ttttttt                                              27

<210> SEQ ID NO 28
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (30)..(30)
<223> OTHER INFORMATION: T-propanol

<400> SEQUENCE: 28
tttttttttt tttttttttt tttttttttt                                           30

```
<210> SEQ ID NO 29
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3.5-T
<220> FEATURE:
<221> NAME/KEY: misc_feature
<222> LOCATION: (30)..(30)
<223> OTHER INFORMATION: T-propanol

<400> SEQUENCE: 29
tttttttttt tttttttttt tttttttttt                                30

<210> SEQ ID NO 30
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-cyanine-3-
      phosphate-T
<220> FEATURE:
<221> NAME/KEY: misc_feature
<222> LOCATION: (30)..(30)
<223> OTHER INFORMATION: T-propanol

<400> SEQUENCE: 30
tttttttttt tttttttttt tttttttttt                                30

<210> SEQ ID NO 31
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (7)..(7)
<223> OTHER INFORMATION: cyanine 3.5-phosphate
<220> FEATURE:
<221> NAME/KEY: misc_feature
<222> LOCATION: (30)..(30)
<223> OTHER INFORMATION: T-propanol

<400> SEQUENCE: 31
ttttttnttt tttttttttt tttttttttt                                30

<210> SEQ ID NO 32
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (11)..(11)
<223> OTHER INFORMATION: cyanine 3-phosphate
```

<220> FEATURE:
<221> NAME/KEY: misc_feature
<222> LOCATION: (30)..(30)
<223> OTHER INFORMATION: T-propanol

<400> SEQUENCE: 32
tttttttttt nttttttttt tttttttttt                                     30

<210> SEQ ID NO 33
<211> LENGTH: 45
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (45)..(45)
<223> OTHER INFORMATION: T-propanol

<400> SEQUENCE: 33
ttttcggcgc gtaagcgccg tttttttttt tttttttttt ttttt                     45

<210> SEQ ID NO 34
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (7)..(14)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 34 tttttnnnn nnnnttttt tttttttttt                                       30

<210> SEQ ID NO 35
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (1)..(1)
<223> OTHER INFORMATION: thiophosphate diester bond to following T
<220> FEATURE:
<221> NAME/KEY: misc_feature
<222> LOCATION: (3)..(3)
<223> OTHER INFORMATION: thiophosphate diester bond to following T
<220> FEATURE:
<221> NAME/KEY: misc_feature
<222> LOCATION: (5)..(5)
<223> OTHER INFORMATION: thiophosphate diester bond to following T
<220> FEATURE:
<221> NAME/KEY: misc_feature
<222> LOCATION: (7)..(7)

```
<223> OTHER INFORMATION: thiophosphate diester bond to following T
<220> FEATURE:
<221> NAME/KEY: misc_feature
<222> LOCATION: (9)..(9)
<223> OTHER INFORMATION: thiophosphate diester bond to following T
<220> FEATURE:
<221> NAME/KEY: misc_feature
<222> LOCATION: (11)..(11)
<223> OTHER INFORMATION: thiophosphate diester bond to following T
<220> FEATURE:
<221> NAME/KEY: misc_feature
<222> LOCATION: (13)..(13)
<223> OTHER INFORMATION: thiophosphate diester bond to following T
<220> FEATURE:
<221> NAME/KEY: misc_feature
<222> LOCATION: (15)..(15)
<223> OTHER INFORMATION: thiophosphate diester bond to following T
<220> FEATURE:
<221> NAME/KEY: misc_feature
<222> LOCATION: (17)..(17)
<223> OTHER INFORMATION: thiophosphate diester bond to following T
<220> FEATURE:
<221> NAME/KEY: misc_feature
<222> LOCATION: (19)..(19)
<223> OTHER INFORMATION: thiophosphate diester bond to following T
<220> FEATURE:
<221> NAME/KEY: misc_feature
<222> LOCATION: (21)..(21)
<223> OTHER INFORMATION: thiophosphate diester bond to following T
<220> FEATURE:
<221> NAME/KEY: misc_feature
<222> LOCATION: (23)..(23)
<223> OTHER INFORMATION: thiophosphate diester bond to following T
<220> FEATURE:
<221> NAME/KEY: misc_feature
<222> LOCATION: (25)..(25)
<223> OTHER INFORMATION: thiophosphate diester bond to following T
<220> FEATURE:
<221> NAME/KEY: misc_feature
<222> LOCATION: (27)..(27)
<223> OTHER INFORMATION: thiophosphate diester bond to following T
<220> FEATURE:
<221> NAME/KEY: misc_feature
<222> LOCATION: (29)..(29)
<223> OTHER INFORMATION: thiophosphate diester bond to following T
<220> FEATURE:
<221> NAME/KEY: misc_feature
<222> LOCATION: (30)..(30)
<223> OTHER INFORMATION: T-propanol

<400> SEQUENCE: 35
tttttttttt tttttttttt tttttttttt                                    30

<210> SEQ ID NO 36
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (1)..(29)
<223> OTHER INFORMATION: thiophosphate diester bond to following T

<400> SEQUENCE: 36
tttttttttt tttttttttt tttttttttt                                    30

<210> SEQ ID NO 37
<211> LENGTH: 30
<212> TYPE: DNA
<213> ORGANISM: Artificial Sequence
```

```
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (1)..(29)
<223> OTHER INFORMATION: thiophosphate diester bond to next T

<400> SEQUENCE: 37
tttttttttt tttttttttt tttttttttt                                    30

<210> SEQ ID NO 38
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (30)..(30)
<223> OTHER INFORMATION: T-propanol

<400> SEQUENCE: 38
tttttttttt tttttttttt tttttttttt                                    30

<210> SEQ ID NO 39
<211> LENGTH: 15
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (15)..(15)
<223> OTHER INFORMATION: T-propanol

<400> SEQUENCE: 39
tttttttttt ttttt                                                    15

<210> SEQ ID NO 40
<211> LENGTH: 20
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (20)..(20)
<223> OTHER INFORMATION: T-propanol

<400> SEQUENCE: 40
tttttttttt tttttttttt                                               20

<210> SEQ ID NO 41
<211> LENGTH: 25
<212> TYPE: DNA
```

```
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (25)..(25)
<223> OTHER INFORMATION: T-propanol

<400> SEQUENCE: 41
tttttttttt tttttttttt ttttt                                   25

<210> SEQ ID NO 42
<211> LENGTH: 25
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3- phosphate-T
<220> FEATURE:
<221> NAME/KEY: misc_feature
<222> LOCATION: (3)..(3)
<223> OTHER INFORMATION: 18-atom PEG-phosphate
<220> FEATURE:
<221> NAME/KEY: misc_feature
<222> LOCATION: (25)..(25)
<223> OTHER INFORMATION: T-propanol

<400> SEQUENCE: 42 ttntttttttt tttttttttt ttttt                                  25

<210> SEQ ID NO 43
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(12)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 43
ttttnnnnnn nntttttttt tttttttttt                              30

<210> SEQ ID NO 44
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (7)..(12)
<223> OTHER INFORMATION: aminoethyl dT amidite
```

```
<220> FEATURE:
<221> NAME/KEY: misc_feature
<222> LOCATION: (30)..(30)
<223> OTHER INFORMATION: T-propanol

<400> SEQUENCE: 44 tttttnnnn nnttttttttt tttttttttt                                    30

<210> SEQ ID NO 45
<211> LENGTH: 28
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(5)
<223> OTHER INFORMATION: 9 atom PEG-phosphate
<220> FEATURE:
<221> NAME/KEY: misc_feature
<222> LOCATION: (25)..(25)
<223> OTHER INFORMATION: T-propanol

<400> SEQUENCE: 45
ttttnttttt tttttttttt ttttttttt                                     28

<210> SEQ ID NO 46
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (2)..(4)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 46
tnnntttttt tttttttttt tttttttttt                                    30

<210> SEQ ID NO 47
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(7)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 47
```
ttttnnnttt tttttttttt tttttttttt                                           30

<210> SEQ ID NO 48
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (8)..(10)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 48
tttttttnnn tttttttttt tttttttttt                                           30

<210> SEQ ID NO 49
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (11)..(13)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 49
tttttttttt nnntttttttt tttttttttt                                          30

<210> SEQ ID NO 50
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(7)
<223> OTHER INFORMATION: fluorescein dT amidite
<220> FEATURE:
<221> NAME/KEY: misc_feature
<222> LOCATION: (30)..(30)
<223> OTHER INFORMATION: T-propanol

<400> SEQUENCE: 50
ttttnnnttt tttttttttt tttttttttt                                           30

<210> SEQ ID NO 51
<211> LENGTH: 30
<212> TYPE: DNA
<213> ORGANISM: Artificial Sequence

```
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(5)
<223> OTHER INFORMATION: fluorescein-dT-amidite
<220> FEATURE:
<221> NAME/KEY: misc_feature
<222> LOCATION: (7)..(7)
<223> OTHER INFORMATION: fluorescein-dT-amidite
<220> FEATURE:
<221> NAME/KEY: misc_feature
<222> LOCATION: (30)..(30)
<223> OTHER INFORMATION: T-propanol

<400> SEQUENCE: 51
ttttntnttt tttttttttt tttttttttt                                30

<210> SEQ ID NO 52
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-spermine-phosphate-T
<220> FEATURE:
<221> NAME/KEY: misc_feature
<222> LOCATION: (30)..(30)
<223> OTHER INFORMATION: T-propanol

<400> SEQUENCE: 52
tttttttttt tttttttttt tttttttttt                                30

<210> SEQ ID NO 53
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (30)..(30)
<223> OTHER INFORMATION: T-cyanine 3-phosphate-propanol

<400> SEQUENCE: 53
tttttttttt tttttttttt tttttttttt                                30

<210> SEQ ID NO 54
<211> LENGTH: 29
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-T
<220> FEATURE:
<221> NAME/KEY: misc_feature
<222> LOCATION: (9)..(9)
<223> OTHER INFORMATION: spermine
<220> FEATURE:
```

```
<221> NAME/KEY: misc_feature
<222> LOCATION: (29)..(29)
<223> OTHER INFORMATION: T-propanol

<400> SEQUENCE: 54
ttttttttnt tttttttttt ttttttttt                                    29

<210> SEQ ID NO 55
<211> LENGTH: 44
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (44)..(44)
<223> OTHER INFORMATION: T-propanol

<400> SEQUENCE: 55
ttttggttgg tgtggttggt tttttttttt tttttttttt tttt                   44

<210> SEQ ID NO 56
<211> LENGTH: 57
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (57)..(57)
<223> OTHER INFORMATION: T-propanol

<400> SEQUENCE: 56
ttttccggcg cggcgcgtaa gcgccgcgcc ggtttttttt tttttttttt ttttttt     57

<210> SEQ ID NO 57
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (6)..(8)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 57
tttttnnntt tttttttttt tttttttttt                                   30

<210> SEQ ID NO 58
<211> LENGTH: 30
<212> TYPE: DNA
<213> ORGANISM: Artificial Sequence
<220> FEATURE:
<223> OTHER INFORMATION: synthesized oligonucleotide
```

```
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (7)..(9)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 58 tttttttnnnt tttttttttt tttttttttt                                30

<210> SEQ ID NO 59
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(8)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 59
ttttnnnntt tttttttttt tttttttttt                                 30

<210> SEQ ID NO 60
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(9)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 60
ttttnnnnnt tttttttttt tttttttttt                                 30

<210> SEQ ID NO 61
<211> LENGTH: 29
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (6)..(6)
```

<223> OTHER INFORMATION: dodecyl amidite-phosphate
<220> FEATURE:
<221> NAME/KEY: misc_feature
<222> LOCATION: (29)..(29)
<223> OTHER INFORMATION: T-propanol
<220> FEATURE:
<221> NAME/KEY: misc_feature
<222> LOCATION: (30)..(30)
<223> OTHER INFORMATION: T-propanol

<400> SEQUENCE: 61
tttttntttt tttttttttt tttttttttt                                      29

<210> SEQ ID NO 62
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(6)
<223> OTHER INFORMATION: hexyl amidite
<220> FEATURE:
<221> NAME/KEY: misc_feature
<222> LOCATION: (30)..(30)
<223> OTHER INFORMATION: T-propanol

<400> SEQUENCE: 62
ttttnntttt tttttttttt tttttttttt                                      30

<210> SEQ ID NO 63
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(7)
<223> OTHER INFORMATION: propyl amidite
<220> FEATURE:
<221> NAME/KEY: misc_feature
<222> LOCATION: (30)..(30)
<223> OTHER INFORMATION: T-propanol

<400> SEQUENCE: 63
ttttnnnttt tttttttttt tttttttttt                                      30

<210> SEQ ID NO 64
<211> LENGTH: 30
<212> TYPE: DNA
<213> ORGANISM: Artificial sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (30)..(30)
<223> OTHER INFORMATION: T-propanol

<400> SEQUENCE: 64
tttttttttt tttttttttt tttttttttt                                    30

<210> SEQ ID NO 65
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (3)..(10)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 65
ttnnnnnnnn tttttttttt tttttttttt                                    30

<210> SEQ ID NO 66
<211> LENGTH: 34
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (31)..(33)
<223> OTHER INFORMATION: propyl amidite
<220> FEATURE:
<221> NAME/KEY: misc_feature
<222> LOCATION: (34)..(34)
<223> OTHER INFORMATION: propyl amidite-propanol

<400> SEQUENCE: 66
tttttttttt tttttttttt tttttttttt nnnn                               34

<210> SEQ ID NO 67
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (30)..(30)
<223> OTHER INFORMATION: T-phosphate

<400> SEQUENCE: 67
tttttttttt tttttttttt tttttttttt                                    30

<210> SEQ ID NO 68
<211> LENGTH: 30
<212> TYPE: DNA
<213> ORGANISM: Artificial Sequence
<220> FEATURE:
<223> OTHER INFORMATION: synthesized oligonucleotide
<220> FEATURE:

<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (30)..(30)
<223> OTHER INFORMATION: T-propylamine

<400> SEQUENCE: 68
tttttttttt tttttttttt tttttttttt                                    30

<210> SEQ ID NO 69
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (3)..(10)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 69
ttnnnnnnnn tttttttttt tttttttttt                                    30

<210> SEQ ID NO 70
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: phosphate-T
<220> FEATURE:
<221> NAME/KEY: misc_feature
<222> LOCATION: (30)..(30)
<223> OTHER INFORMATION: T-cyanine 3-phosphate-propylamine-phosphate-
      proparyl-propionamide

<400> SEQUENCE: 70
tttttttttt tttttttttt tttttttttt                                    30

<210> SEQ ID NO 71
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: phosphate-T
<220> FEATURE:
<221> NAME/KEY: misc_feature
<222> LOCATION: (25)..(27)
<223> OTHER INFORMATION: furan amidite
<220> FEATURE:
<221> NAME/KEY: misc_feature
<222> LOCATION: (30)..(30)
<223> OTHER INFORMATION: T-cyanine 3-phosphate-propylamine-phosphate-
      proparyl-propionamide

<400> SEQUENCE: 71 ttttttttt tttttttttt ttttnnnttt          30

<210> SEQ ID NO 72
<211> LENGTH: 45
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (45)..(45)
<223> OTHER INFORMATION: T-propanol

<400> SEQUENCE: 72
ttttcggcgc gtaagcgccg tttttttttt tttttttttt ttttt          45

<210> SEQ ID NO 73
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-C
<220> FEATURE:
<221> NAME/KEY: misc_feature
<222> LOCATION: (30)..(30)
<223> OTHER INFORMATION: C-propanol

<400> SEQUENCE: 73
cccccccccc cccccccccc cccccccccc          30

<210> SEQ ID NO 74
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(10)
<223> OTHER INFORMATION: 2'-deoxyinosine
<220> FEATURE:
<221> NAME/KEY: misc_feature
<222> LOCATION: (30)..(30)
<223> OTHER INFORMATION: T-propanol

<400> SEQUENCE: 74
ttttnnnnnn tttttttttt tttttttttt          30

<210> SEQ ID NO 75
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:

```
<221> NAME/KEY: misc_feature
<222> LOCATION: (5)..(10)
<223> OTHER INFORMATION: 5-nitroindole
<220> FEATURE:
<221> NAME/KEY: misc_feature
<222> LOCATION: (30)..(30)
<223> OTHER INFORMATION: T-propanol

<400> SEQUENCE: 75
ttttnnnnnn tttttttttt tttttttttt                                      30

<210> SEQ ID NO 76
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (30)..(30)
<223> OTHER INFORMATION: T-propanol

<400> SEQUENCE: 76
tttcccccct tttttttttt tttttttttt                                      30

<210> SEQ ID NO 77
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(10)
<223> OTHER INFORMATION: 5-iodo deoxyuridine
<220> FEATURE:
<221> NAME/KEY: misc_feature
<222> LOCATION: (30)..(30)
<223> OTHER INFORMATION: T-propanol

<400> SEQUENCE: 77
ttttnnnnnn tttttttttt tttttttttt                                      30

<210> SEQ ID NO 78
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(10)
<223> OTHER INFORMATION: 5-pyrene-deoxyuridine
<220> FEATURE:
<221> NAME/KEY: misc_feature
<222> LOCATION: (30)..(30)
<223> OTHER INFORMATION: T-propanol

<400> SEQUENCE: 78
ttttnnnnnn tttttttttt tttttttttt                                      30
```

```
<210> SEQ ID NO 79
<211> LENGTH: 29
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (3)..(30)
<223> OTHER INFORMATION: T-propanol
<220> FEATURE:
<221> NAME/KEY: misc_feature
<222> LOCATION: (5)..(5)
<223> OTHER INFORMATION: furan amidite
<220> FEATURE:
<221> NAME/KEY: misc_feature
<222> LOCATION: (7)..(7)
<223> OTHER INFORMATION: furan amidite
<220> FEATURE:
<221> NAME/KEY: misc_feature
<222> LOCATION: (9)..(9)
<223> OTHER INFORMATION: furan amidite
<220> FEATURE:
<221> NAME/KEY: misc_feature
<222> LOCATION: (11)..(11)
<223> OTHER INFORMATION: furan amidite

<400> SEQUENCE: 79
ttttntntnt nttttttttt ttttttttt                                29

<210> SEQ ID NO 80
<211> LENGTH: 29
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (6)..(6)
<223> OTHER INFORMATION: furan amidite
<220> FEATURE:
<221> NAME/KEY: misc_feature
<222> LOCATION: (8)..(8)
<223> OTHER INFORMATION: furan amidite
<220> FEATURE:
<221> NAME/KEY: misc_feature
<222> LOCATION: (10)..(10)
<223> OTHER INFORMATION: furan amidite
<220> FEATURE:
<221> NAME/KEY: misc_feature
<222> LOCATION: (12)..(12)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 80
tttttntntn tnttttttttt ttttttttt                               29

<210> SEQ ID NO 81
<211> LENGTH: 30
<212> TYPE: DNA
<213> ORGANISM: Artificial Sequence
<220> FEATURE:
```

```
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(10)
<223> OTHER INFORMATION: propanol
<220> FEATURE:
<221> NAME/KEY: misc_feature
<222> LOCATION: (30)..(30)
<223> OTHER INFORMATION: T-propanol

<400> SEQUENCE: 81
ttttnnnnnn tttttttttt tttttttttt                                  30

<210> SEQ ID NO 82
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-L isomer
      of T
<220> FEATURE:
<221> NAME/KEY: misc_feature
<222> LOCATION: (2)..(29)
<223> OTHER INFORMATION: L isomer of T
<220> FEATURE:
<221> NAME/KEY: misc_feature
<222> LOCATION: (30)..(30)
<223> OTHER INFORMATION: L isomer of T-propanol

<400> SEQUENCE: 82
tttttttttt tttttttttt tttttttttt                                  30

<210> SEQ ID NO 83
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-L isomer
      of T
<220> FEATURE:
<221> NAME/KEY: misc_feature
<222> LOCATION: (2)..(4)
<223> OTHER INFORMATION: L isomer of T
<220> FEATURE:
<221> NAME/KEY: misc_feature
<222> LOCATION: (5)..(7)
<223> OTHER INFORMATION: furan amidite
<220> FEATURE:
<221> NAME/KEY: misc_feature
<222> LOCATION: (8)..(29)
<223> OTHER INFORMATION: L isomer of T
<220> FEATURE:
<221> NAME/KEY: misc_feature
<222> LOCATION: (30)..(30)
<223> OTHER INFORMATION: L isomer of T-propanol

<400> SEQUENCE: 83
ttttnnnttt tttttttttt tttttttttt                                  30

<210> SEQ ID NO 84
<211> LENGTH: 30
```

```
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-L isomer
      of T
<220> FEATURE:
<221> NAME/KEY: misc_feature
<222> LOCATION: (2)..(4)
<223> OTHER INFORMATION: L isomer of T
<220> FEATURE:
<221> NAME/KEY: misc_feature
<222> LOCATION: (5)..(12)
<223> OTHER INFORMATION: furan amidite
<220> FEATURE:
<221> NAME/KEY: misc_feature
<222> LOCATION: (13)..(29)
<223> OTHER INFORMATION: L isomer of T
<220> FEATURE:
<221> NAME/KEY: misc_feature
<222> LOCATION: (30)..(30)
<223> OTHER INFORMATION: L isomer of T-propanol

<400> SEQUENCE: 84
ttttnnnnnn nntttttttt tttttttttt                              30

<210> SEQ ID NO 85
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-L isomer
      of T
<220> FEATURE:
<221> NAME/KEY: misc_feature
<222> LOCATION: (2)..(4)
<223> OTHER INFORMATION: L isomer of T
<220> FEATURE:
<221> NAME/KEY: misc_feature
<222> LOCATION: (5)..(10)
<223> OTHER INFORMATION: 2'-deoxy I
<220> FEATURE:
<221> NAME/KEY: misc_feature
<222> LOCATION: (11)..(29)
<223> OTHER INFORMATION: L isomer of T
<220> FEATURE:
<221> NAME/KEY: misc_feature
<222> LOCATION: (30)..(30)
<223> OTHER INFORMATION: L isomer of T-propanol

<400> SEQUENCE: 85
ttttnnnnnn tttttttttt tttttttttt                              30

<210> SEQ ID NO 86
<211> LENGTH: 45
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (45)..(54)
<223> OTHER INFORMATION: T-propanol
```

```
<400> SEQUENCE: 86
ttttgggtgg gtgggtgggt tttttttttt tttttttttt ttttt                45

<210> SEQ ID NO 87
<211> LENGTH: 46
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (46)..(46)
<223> OTHER INFORMATION: T-propanol

<400> SEQUENCE: 87
ttttgggtgg gttgggtggg tttttttttt tttttttttt tttttt               46

<210> SEQ ID NO 88
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(6)
<223> OTHER INFORMATION: dodecyl amidite
<220> FEATURE:
<221> NAME/KEY: misc_feature
<222> LOCATION: (30)..(30)
<223> OTHER INFORMATION: T-propanol

<400> SEQUENCE: 88
ttttnntttt tttttttttt tttttttttt                                 30

<210> SEQ ID NO 89
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (4)..(6)
<223> OTHER INFORMATION: dodecyl amidite
<220> FEATURE:
<221> NAME/KEY: misc_feature
<222> LOCATION: (30)..(30)
<223> OTHER INFORMATION: T-propanol

<400> SEQUENCE: 89
tttnnntttt tttttttttt tttttttttt                                 30

<210> SEQ ID NO 90
<211> LENGTH: 33
<212> TYPE: DNA
<213> ORGANISM: Artificial Sequence
<220> FEATURE:
<223> OTHER INFORMATION: synthesized oligonucleotide
```

```
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(8)
<223> OTHER INFORMATION: hexyl amidite
<220> FEATURE:
<221> NAME/KEY: misc_feature
<222> LOCATION: (33)..(33)
<223> OTHER INFORMATION: T-propanol

<400> SEQUENCE: 90
ttttnnnntt tttttttttt tttttttttt ttt                           33

<210> SEQ ID NO 91
<211> LENGTH: 32
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(9)
<223> OTHER INFORMATION: hexyl amidite
<220> FEATURE:
<221> NAME/KEY: misc_feature
<222> LOCATION: (32)..(32)
<223> OTHER INFORMATION: T-propanol

<400> SEQUENCE: 91
ttttnnnnnt tttttttttt tttttttttt tt                            32

<210> SEQ ID NO 92
<211> LENGTH: 33
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (6)..(9)
<223> OTHER INFORMATION: hexyl amidite
<220> FEATURE:
<221> NAME/KEY: misc_feature
<222> LOCATION: (33)..(33)
<223> OTHER INFORMATION: T-propanol

<400> SEQUENCE: 92
tttttnnnnt tttttttttt tttttttttt ttt                           33

<210> SEQ ID NO 93
<211> LENGTH: 32
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (3)..(7)
```

<223> OTHER INFORMATION: hexyl amidite
<220> FEATURE:
<221> NAME/KEY: misc_feature
<222> LOCATION: (32)..(32)
<223> OTHER INFORMATION: T-propanol

<400> SEQUENCE: 93
ttnnnnnttt tttttttttt tttttttttt tt                                32

<210> SEQ ID NO 94
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(5)
<223> OTHER INFORMATION: spermine
<220> FEATURE:
<221> NAME/KEY: misc_feature
<222> LOCATION: (30)..(30)
<223> OTHER INFORMATION: T-propanol

<400> SEQUENCE: 94
ttttnttttt tttttttttt tttttttttt                                   30

<210> SEQ ID NO 95
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (3)..(3)
<223> OTHER INFORMATION: spermine
<220> FEATURE:
<221> NAME/KEY: misc_feature
<222> LOCATION: (30)..(30)
<223> OTHER INFORMATION: T-propanol

<400> SEQUENCE: 95 ttntttttttt tttttttttt tttttttttt                                  30

<210> SEQ ID NO 96
<211> LENGTH: 30
<212> TYPE: DNA
<213> ORGANISM: Artificial sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (3)..(4)
<223> OTHER INFORMATION: spermine
<220> FEATURE:
<221> NAME/KEY: misc_feature
<222> LOCATION: (30)..(30)
<223> OTHER INFORMATION: T-propanol

<400> SEQUENCE: 96 ttnnttttt tttttttttt tttttttttt         30

<210> SEQ ID NO 97
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(5)
<223> OTHER INFORMATION: 5-pyrene-deoxyuridine
<220> FEATURE:
<221> NAME/KEY: misc_feature
<222> LOCATION: (7)..(7)
<223> OTHER INFORMATION: 5-pyrene-deoxyuridine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (30)..(30)
<223> OTHER INFORMATION: T-propanol

<400> SEQUENCE: 97
ttttnttntt tttttttttt tttttttttt         30

<210> SEQ ID NO 98
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(10)
<223> OTHER INFORMATION: thymidine methylphosphonate
<220> FEATURE:
<221> NAME/KEY: misc_feature
<222> LOCATION: (30)..(30)
<223> OTHER INFORMATION: T-propyl

<400> SEQUENCE: 98
ttttnnnnnn tttttttttt tttttttttt         30

<210> SEQ ID NO 99
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(10)
<223> OTHER INFORMATION: pyrrolidine
<220> FEATURE:
<221> NAME/KEY: misc_feature
<222> LOCATION: (30)..(30)
<223> OTHER INFORMATION: T-propanol

```
<400> SEQUENCE: 99
ttttnnnnnt tttttttttt tttttttttt                                    30

<210> SEQ ID NO 100
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-pyrrolidine-phosphate-T
<220> FEATURE:
<221> NAME/KEY: misc_feature
<222> LOCATION: (30)..(30)
<223> OTHER INFORMATION: T-propanol

<400> SEQUENCE: 100
tttttttttt tttttttttt tttttttttt                                    30

<210> SEQ ID NO 101
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-pyrrolidine-phosphate-
      pyrrolidine-phosphate-T
<220> FEATURE:
<221> NAME/KEY: misc_feature
<222> LOCATION: (30)..(30)
<223> OTHER INFORMATION: T-propanol

<400> SEQUENCE: 101
tttttttttt tttttttttt tttttttttt                                    30

<210> SEQ ID NO 102
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-pyrrolidine-phosphate-
      pyrrolidine-phosphate-pyrrolidine-phosphate-T
<220> FEATURE:
<221> NAME/KEY: misc_feature
<222> LOCATION: (30)..(30)
<223> OTHER INFORMATION: T-propanol

<400> SEQUENCE: 102
tttttttttt tttttttttt tttttttttt                                    30

<210> SEQ ID NO 103
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-propyl amidite-cyanine 3-
      phosphate-T
<220> FEATURE:
```

```
<221> NAME/KEY: misc_feature
<222> LOCATION: (30)..(30)
<223> OTHER INFORMATION: T-propanol

<400> SEQUENCE: 103
tttttttttt tttttttttt tttttttttt                                              30

<210> SEQ ID NO 104
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-propyl amidite-propyl amidite-
      cyanine 3-phosphate-T
<220> FEATURE:
<221> NAME/KEY: misc_feature
<222> LOCATION: (30)..(30)
<223> OTHER INFORMATION: T-propanol

<400> SEQUENCE: 104
tttttttttt tttttttttt tttttttttt                                              30

<210> SEQ ID NO 105
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-hexyl amidite-cyanine 3-
      phosphate-T
<220> FEATURE:
<221> NAME/KEY: misc_feature
<222> LOCATION: (30)..(30)
<223> OTHER INFORMATION: T-propanol

<400> SEQUENCE: 105
tttttttttt tttttttttt tttttttttt                                              30

<210> SEQ ID NO 106
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: hexyne-phosphate-cyanine 3-phosphate-T
<220> FEATURE:
<221> NAME/KEY: misc_feature
<222> LOCATION: (5)..(7)
<223> OTHER INFORMATION: alpha anomer of T
<220> FEATURE:
<221> NAME/KEY: misc_feature
<222> LOCATION: (30)..(30)
<223> OTHER INFORMATION: T-propanol

<400> SEQUENCE: 106
tttttttttt tttttttttt tttttttttt                                              30

<210> SEQ ID NO 107
<211> LENGTH: 83
<212> TYPE: DNA
<213> ORGANISM: Artificial Sequence
```

<220> FEATURE:
<223> OTHER INFORMATION: synthesized oligonucleotide

<400> SEQUENCE: 107
gcgctcgaga tctcctcgta agaggagatc tcgagcgcac tgactgactg acctcagctg    60
cacgtaagtg cagctgaggt cag    83

<210> SEQ ID NO 108
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: biotin-T

<400> SEQUENCE: 108
tttttttttt tttttttttt tttttttttt    30

<210> SEQ ID NO 109
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: biotin-T
<220> FEATURE:
<221> NAME/KEY: misc_feature
<222> LOCATION: (30)..(30)
<223> OTHER INFORMATION: T-furan amidite-furan amidite-furan amidite

<400> SEQUENCE: 109
tttttttttt tttttttttt tttttttttt    30

<210> SEQ ID NO 110
<211> LENGTH: 33
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: biotin-T
<220> FEATURE:
<221> NAME/KEY: misc_feature
<222> LOCATION: (31)..(33)
<223> OTHER INFORMATION: any nt
<220> FEATURE:
<221> NAME/KEY: misc_feature
<222> LOCATION: (31)..(33)
<223> OTHER INFORMATION: any

<400> SEQUENCE: 110
tttttttttt tttttttttt tttttttttt nnn    33

<210> SEQ ID NO 111
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)

```
<223> OTHER INFORMATION: biotin-T
<220> FEATURE:
<221> NAME/KEY: misc_feature
<222> LOCATION: (30)..(30)
<223> OTHER INFORMATION: t-propanol

<400> SEQUENCE: 111
tttttttttt tttttttttt tttttttttt                                             30

<210> SEQ ID NO 112
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: biotin-T
<220> FEATURE:
<221> NAME/KEY: misc_feature
<222> LOCATION: (30)..(30)
<223> OTHER INFORMATION: T-hexanol

<400> SEQUENCE: 112
tttttttttt tttttttttt tttttttttt                                             30

<210> SEQ ID NO 113
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: biotin-T
<220> FEATURE:
<221> NAME/KEY: misc_feature
<222> LOCATION: (30)..(30)
<223> OTHER INFORMATION: T-furan amidite-propanol

<400> SEQUENCE: 113
tttttttttt tttttttttt tttttttttt                                             30

<210> SEQ ID NO 114
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: biotin-T
<220> FEATURE:
<221> NAME/KEY: misc_feature
<222> LOCATION: (10)..(12)
<223> OTHER INFORMATION: thymidine methyl phosphonate
<220> FEATURE:
<221> NAME/KEY: misc_feature
<222> LOCATION: (16)..(18)
<223> OTHER INFORMATION: thymidine methyl phosphonate

<400> SEQUENCE: 114 ttttttttn nnttnnntt tttttttttt                                             30

<210> SEQ ID NO 115
<211> LENGTH: 63
<212> TYPE: DNA
<213> ORGANISM: Artificial Sequence
```

```
<220> FEATURE:
<223> OTHER INFORMATION: synthesized oligonucleotide

<400> SEQUENCE: 115
agaggagatc tcgagcgcac tgactgcgtg acctcagctg cacgtaagtg cagctgaggt      60
cac                                                                    63

<210> SEQ ID NO 116
<211> LENGTH: 83
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (47)..(47)
<223> OTHER INFORMATION: any nt

<400> SEQUENCE: 116
gcgctcgaga tctcctcgta agaggagatc tcgagcgcac tgactgnctg acctcagctg      60
cacgtaagtg cagctgaggt cag                                              83

<210> SEQ ID NO 117
<211> LENGTH: 92
<212> TYPE: DNA
<213> ORGANISM: Artificial Sequence
<220> FEATURE:
<223> OTHER INFORMATION: synthesized oligonucleotide

<400> SEQUENCE: 117
gcacacaagc ttaccttttg gtaagcttgt gtcgaaaatt ttccctagt agaagcaagt       60 gttttcactt gcttctacta ggggaaaatt tt                                    92

<210> SEQ ID NO 118
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 118
tcagtcagtg cgctcgagat                                                  20

<210> SEQ ID NO 119
<211> LENGTH: 12
<212> TYPE: DNA
<213> ORGANISM: Artificial Sequence
<220> FEATURE:
<223> OTHER INFORMATION: synthesized oligonucleotide

<400> SEQUENCE: 119
ggggaaaatt tt                                                          12

<210> SEQ ID NO 120
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 120
agtcagtcac gcgagctcta                                                  20

<210> SEQ ID NO 121
```

```
<211> LENGTH: 26
<212> TYPE: DNA
<213> ORGANISM: Artificial Sequence
<220> FEATURE:
<223> OTHER INFORMATION: synthesized oligonucleotide

<400> SEQUENCE: 121
atactgactg actgactgac ctcaga                                    26

<210> SEQ ID NO 122
<211> LENGTH: 19
<212> TYPE: DNA
<213> ORGANISM: Artificial Sequence
<220> FEATURE:
<223> OTHER INFORMATION: synthesized oligonucleotide

<400> SEQUENCE: 122
gctctaatct gacctcagt                                            19
```